United States Patent
Chisari et al.

(10) Patent No.: US 6,607,727 B1
(45) Date of Patent: Aug. 19, 2003

(54) PEPTIDES FOR INDUCING CYTOTOXIC T LYMPHOCYTE RESPONSES TO HEPATITUS B VIRUS

(75) Inventors: Francis V. Chisari, Del Mar, CA (US); Carlo Ferrari, Parma (IT); Amalia Penna, Parma (IT); Gabriele Missael, Parma (IT)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/591,502

(22) PCT Filed: Aug. 1, 1994

(86) PCT No.: PCT/US94/08685
§ 371 (c)(1),
(2), (4) Date: May 20, 1996

(87) PCT Pub. No.: WO95/03777
PCT Pub. Date: Feb. 9, 1995

Related U.S. Application Data

(63) Continuation-in-part of application No. 08/100,870, filed on Aug. 2, 1993, now abandoned, which is a continuation-in-part of application No. 07/935,898, filed on Aug. 26, 1992, now abandoned, which is a continuation-in-part of application No. 07/749,540, filed on Aug. 26, 1991, now abandoned.

(51) Int. Cl.[7] .............................................. A61K 39/29
(52) U.S. Cl. ..................... 424/227.1; 514/12; 514/13; 514/14; 514/15; 514/16; 530/324; 530/326; 530/327; 530/328; 530/350
(58) Field of Search ...................... 424/227.1; 530/327, 530/328, 350, 324, 326; 514/12–16

(56) References Cited

U.S. PATENT DOCUMENTS

| | | | |
|---|---|---|---|
| 4,235,877 A | 11/1980 | Fullerton | 424/89 |
| 4,428,941 A | 1/1984 | Galibert et al. | 427/117 |
| 4,487,715 A | 12/1984 | Nitecki et al. | 260/112 |
| 4,599,230 A | 7/1986 | Milich et al. | 424/89 |
| 4,599,231 A | 7/1986 | Milich et al. | 424/89 |
| 4,818,527 A | 4/1989 | Thornton et al. | 424/88 |
| 4,882,145 A | 11/1989 | Thornton et al. | 424/88 |
| 4,935,235 A | 6/1990 | Rutter et al. | 424/88 |
| 5,017,558 A | 5/1991 | Vyas | 514/14 |
| 5,019,386 A | 5/1991 | Machida et al. | 424/89 |
| 5,039,522 A | 8/1991 | Neurath | 424/89 |
| 5,780,036 A * | 7/1998 | Chisari | 424/227.1 |
| 6,322,789 B1 * | 11/2001 | Vitiello et al. | 424/189.1 |

FOREIGN PATENT DOCUMENTS

| | | |
|---|---|---|
| EP | 013828 | 6/1980 |
| EP | 105481 | 4/1984 |
| EP | 431327 | 6/1991 |
| EP | 469281 | 6/1991 |
| EP | 534615 | 3/1992 |
| GB | 2034323 | 6/1980 |
| JP | 161999 | 8/1985 |
| WO | 9303753 | 3/1993 |
| WO | 9403205 | 2/1994 |
| WO | 9420127 | 9/1994 |

OTHER PUBLICATIONS

Ruppert et al., "Prominent role of secondary anchor residues in peptide binding to HLA–A2.1 molecules," Cell (1993), 74(5), 929–37.*

Bertoletti et al., "Natural variants of cytotoxic epitopes are T–cell receptor antagonists for antiviral cytotoxic T cells," Nature (Jun. 2, 1994) 369: 407–410.*

De Magistris et al., "Antigen analog–major histocompatibility complexes act as antagonists of the T cell receptor," Cell, (Feb. 21, 1992) 68 (4) 625–34.*

Jameson et al., "Clone–specific T cell receptor antagonists of major histocompatibility complex class I–restricted cytotoxic T cells," Journal of Experimental Medicine, (Jun. 1, 1993) 177 (6) 1541–50.*

Rehermann et al., The cytotoxic T lymphocyte response to multiple hepatitis B virus polymerase epitopes during and after acute viral hepatitis, Journal of Experimental Medicine, (Mar. 1, 1995) 181 (3) 1047–58.*

Falk et al., "Allele–specific motifs revealed by sequencing of self–peptides eluted from MHC molecules," Nature (May 23, 1991) 351:290–296.*

Zinkernagel et al., "The Lymphoreticular System in Triggering Virus Plus Self–Specific Cytotoxic T Cells: Evidence for T Help", *J. Exp. Med.,* 147:897–911 (1978).

Galibert et al., "Nucleotide Sequence of the Hepatitis B Virus Genome (subtype ayw) Cloned in *E. Coli*", *Nature* 281:646–650 (Oct. 25, 1979).

von Boehmer et al., "Distinct Ir Genes for Helper and Killer Cells in the Cytotoxic Response to H–Y Antigen", *J. Exp. Med.,* 150:1134–1142 (Nov., 1979).

Melief et al., "Cooperation Between Subclasses of T Lymphocytes in the in vitro Generation of Cytotoxicity Against a Mutant H–2K Difference An Analysis with Anti–Lyt Antisera", *Eur. J. Immunol.* 9:7–12 (1979).

Widmer et al., "Antigen–Driven Helper Cell–independent Cloned Cytolytic T Lymphocytes", *Nature* 294:750–752 (1981).

Lerner et al., "Chemically Synthesized Peptides Predicted form the Nucleotide Sequence of the Hepatitis B Virus Genome Elicit Antibodies Reactive with the Native Envelope Protein of Dane Particles" *Proc. Natl. Acad. Sci. USA* 78:3403–3407 (Jun. 1981).

(List continued on next page.)

Primary Examiner—Donna C. Wortman
(74) *Attorney, Agent, or Firm*—Townsend and Townsend and Crew LLP

(57) ABSTRACT

Peptides are used to define epitopes that stimulate HLA-restricted cytotoxic T lymphocyte activity against hepatitis B virus antigens. The peptides are derived from regions of HBV polymerase, and are particularly useful in treating or preventing HBV infection, including methods for stimulating the immune response of chronically infected individuals to respond to HBV antigens.

65 Claims, 23 Drawing Sheets

OTHER PUBLICATIONS

Bhatnagar et al., "Immune Response to Synthetic Peptide Analogues of Hepatitis B Surface Antigen Specific for the Determinant" *Proc. Natl. Acad. Sci. USA* 79:4400–44–4 (Jul. 1982).

Mondelli et al., "Specificity of T Lymphocyte Cytotoxicity to Autologous Hepatocytes in Chronic Hepatitis B Virus Infection: Evidence that T Cells are Directed Against HBV Core Antigen Expressed on Hepatocytes", *J. Immunol.*, 129:2773–2778 (12/82).

von Boehmer et al., "Autonomously Proliferating K/D–restricted Cytolytic T Cell Clones", *Eur. J. Immunol.* 13:176–179 (1983).

Neurath et al., "Specificity of Antibodies Elicited by a Synthetic Peptide having a Sequence in Common with a Fragment of a Virus Protein—The Hepatitis B Surface Antigen", *Develop. Biol. Standard,* 54:103–112 (1983).

von Boehmer et al., "Lyt–2 T Cell–Independent Functions of Lyt–2+ Cells Stimulated with Antigen or Concanavalin A", *J. Immunol.,* 133:59–64 (Jul., 1984).

Hopp, "Immunogenicity of a synthetic HBsAg Peptide: Enhancement by Conjugate to a Fatty Acid Carrier", *Molecular Immunol.* 21:13–16 (1984).

Milich et al., "Immunogenetics and Cellular Correlates of the Immune Response to Hepatitis B Surface Antigen Determinants", *Adv. Hepatitis Res.* Masson, NY, NY USA 91–109 (1984).

Fujii et al., "Peptide Chemistry 1983" published 1984 by Protein Research Foundation (OSAKA), pp. 215–220.

Sprent et al., "Properties of Purified T Cell Subsets", *J. Exp. Med.,* 162:2068–2088 (Dec., 1985).

Townsend et al., "The Epitopes of Influenza Nucleoprotein Recognized by Cytotoxic T Lymphocytes Can Be Defined with Short Synthetic Peptides", *Cell* 44:959–968 (Mar. 28, 1986).

Bessler et al., "The Synthetic Analog of Bacterial Lipoprotein are Potent Immunoadjuvants in Combination with or Covalently Linked to Antigen", *Prog. Leukocyte Biol.* 5:337–344 (1986).

Watari et al., "A Synthetic Peptide Induces Long–Term Protection from Lethal Infection with Herpes Simplex Virus 2", *J. Exp. Med.,* 165:459–470 (Feb., 1987).

Gotch et al., "Cytotoxic T Lymphocytes Recognize a Fragment of Influenza Virus Matrix Protein in Associate with HLA–A2", *Nature* 326:881–882 (Apr. 30, 1987).

Buller et al. "Induction of Cytotoxic T–Cell Responses in vivo in Absence of CD4 Helper Cells" *Nature* 328:76–79 (Jul. 2, 1987).

Milich et al., "Immune Response to Hepatitis B Virus Core Antigen (HBcAg): Localization of T Cell Recognition Sites Within HBcAg/HBeAg", *J. Immunol.,* 139:1223–1231 (Aug. 15, 1987).

Milich et al., "Antibody Production to the Nucleocapsid and Envelope of the Hepatitis B Virus Primed by a Single Synthetic T Cell Site", *Nature* 329:547–549 (Oct. 8, 1987).

Mondelli et al. "Definition of Hepatitis B Virus (HBV)–specific Target Antigens Recognized by Cytotoxic T Cells in Acute HBV Infection", *Clin. Exp. Immunol.,* 68:242–250 (1987).

Milich et al., "Hepatitis B Synthetic Immunogen Comprised of Nucleocapsid T–cell Sites and an Envelope B–cell Epitope", *Proc. Natl. Acad. Sci. USA* 85:1610–1614 (Mar., 1988).

Celis et al., "Recognition of Hepatitis B Surface Antigen by Human T Lymphocytes" *J. Immunol.* 140:1808–1815 (Mar. 15, 1988).

Carbone et al. "Induction of Cytotoxic T Lymphocytes by Primary in vitro Stimulation with Peptides", *J. Exp. Med.,* 167:1767–1779 (Jun., 1988).

Moore et al., "Introduction of Soluble Protein into the Class I Pathway of Antigen Processing and Presentation", *Cell* 54:777–785 (Sep. 9, 1988).

Milich et al., "Comparative Immunogenicity of Hepatitis B Virus Core and E Antigens", *J. Immunol.* 141:3617–3624 (Nov. 15, 1988).

Gotch et al. "Recognition of Influenza A Matrix Protein by HLA–A2–Restricted Cytotoxic T Lymphocytes", *J. Exp. Med.* 163:2045–2057 (Dec., 1988).

Mack et al. "Hepatitis B Virus Particles Contain a Polypeptide Encoded by the Largest Open Reading Frame: A Putative Reverse Transcriptase", *J. Virol.* 62:4786–4790 (Dec., 1988).

Milich, "T– and B–cell Recognition of Hepatitis B Viral Antigens", *Immunol. Today* 9:380–386 (1988).

Hayashi et al., "Studies on Peptides CLXVI. Solid–Phase Synthesis and Immunological Properties of Fragment Peptides Related to Human Hepatitis B virus Surface Antigen (HBsAg) and Its Pre–S2 Gene" *Chem. Pharm. Bull.* 36(12):4993–4994 (1988).

Braciale et al., "Class I Major Histocompatibility Complex–restricted Cytolytic T Lymphocytes Recognize a Limited Number of sites on the Influenza Hemagglutinin", *Proc. Natl. Acad. Sci. USA* 86:277–281 (Jan., 1989).

Ishioka et al., "Induction of Class I MHC–restricted, Peptide–specific Cytolytic T Lymphocytes by Peptide Priming in vivo", *J. Immunol.,* 143:1094–1100 (Aug. 15, 1989).

Klavinskis et al., "Molecularly Engineered Vaccine Which Expresses an Immunodominant T–cell Epitope Induces Cytotoxic T Lymphocytes that Confer Protection for Lethal Virus Infection," *J. Virol.,* 63:4311–4316 (Oct., 1989).

Bevan, "Stimulating Killer Cells", *Nature* 342:478–479 (Nov. 30, 1989).

Deres et al., "In Vivo Priming of Virus–Specific Cytotoxic T Lymphocytes with Synthetic Lipopeptide Vaccine", *Nature* 342:561–564 (Nov. 30, 1989).

Tam et al., "Vaccine Engineering: Enhancement of Immunogenicity of Synthetic Peptide Vaccines Related to Hepatitis in Chemically Defined Models Consisting of T– and B–cell Epitopes", *Proc. Natl. Acad. Sci. USA* 86:9084–9088 (12/89).

Chisari et al., "Hepatitis B Virus Structure and Biology", *Microbial Pathogenesis* 6:311–325 (1989).

Moriyama et al., "Immunobiology and Pathogenesis of Hepatocellular Injury in Hepatitis B Virus Transgenic Mice", *Science* 248:361–364 (Apr. 20, 1990).

Aichele et al., "Antiviral Cytotoxic T Cell Response Induced by in vivo Priming with a Free Synthetic Peptide", *J. Exp. Med.,* 171:1815–1820 (May, 1990).

Aggarwal et al., "Oral Salmonella: Malaria Circumsporozoite Recombinants Induce Specific $CD8^+$ Cytotoxic T Cells", *J. Exp. Med.,* 172:1083–1090 (Oct., 1990).

Van Bleek et al., "Isolation of an Endogenously Processed Immunodominant Viral Peptide from the Class $IH-2K^b$ Molecule", *Nature* 348:213–216 (Nov. 15, 1990).

Rotzschke et al., "Isolation and Analysis of Naturally Processed Viral Peptides as Recognized by Cytotoxic T cells", *Nature* 348:252–254 (Nov. 15, 1990).

Golvano et al., "Polarity of Immunogens: Implications for Vaccine Design", *Eur. J. Immunol.* 20:2363–2366 (1990).

Ishioka et al., "Class I MHC–restricted, Peptide–specific Cytotoxic T Lymphocytes Generated by Peptide Priming in vivo", *Vaccines 90,* Cold Spring Harbor Press, pp. 7–11 (1990).

Wakita et al "Gamma–Interferon Production in Response to Hepatitis B Core Protein & its Synthetic Peptides in Patients with Chronic Hepatitis B Virus Infection", *Digestion* 47:149–155 (1990).

Kast et al., "Protection Against Lethal Sendai Virus Infection by in vivo Priming of Virus–specific Cytotoxic T Lymphocytes with a Free Synthetic Peptide", *Proc. Natl. Acad. Sci. USA* 88:2283–2287 (Mar., 1991).

Schumacher et al., "Peptide Selection by MHC Class I Molecules" *Nature* 350:703–706 (Apr. 25, 1991).

Ferrari et al., "Identification of Immunodominant T Cell Epitopes of the Hepatitis B Virus Nucleocapsid Antigen", *J. Clin. Invest.,* 88:214–222 (Jul., 1991).

Bertoletti, "HLA Class I–restricted Human Cytotoxic T Cells Recognize Endogenously Synthesized Hepatitis B Nucleocapsid Antigen", *Proc. Natl. Acad. Sci. USA* 88:10445–10449 (12/91).

Penna et al., "Cytotoxic T Lymphocytes Recognize an HLA–A2–restricted Epitope Within the Hepatitis B Virus Nucleocapsid Antigen", *J. Exp. Med.* 174:1565–1570 (Dec., 1991).

Sarobe et al. "Induction of Antibodies Against Peptide Hapten Does Not Require Covalent Linkage Between Hapten & Class II Presentable T Helper Peptide", *Eur. J. Immunol.* 21:1555–1558 (1991).

Cassell et al., "Linked Recognition of Helper and Cytotoxic Antigenic Determinants for the Generation of Cytotoxic T Lymphocytes", *Ann. N.Y. Acad. Sci.,* pp. 51–60 (1991).

Penna et al., "Hepatitis B Virus (HBV–Specific Cytotoxic T Cell (CTL) Response in Humans: Characterization of HLA Class II–Restricted CTLs That Recognize Endogenously Synthesized HBV Envelope Antigens", *J. Virol.* 66:1193–1198 (Feb., 1992).

Guilhot et al., "Hepatitis B Virus (HBV)–Specific Cytotoxic T–Cell Response in Humans: Production of Target Cells by Stable Expression of HBV–Encoded Proteins in Immortalized Human B–Cell Lines", *J. Virol.* 66:2670–2678 (May, 1992).

* cited by examiner

FIG. 3A
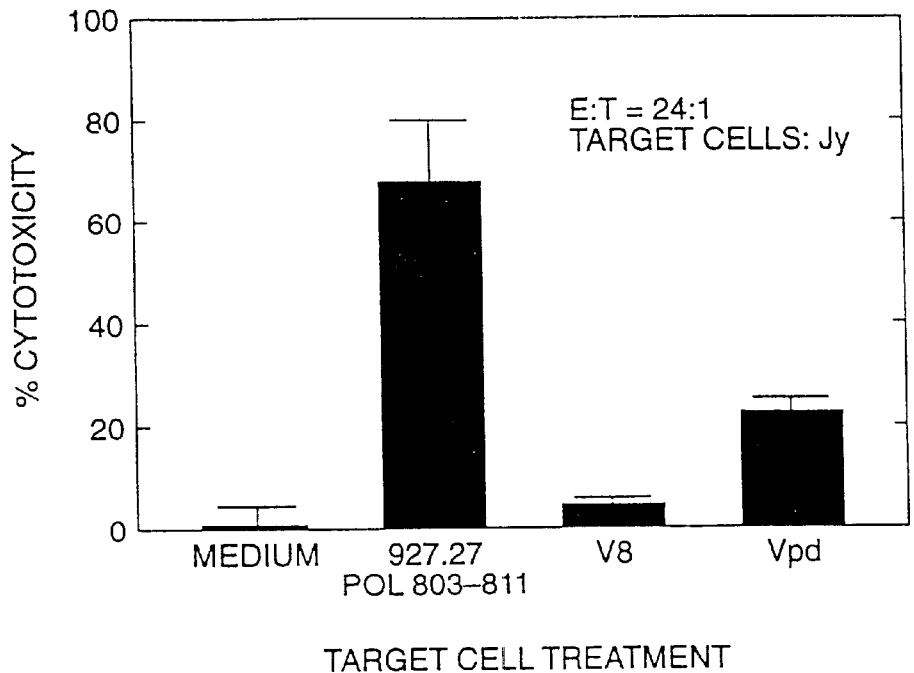
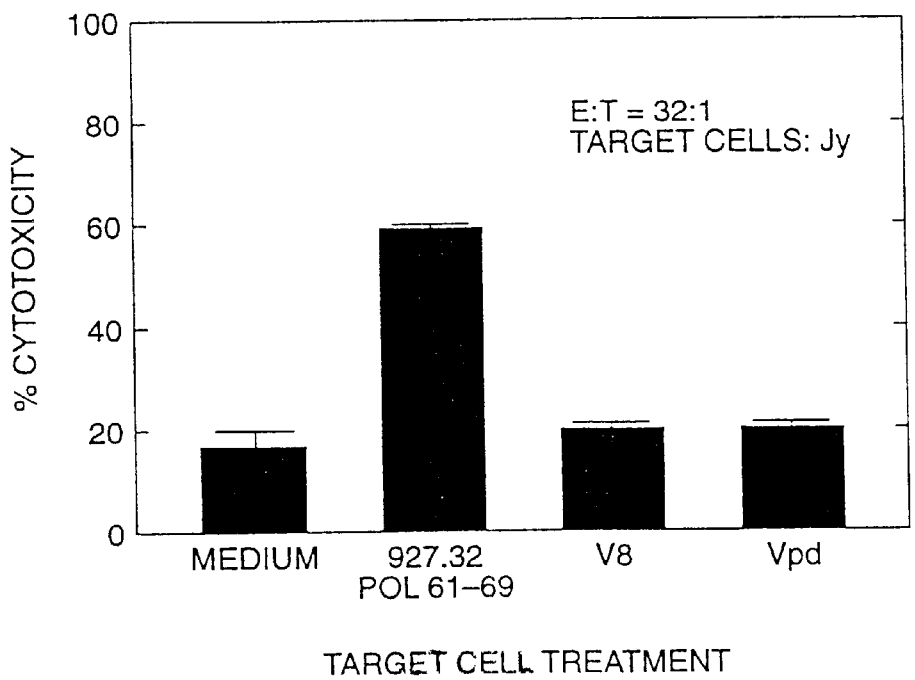
FIG. 3B

FIG. 4A

```
 1   MPLSYQHFRKLLLLDD--EA    GPLEEELPRLADEGLNRRVA    EDLNLGNLNVSIPWTHKVGN
39   MPLSYQHFRKLLLLDD--EA    GPLEEELPRLADEGLNRRVA    EDLNLGNLNVSIPWTHKVGN
40   MPLSYQHFRKLLLLD???EA    GPLEEELPRLADEGLNRRVA    EDLNLGNLNVSIPWTHKVGN
41   MPLSYQHFRKLLLLDD--EA    GPLEEELPRLADEGLNRRVA    EDLNLGNLNVSIPWTHKVGN
42   MPLSYQHFRKLLLLDD--EA    GPLEEELPRLADEGLNRRVA    EDLNLGNLNVSIPWTHKVGN
43   MPLSYQHFRKLLLLDD--EA    GPLEEELPRLADEGLNRRVA    EDLNLGNLNVSIPWTHKVGN
44   MPLSYQHFRKLLLLDD--EA    GPLEEELPRLADEDLNRRVA    EDLNLGNLNVSIPWTHKVGN
45   MPLSYQHFRKLLLLDD--EA    GPLEEELPRLADADLNRRVA    EDLNLGNLNVSIPWTHKVGN
46   MPLSYQHFRKLLLLDDGTEA    GPLEEELPRLADEGLNRRVA    EDLNLGNPNVSIPWTHKVGN
47   MPLSYQHFRKLLLLDD--EA    GPLEEELPRLADEGLNRRVA    EDLNLGNLNVSIPWTHKVGN
48   MPLSYQHFRKLLLLDE--EA    GPLEEELPRLADEGLNRRVA    EDLNLGNLNVSIPWTHKVGN
49   MPLSYQHFRKLLLLDD--EA    GPLEEELPHLADEGLNRRVA    EDLNLGNLNVSIPWTHKVGN
50   MPLSYQHFRKLLLLDDGTEA    GPLEEELPRLADADLNRRVA    EDLNLGNLNVSIPWTHKVGN
51   MPLSYQHFRKLLLLDD--EA    GPLEEELPRLADEGLNRPVA    EDLNLGNLNVSIPWTHKVGN
52   MPLSYQHFRKLLLLDDGTEA    GPLEEELPRLADADLHRRVA    EDLNLGNLNVSIPWTHKVGN
53   MPLSYQHFRKLLLLDD--EA    GPLEEELPRLADADLHRRVA    EDLNLGNLNVSIPWTHKVGN
54   MPLSYQHFRRLLLLDD--EA    GPLEEELPRLADEGLNRRVA    EDLNLGNLNVSIPWTHKVGN
55   MPLSYQHFRRLLLLDD--EA    GPLEEELPRLADEGLNRRVA    EDLNLGNLNVSIPWTHKVGN
56   MPLSYQHFRRLLLLDD--EA    GPLEEELPRLADEGLNRRVA    EDLNLGNLNVSIPWTHKVGN
57   MPLSYQHFRKLLLLDD--EA    GPLEEELPRLPDQGLNRRVA    EDLNLGNLNVSIPWTHKVGN
58   MPLSYQHFRRLLLLHD--EA    GPLEEELPrLaDegLnrrVA    EDLNLGNLNVSIPWTHKVGN
158  MPLSYQHFRkLLLLddGTEA    GPLEEELPrLaDegLnrrVA    EDLNLGNlNVSIPWTHKVGN
```

FIG. 4B

```
    61
39  FTGLYSSTVPVFNPEWQTPS  FPHIHLQEDIINRCQQYVGP  LTVNEKRRLKLIMPARFYPN
40  FTGLYSSTVPIFNPEWQTPS  FPHIHLQEDIINRCQQYVGP  LTVNEKRRLKLIMPARFYPN
41  FTGLYSSTVPIFNPESQTPS  FPNIHLQEDIINRCQQYVGP  LTVNEKRRLKLIMPARFYPN
42  FTGLYSSTVPVLNPESQTPS  FPNIHLQEDIINRCQQYVGP  LTVNEKRRLKLIMPARFYPN
43  FTGLYSSTVPVFNPEWQTPS  FPHIHLQEDIINRCQQYVGP  LTVNEKRRLKLIMPARFYPN
44  FTGLYSSTVPVFNPEWQTPS  FPHIHLQEDIINRCQQYVGP  LTVNEKRRLKLIMPARFYPK
45  FTGLYSSTVPVFNPEWQTPS  FPHIHLQEDIINRCQQYVGP  LTVNEKRRLKLIMPARFYPT
46  FTGLYSSTVPIFNPEWQTPS  FPKIHLQEDIINRCQQFVGP  LTVNEKRRLKLIMPARFYPN
47  FTGLYSSTVPVFNPEWQTPS  FPDIHLQEDIVDRCKQFVGP  LTVNENRRLKLIMPARFYPN
48  FTGLYSSTVPCFNPKWQTPS  FPDIHLQEDIVDRCKQFVGP  LTVNENRRLKLIMPARFYPN
49  FTGLYSSTVPSFNPQWQTPS  FPDIHLQEDIINKCKQFVGP  LTVNEKRRLKLIMPARFYPN
50  FTGLYSSTVPSFNPKWQTPS  FPDIHLQEDIINRCEQFVGP  LTVNENRRLKLIMPARFYPT
51  FTGLYSSTAPIFNPEWQTPS  FPKIHLQEDIINRCQQFVGP  LTVNEKRRLKLIMPARFYPT
52  FTGLYSSTVPIFNPEWQTPS  FPKIHLQEDIIKKCEQFVGP  LTVNEKRRLKLIMPARFYPN
53  FTGLYSSTVPVFNPEWQTPS  FPHIHLQEDIINRCQQFVGP  LTVNEKRRLKLIMPARFYPK
54  FTGLYSSTVPVFNPHWKTPS  FPNIHLHQDIIKKCEQFVGP  LTVNEKRRLQLIMPARFYPK
55  FTGLYSSTVPVFNPHWKTPS  FPNIHLHQDIIKKCEQFVGP  LTVNEKRRLQLIMPARFYPK
56  FTGLYSSTVPVFNPHWKTPS  FPNIHLHQDIIKKCEQFVGP  LTVNEKRRLQLIMPARFYPK
57  FTGFYSSTVPVFNPHWETPS  FPNIHLHQDIIKKCEQFVGP  LTVNEKRRLQLIMPARFYPK
58  FTGLYSSTVPVFNPHWKTPS  FPNIHLHQDIINRCQQFVGP  LTVNEKRRLQLIMPARFYPN
158 FTGlYSSTvPvfNPewqTPS  FP.IHLqeDIinrCqQfVGP  LTVNEkRRLkLIMPARFYPn
```

FIG. 4C

```
     121
 39  LTKYLPLDKGIKPYYPEHAV  NHYFKTRHYLHTLWKAGILY  KRETTRSASFCGSPYSWEQE
 40  LTKYLPLDKGIKPYYPEHAV  NHYFKTRHYLHTLWKAGILY  KRETTRSASFCGSPYSWEQE
 41  LTKYLPLDKGIKPYYPEHAV  NHYFKTRHYLHTLWKAGILY  KRETTRSASFCGSPYSWEQE
 42  LTKYLPLDKGIKPYYPEHAV  NHYFKTRHYLHTLWKAGILY  KRETTRSASFCGSPYSWEQE
 43  LTKYLPLDKGIKPYYPEHAV  NHYFKTRHYLHTLWKAGILY  KRETTRSASFCGSPYSWEQE
 44  LTKYLPLDKGIKPYYPEHAV  NHYFKTRHYLHTLWKAGILY  KRETTRSASFCGSPYSWEQE
 45  LTKYLPLDKGIKPYYPEHAV  NHYFKTRHYLHTLWKAGILY  KRETTRSASFCGSPYSWEQE
 46  LTKYLPLDKGIKPYYPDQVV  NHYFKTRHYLHTLWKAGILY  KRESTHSASFCGSPYSWEQD
 47  HTKYLPLDKGIKPYYPEHVV  NHYFQTRHYLHTLWKAGILY  KRETTRSASFCGSPYSWEQD
 48  VTKYLPLDKGIKPYYPEYVV  NHYFQTRHYLHTLWKAGILY  KRETTRSASFCGSPYSWEQE
 49  VTKYLPLDKGIKPYYPEHVV  NHYFQTRHYLHTLWKAGILY  KRETTRSASFCGSPYSWEQD
 50  VTKYLPLDKGIKPYYPDQVV  NHYFQTRHYLHTLWKAGILY  KRETTRSASFCGSPYSWEQE
 51  HTKYLPLDKGIKPYYPDQVV  NHYFQTRHYLHTLWKAGILY  KRETTRSASFCGSPYSWEQE
 52  HTKYLPLDKGIKPYYPDQVV  NHYFKTRHYLHTLWKAGILY  KRETTRSASFCGSPYSWEQE
 53  LTKYLPLDKGIKPYYPEYAV  NHYFKTRHYLHTLWKAGILY  KRETTRSASFCGSPYSWEQD
 54  VTKYLPLDKGIKPYYPEHLV  NHYFKTRHYLHTLWKAGILY  KRETTHSASFCGSPYSWEQE
 55  VTKYLPLDKGIKPYYPEYLV  NHYFQTRHYLHTLWKAGILY  KRETTHSASFCGSPYSWEQD
 56  VTKYLPLDKGIKPYYPEHLV  NHYFQTRHYLHTLWKAGILY  KRETTHSASFCGSPYSWEQE
 57  VTKYLPLDKGIKPYYPEHLV  NHYFQTRHYLHTLWKAGILY  KRETTHSASFCGSPYSWEQD
 58  VTKYLPLDKGIKPYYPEHLV  NHYFQTRHYLHTLWKAGILY  KRETTHSASFCGSPYSWEQE
158  TKYLPLDKGIKPYYPeh.V   NHYFqTRHYLHTLWKAGILY  KRetTrSASFCGSPYSWEQe
```

FIG. 4D

```
    181
39  LQHGRLVFQTSTRHGDESFC  SQSSGILSRSPVGPCVRSQL  KQSRLGLQPQQGSMARGKSG
40  LQHGRLVFQTSTRHGDESFC  SQSSGILSRSPVGPCVRSQL  KQSRLGLQPQQGSLARGKSG
41  LRHGRLVFQTSTRHGDESFC  SQSSGILSRSPVGPCVRSQL  KQSRLGLQPQQGSLARGNQG
42  LQHGRLVFQTSTRHGDESFC  SQSSGILSRSPVGPCIRSQL  KQSRLGLQPQQGSLARGKSG
43  LQHGRLVFQTSTRHGDESFC  SQSSGILSRSPVGPCVRSQL  KQSRLGLQPQQGSLARGKSG
44  LQHGRLVFQTSTRHGDESFC  SQSSGILSRSPVGPCVRSQL  TQSRLGLQPQQGSLARGKSG
45  LQHGRLVFQTSTRHGDESFC  SQSSGILSRSPVGPCVRSQL  KQSRLGLQPQQGSLARGKSG
46  LQH--------SQRHGDESFC SQPSGIPSRSSVGPCIRSQL  NKSRLGLQPHQGPLASSQPG
47  LQHGRLVFQTSKRHGDKSFC  PQSSGILPRSSVGPCIQSQL  RKSRLGPQPTQGQLAGRPQG
48  LQHGRLVFQTSKRHGDKSFC  PQSSGILPRSSVGPCIQSQL  RKSRLGPQPEQGQLAGRQQG
49  LQHGRLVLQTSTRHGDKSFR  PQSSGILSRSPVGPCIQSQL  RQSRLGPQPTQGQLAGLQQG
50  LQHGRLVLQTSTRHGDKSFR  PQSSGILSRSPVGPCIQSQL  RQSRLGPQPTQGQLAGLQQG
51  LQHGRLVIKTSQRHGDESFC  SQSSGILSRSSVGPCIRSQL  KQSRLGLQPHQGPLASSQPG
52  LQHGRLVIKTSCRHGDESFC  SQSSGILSRSSVGPCIRSQL  KQSRLGLQPRQGRLASSQPS
53  LQHGRLVFQTSTRHGDESFC  SQSSGILSRPVGPCVRSQL   KQSRLGLQPQQGSLARGKSG
54  LQHG---------AESFH    QQSSGILSRPPVGSSLQSKH  RKSRLGLQSQQGHLARRQQG
55  LQHG---------AESFH    QQSSGILSRPPVGSSLQSKH  RKSRLGLQSQQGHLARRQQG
56  LQHG---------AESIH    QQSSGILSRPPVGSSLQSKH  RKSRLGLQSQQGHLARRQQG
57  LQHG---------AESIH    QQSSGILSRPPVGSSLQSKH  RKSRLGLQSQQGHLARRQQG
58  LQHG---------AESFH    QQSSGILSRPPVGSSLQSKH  RKSRLGLQSQQGHLARRQQG
158 LqHGRLVfqTStRHGdeSfc  sQssGIlsRspVGpc.rSql  .qSRLGlQpqQG.lAr.qqg
```

FIG. 4E

```
     241
39   RSGSIRARVHPTTRRSFGVE   PSGSGHIDNSASSTSSCLHQ   SAVRKTAYSHLSTSKRQSSS
40   RSGSIRARVHPTTRRSFGVE   PSGSGHIDNSASSTSSCLHQ   SAVRKTAYSHLSTSKRQSSS
41   RSGRLRARVHPTTRRSFGVE   PSGSGHIDNSASSASSCFHQ   SAVRKTAYSHLSTSKRQSSS
42   RSGSIWARVHSTTRRSFGVE   PSGSGHIDNSASSASSCLYQ   SAVRKTAYSHLSTSKRQSSS
43   RSGSIRARVHPTTRRSFGVE   PSGSGHIDNRASSTSSCLHQ   SAVRKTAYSHLSTSKRQSSS
44   RSGSIRARVPPTTRRSFGVE   PAGSGHIDNRASSTSSCLHQ   SAVRKTAYSHLSTSKRQSSS
45   RSGSIRARVPPTTRRSFGVE   PSGSGHIDNRASSTSSCLHQ   SAVRKTAYSHLSTSKRQSSS
46   RSGSIRARAHPSTRRYFGVE   PSGSGHIDHSVNNSSSCLHQ   SAVRKAAYSHLSTSKRQSSS
47   GSGSIRARIHPSPWGTVGVE   PSGSGHTHICASSSSSCLHQ   SAVRTAAYSPISTSKGHSSS
48   GSGSIRARVHPSPWGTVGVE   PSGSGPTHNCASSSSSCLHQ   SAVRKAAYSLIPTSKGHSSS
49   GSGSIRAGIHSTPWGTVGVE   PSSSGHTHNCANSSSSCLHQ   SAVRKEAYSPVSTSKRHSSS
50   GSGSIRAGIHSTPWGTVGVE   PSSSGHTHNCANSSSSCLHQ   SAVRKEAYSPVSTSKRHSSS
51   RSGSIRARVHPSTRRCFGVE   PSGSGHVDPSVNNSSSCLRQ   SAVRKAAYSHLSTSKRQSSS
52   RSGSIRAKAHPSTRRYFGVE   PSGSGHIDHSVNNSSSCLHQ   SAVRKAAYSHLSTSKRQSSS
53   RSGSIWSRVHPTTRRPFGVE   PSGSGHIDNTASSTSSCLHQ   SAVRKTAYSHLSTSKRQSSS
54   RSWSIRAGFHPTARRPFGVE   PSGSGHTTNFASKSASCLHQ   SPVRKAAYPAVSTFEKHSSS
55   RSWSIRAGIHPTTRRPFGVE   PSGSGHTRNVASKSASCLYQ   SPVRKAAYPAVSTFEKHSSS
56   RSWSIRAGFHPTARRPFGVE   PSGSGHTTNFASKSASCLHQ   SPVRKAAYPSVSTFERHSSS
57   WSWSIRAGTHPTARRPFGVE   PSGSGHTTHRASKSASCLYQ   SPDRKATYPSVSTFERHSSS
58   RSWSIRAGFHPTARRSFGVE   PSGSGHTTYRASKSASCLYQ   SPVRKAAYPSVSTFEKHSSS
158  rSgsirarvhpttrr.fGVE   PsgSGhidn.assssSClhQ   SavRkaaYshlsTskrqSSS
```

FIG. 4F

```
    301
39  GHAVEFHNIPPSSARSQSEG  PIFSCWWLQFRNSKPCSDYC  LTHIVNLLEDWGPCTEHGEH
40  GHAVELHNIPPSSARPQSEG  PILSCWWLQFRNSKPCSDYC  LTHIVNLLEDWGPCTEHGEH
41  GHAVELHNIPPSSARSQSEG  PIFSCWWLQFRNSKPCSDYC  LTHIVNLLEDWGPCTEHGEH
42  GHAVELHNIPPSCARSQSEG  PISSCWWLQFRNSEPCSDYC  LTHIVNLLEDWGPCTEHGEH
43  GHAVELHNIPPSSARPQSEG  PILSCWWLQFRNSKPCSDYC  LTHIVNLLEDWGPCTEHGEH
44  GHAVELHHISPPSSARSQSEG PIFSSWWLQFRNSKPCCDYC  LTHIVNLLEDWGPCTEHGEH
45  GHAVELHHISPSPARSQSEG  PIFSSWWLQFRNSKPCSDYC  LTHIVNLLEDWGPCTEHGEH
46  GHAVELHHISPSPARSQSQG  SVSSCWWLQFRNSKPCSEYC  LSHLVNLREDWGPCDDHGEH
47  GHAVEFHCLAPSSAGSQSQG  SVLSCWWLQFRNSKPCSEYC  LSHIVNLIEDWGPCAEHGEH
48  GHAVELHHFPPNSSRSRSQG  PVLSCWWLQFRNSEPCSEYC  LCHIVNLIEDWGPCTEHGEH
49  GNAVELHHFPPNSSRSQSQG  SVLSCWWLQFRNSKPCSEYC  LFHIVNLIDDWGPCAEHGEH
50  GHAVELHHVPPNSSRSQSQG  SVFSCWWLQFRNSKPCSEHC  LFHIVNLIEDWGPCAEHGEH
51  GHAVEFHCLPPSSARPQSQG  SVSSCWWLQFRNSKPCSEYC  LSHLVNLREDRGPCDEHGEH
52  GHAVEFHCLPPNSAGSQSQG  PIFSCWWLQFRNSKPCSDYC  LSHLVNLREDWGPCDEHGEH
53  GHAVELHNIPPSSARSQSEG  PIFSCWWLQFRNSKPCSDYC  LTHIVNLLEDWGPCTEHGEH
54  GHAVEFHNLPPNSARSQSER  PVFPCWWLQFRNSKPCSDYC  LSLIVNLLEDWGPCAEHGEH
55  GHAVELHNLPPNSARSQSER  PVFPCWWLQFRNSKPCSDYC  LSHIVNLLEDWGPCAEHGEH
56  GHAVELHNLPPNSARSQSER  PVFPCWWLQFRNSKPCSDYC  LSLIVNLLEDWGPCAEHGEH
57  GRAVELHNFPPNSARSQSER  PIFPCWWLQFRNSKPCSDYC  LSLIVNLLEDWGPCDEYGEH
58  GHAVELHNLPPNSARSQSER  PVFPCWWLQFRNSKPCSDYC  LSLIVNLREDWGPCTEHGEH
158 GhAVElHn.pPnsarsqSeg  pvfscWWLQFRNskPCsdyC  L.hiVNLleDwGPCtehGEH
```

FIG. 4G

```
      361
 39   NIRIPRTPARVTGGVFLVDK  NPHNTTESRLVVDFSQFSRG  STHVSWPKFAVPNLQSLTNL
 40   NIRIPRTPARVTGGVFLVDK  NPHNTTESTLVVDFSQFSRG  STHVSWPKFAVPNLQSLTNL
 41   NIRIPRTPARVTGGVFLVDK  NPHNTTESRLVVDFSQFSRG  STHVSWPKFAVPNLQSLTNL
 42   NIRIPRTPARVTGGVFLVDK  NPHNTTESRLVVDFSQFSRG  STHVSWPKFAVPNLQSLTNL
 43   NIRIPRTPARVTGGVFLVDK  NPHNTTESRLVVDFSQFSRG  STHVSWPKFAVPNLQSLTNL
 44   NIRIPRTPARVTGGVFLVDK  NPHNTTESRLVVDFSQFSRG  STHVSWPKFAVPNLQSLTNL
 45   NIRIPRTPARVTGGVFLVDK  NPHNTTESRLVVDFSQFSRG  STHVSWPKFAVPNLQSLTNL
 46   HIRIPRTPARVTGGVFLVDK  NPHNTAESRLVVDFSQFSRG  STHVSWPKFAVPNLQSLTNL
 47   RIRTPRTPARVTGGVFLVDK  NPHNTTESRLVVDFSQFSRG  ITRVSWPKFAVPNLQSLTNL
 48   RIRTPRTPARVTGGVFLVDK  NPHNTTESRLVVDFSQFSRG  NTRVSWPKFAVPNLQSLTNL
 49   RIRTPRTPARVTGGVFLVDK  NPHNTTESRLVVDFSQFSRG  NTRVSWPKFAVPNLQSLTNL
 50   RIRTPRTPARVTGGVFLVDK  NPHNTAESRLVVDFSQFSRG  NTRVSWPKFAVPNLQSLTNL
 51   HIRIPRTPARVTGGVFLVDK  NPHNTTESRLVVDFSQFSRG  ITRVSWPKFAIPNLQSLTNL
 52   HIRIPRTPARVTGGVFLVDK  NPHNTAESRLVVDFSQFSRG  ISRVSWPKFAVPNLQSLTNL
 53   NIRIPRTPARVTGGVFLVDK  NPHNTTESRLVVDFSQFSRG  STHVSWPKFAVPNLQSLTNL
 54   HIRIPRTPSRVTGGVFLVDK  NPHNTAESRLVVDFSQFSRG  NYRVSWPKFAVPNLQSLTNL
 55   HIRIPRTPSRVTGGVFLVDK  NPHNTAESRLVVDFSQFSRG  NYRVSWPKFAVPNLQSLTNL
 56   HIRIPRTPARVTGGVFLVDK  NPHNTAESRLVVDFSQFSRG  NYRVSWPKFAVPNLQSLTNL
 57   HIRIPRTPSRVTGGVFLVDK  NPHNTAESRLVVDFSQFSRG  NYRVSWPKFAVPNLQSLTNL
 58   HIRIPRTPARVTGGVFLVDK  NPHNTAESRLVVDFSQFSRG  NYRVSWPKFAVPNLQSLTNL
158   .IRiPRTPaRVTGGVFLVDK  NPHNTtESrLVVDFSQFSRG  .trVSWPKFAVPNLQSLTNL
```

FIG. 4H

```
     421
39   LSSNLSWLSLDVSAAFYHIP  LHPAAMPHLLVGSSSGLPRYV  ARLSSTSRNINHQHGAMQDL
40   LSSNLSWLSLDVSAAFYHIP  LHPAAMPHLLVGSSSGLPRYV  VCLSSTSKNINYQHGTMQDL
41   LSSNLSWLSLDVSAAFYHIP  LHPAAMPHLLVGSSSGLPRYV  ARLSSTSRNINYQHGTMQDL
42   LSSNLSWLSLDVSAAFYHIP  LHPAAMPHLLVGSSSGLPRYV  ARLSSTSRNINYQHGTMQDL
43   LSSNLSWLSLDVSAAFYHIP  LHPAAMPHLLVGSSSGLPRYV  ARLSSTSRNINHQHGTMQDL
44   LSSNLSWLSLDVSAAFYHIP  LHPAAMPHLLVGSSSGLPRYV  ARLSSTSRNINHQHGTMQDL
45   LSSNLSWLSLDVSAAFYHIP  LHPAAMPHLLVGSSSGLPRYV  ARLSSTSRNINHQHGTMQDL
46   LSSNLSWLSLDVSAAFYHIP  LHPAAMPHLLIGSSSGLSRYV  ARLSSNSRINNNQYGTMQDL
47   LSSNLSWLSLDVSAAFYHLP  LHPAAMPHLLVGSSSGLSRYV  ARLSSNSRIINHQHGTMQDL
48   LSSNLSWLSLDVSAAFYHLP  LHPAAMPHLLVGSSSGLSRYV  ARLSSNSRIINHQHGTMQNL
49   LSSDLSWLSLDVSAAFYHLP  LHPAAMPHLLVGSSSGLSRYV  ARLSSNSRIINHQHRTMQNL
50   LSSDLSWLSLDVSAAFYHIP  LHPAAMPHLLVGSSSGLSRYV  ARLSSNSRIINHQHRTMQNL
51   LSSNLSWLSLDVSAAFYHIP  LHPAAMPHLLIGSSSGLSRYV  ARLSSNSRINNNQYGTMQNL
52   LSSNLSWLSLDVSAAFYHIP  LHPAAMPHLLVGSSSGLSRYV  ARLSSNSRINNNQYGTMQNL
53   LSSNLSWLSLDVSAAFYHLP  LHPAAMPHLLVGSSSGLSRYV  ARLSSNSRINIYQHGTMQNL
54   LSSNLSWLSLDVSAAFYHLP  LHPAAMPHLLVGSSSGLSRYV  ARLSSNSRILNNQHGTMPDL
55   LSSNLSWLSLDVSAAFYHIP  LHPAAMPHLLVGSSSGLSRYV  ARLSSNSRIFNYQHGTMQNL
56   LSSNLSWLSLDVSAAFYHLP  LHPAAMPHLLVGSSSGLSRYV  ARLSSNSRILNHQHGTMPNL
57   LSSNLSWLSLDVSAGFYHLP  LHPAAMPHLLVGSSVSRYV   ARLSSNSRNNNNQYGTMQNL
58   LSSNLSWLSLDVSAaFYHLP  LHPAAMPHLLVGSSSGLSRYV  ARLSSNSRIFNNQHGTMQNL
158  LSSnLSWLSLDVSAaFYHiP  LHPAAMPHLLvGSSSGlsRYV  arLSSnSriiN.QhgtMqnL
```

FIG. 4I

```
    481
39  HDSCSRNLYVSLLLLYKTFG  RKLHLYSHPIILGFRKIPMG  VGLSPFLLAQFTSAICSVVR
40  HDSCSRNLYVSLFLLYKTFG  RKLHLYSHPIILGFRKIPMG  VGLSPFLLAQFTSAICSVVR
41  HDSCSRNLYVSLLLLYKTFG  RKLHLYSHPIILGFRKIPMG  VGLSPFLLAQFTSAICSVVR
42  HDSCSRNLYVSLLLLYKTFG  RKLHLYSHPIILGFRKIPMG  VGLSPFLLAQFTSAICSVVR
43  HDSCSRNLYVSLLLLYKTFG  RKLHLYSHPIILGFRKIPMG  GGLSPFLLAQFTSAICSVVR
44  HDSCSRNLYVSLLLLYKTFG  RKLHLYSHPIILGFRKIPMG  GGLSPFLLAQFTSAICSVVR
45  HDSCSRNLYVSLLLLYKTFG  RKLHLYSHPIILGFRKIPMG  GGLSPFLLAQFTSAICSVVR
46  HDSCSRQL
47  HNSCSRNLYVSLMLLYKTYG  WKLHLYSHPIILGFRKIPMG  VGLSPFLLAQFTSAICSVVR
48  HNSCSRNLYVSIMLLYKTYG  WKLHLYSHPIILGFRKIPMG  VGLSPFLLAQFTSAICSVVR
49  HDSCSRNLYVSIMLLYKTYG  RKLHLYSHPIILGFRKIPMG  VGLSPFLLAQFTSAICSVVR
50  HDSCSRNLYVSLMLLYKTYG  RKLHLYSHPIILGFRKIPMG  VGLSPFLLAQFTSAICSVVR
51  HDSCSRQLYVSIMLLYKTYG  WKLHLYSHPIVLGFRKIPMG  VGLSPFLLAQFTSAICSVVR
52  HDSCSRQLYVSIMLLYKTYG  WKLHLYSHPIVLGFRKIPMG  VGLSPFLLAQFTSAICSVVR
53  HDYCSRNLYVSLLLLYKTFG  RKLHLYSHPIILGFRKIPMG  VGLSPFLLAQFTSAICSVVR
54  HDSCSRNLYVSLLLLYKTFG  RKLHLYSHPIILGFRKIPMG  VGLSPFLLAQFTSAICSVVR
55  HDSCSRNLYVSLLLLYQTFG  RKLHLYSHPIILGFRKIPMG  VGLSPFLLAQFTSAICSVVR
56  HDSCSRQLYVSIMLLYQNFG  WKLHLYSHPIVLGFRKIPMG  VGLSPFLLAQFTSAICSVVR
57  HDSCSRNLYVSLLLLYQTFG  RKLHLYSHPIILGFRKIPMG  vGLSPFLLAQFTSAICSVVR
58  HDSCSRNLYVSLLLLYKTFG  rKLHLYSHPIilGFRKIPMG  vGLSPFLLAQFTSAICSVVR
158
```

FIG. 4J

```
     541
39   RAFPHCLAFSYMDDVVLGAK  SVQHLESLFTSITNFLLSLG  IHLNPNKTKRWGYSLNFMGY
40   RAFPHCLAFSYMDDVVLGAK  SVQHLESLFTSITNFLLSLG  IHLNPNKTKRWGYSLNFMGY
41   RAFPHCLAFSYMDDVVLGAK  SVQHLESLFTSITNFLLSLG  IHLNPHKTKRWGYSLNFMGY
42   RAFPHCLAFSYMDDVVLGAK  SVQHLESLFTSITNFLLSLG  IHLNPNKTKRWGYSLNFMGY
43   RAFPHCLAFSYMDDVVLGAK  SVQHLESLFTSITNFLLSLG  IHLNPNKTKRWGYSLNFMGY
44   RAFPHCLAFSYMDDVVLGAK  SVQHLESLFTSITNFLLSLG  IHLNPNKTKRWGYSLNFMGY
45   RAFPHCLAFSYMDDVVLGAK  SVQHLESLFTSITNFLLSLG  IHLNPNKTKRWGYSLNFMGY
47   RAFPHCLAFSYMDDMVLGAK  SVQHLESLYAAVTNFLLSLG  IHLNPNKTKRWGYSLNFMGY
48   RAFPHCLAFSYMDDVVLGAK  SVQHLESLYAAVTNFLLSLG  IHLNPHKTKRWGYSLNFMGY
49   RAFPHCLAFSYMDDVVLGAK  SVQHLESLYAAVTNFLLSLG  IHLNPQKTKRWGYSLNFMGY
50   RAFPHCLAFSYMDDVVLGAK  SVQHREFLYTAVTNFLLSLG  IHLNPQKTKRWGYSLNFMGY
51   RAFPHCLAFSYMDDVVLGAK  SVQHRESLYTAVTNFLLSLG  IHLNPNKTKRWGYSLNFMGY
52   RAFPHCLAFSYMDDVVLGAK  SVQHLESLFTSITNFLLSLG  IHLNPNKTKRWGYSLNFMGY
53   RAFPHCLAFSYMDDVVLGAK  SVQHLESLFTAVTNFLLSLG  IHLNPNKTKRWGYSLNFMGY
54   RAFPHCLAFSYMDDVVLGAK  SVQHLESLFTAVTNFLLSLG  IHLNPNKTKRWGYSLNFMGY
55   RAFPHCLAFSYMDDVVLGAK  SVQHLESLFTAVTNFLLSLG  IHLNPNKTKRWGYSLHFMGY
56   RAFPHCLAFSYMDDVVLGAK  SVQHLESLFTAVTNFLLSLG  IHLNPNKTKRWGYSLNFMGY
57   RAFPHCLAFSYMDDVVLGAK  SVQHLESLFTAVTNFLLSLG  IHLNPNKTKRWGYSLNFMGY
58   RAFPHCLAFSYMDDvVLGAK  SVQHlesLftavTNFLLSLG  IHLNPnKTKRWGYSLnFMGY
158  RAFPHCLAFSYMDDvVLGAK  SVQH1esLftavTNFLLSLG  IHLNPnKTKRWGYSLnFMGY
```

FIG. 4K

```
    601
39  VIGSWGTLPQEHIVLKLKQC  FRKLPVNSPIDWKVCQRIVG  LLGFAAPFTQCGYPALMPLY
40  VIGCWGTLPQEHIVLKLKQC  FRKLPVNRPIDWKVCQRIVG  LLGFAAPFTQCGYPALMPLY
41  VIGSWGTLPQEHIVLKLKQC  FRKLPVNRPIDWKVCQRIVG  LLGFAAPFTQCGYPALMPLY
42  VIGCWGTLPQEHIVLKIKQC  FRKLPVNRPIDWKVCQRIVG  LLGFAAPFTQCGYPALMPLY
43  VIGSWGTLPQEHIVLKIKQC  FRKLPVNRPIDWKVCQRIVG  LLGFAAPFTQCGYPALMPLY
44  VIGCWGTLPQEHIVLKIKQC  FRKLPVNRPIDWKVCQRIVG  LLGFAAPFTQCGYPALMPLY
45  VIGSWGTLPQEHIVLKIKQC  FRKLPVNRPIDWKVCQRIVG  LLGFAAPFTQCGYPALMPLY
47  VIGSWGTWPQDHIVQNFKLC  FRKLPVNRPIDWKVCQRIVG  LLGFAAPFTQCGYPALMPLY
48  VIGSWGTLPQEHIVQKIKMW  FRKLPVNRPIDWKVCQRIVG  LLGFAAPFTQCGYPALMPLY
49  VIGSWGTLPQEHIVLKIKQC  FRKLPVNRPIDWKVCQRIVG  LLGFAAPFTQCGYPALMPLY
50  VIGSWGTLPQEHIVLKLKQC  FRKLPVNRPIDWKVCQRIVG  LLGFAAPFTQCGYPALMPLY
51  IIGSWGTLPQDHIVQKIKHC  FRKLPVNRPIDWKVCQRIVG  LLGFAAPFTQCGYPALMPLY
52  VIGSWGTLPQDHIVQKIKHC  FRKLPVNRPIDWKVCQRIVG  LLGFAAPFTQCGYPALMPLY
53  VIGCYGSLPQEHIIQKIKEC  FRKLPINRPIDWKVCQRIVG  LLGFAAPFTQCGYPALMPLY
54  VIGCYGSLPQEHIIQKIKEC  FRKLPVNRPIDWKVCQRIVG  LLGFAAPFTQCGYPALMPLY
55  VIGCYGSLPQEHIIQKIKEC  FRKLPVNRPIDWKVCQRIVG  LLGFAAPFTQCGYPALMPLY
56  VIGCYGSLPQDHIVQKIKEC  FRKVPVNRPIDWKVCQRIVG  LLGFAAPFTQCGYPALMPLY
57  VIGCYGSLPQDHIVQKIKEC  FRKVPVNRPIDWKVCQRIVG  LLGFAAPFTQCGYPALMPLY
58  IIGSWGTLPQDHIVQKIKEC  FRKLPVNRPIDWKVCQRIVG  LLGFAAPFTQCGYPALMPLY
158 vIGswGtlPQeHIvqkikQc  FRKlpvNrPIDWKVCQRIVG  LLGFAAPFTQCGYPALMPLY
```

FIG. 4L

```
     661
 39  ACIQSKQAFTFSPTYKAFLC  KQYLNLYPVARQRSGLCQVF  ADATPTGWGLAIGHRRMRGT
 40  ACIQSKQAFTFSPTYKAFLC  KQYLNLYPVARQRSGLCQVF  ADATPTGWGLAIGHRRMRGT
 41  ACIQSKQAFTFSPTYKAFLC  QQYLHLYPVARQRSGLCQVF  ADATPTGWGLAIGHRRMRGT
 42  ACIQSKQAFTFSPTYKAFLC  KQYLHLYPVARQRSGLCQVF  ADATPTGWGLAIGQSRMRGT
 43  ACIQSKQAFTFSPTYKAFLC  KQYLNLYPVARQRSGLCQVF  ADATPTGWGLAIGHSRMRGP
 44  ACIQSKQAFTFSPTYKAFLC  KQYLHLYPVARQRSGLCQVF  ADATPTGWGLAIGHRRMRGT
 45  ACIQSKQAFTFSPTYKAFLC  KQYLHLYPVAR-RTALCQVF  ADATPTGWGLAIGHRRMRGT
 46  ACIQSKQAFTFSPTYKAFLC  KQYLHLYPVAR-RTALCQVF  ADATPTGWGLAIGHRRMRGT
 47  ACIQAKQAFTFSPTYKAFLC  KQYMTLYPVARQRPGLCQVF  ADATPTGWGLAIGHQRMRGT
 48  ACIQAKQAFTFSPTYKAFLS  KQYLNLYPVARQRPGLCQVF  ADATPTGWGLAIGHQRMRGT
 49  ACIQAKQAFTFSPTYKAFLT  KQYLNLYPVARQRPGLCQVF  ADATPTGWGLAIGHQRMRGT
 50  ACIQAKQAFTFSPTYKAFLN  KQYMNLYPVARQRPGLCQVF  ADATPTGWGLAIGHQRMRGT
 51  ACIQAKQAFTFSPTYKAFLS  KQYMNLYPVARQRSGLCQVF  ADATPTGWGLAIGHRRMRGT
 52  ACIQSKQAFTFSPTYKAFLC  KQYLNLYPVARQRPGLCQVF  ADATPTGWGLAIGHRRMRGT
 53  ACIQSKQAFTFSPTYKAFLC  KQYLNLYPVARQRPGLCQVF  ADATPTGWGLVMGHQRMRGT
 54  ACIQSKQAFTFSPTYKAFLC  KQYLNLYPVARQRPGLCQVF  ADATPTGWGLVMGHQRMRGT
 55  ACIQSKQAFTFSPTYKAFLC  KQYLNLYPVARQRPGLCQVF  ADATPTGWGLAMGHQRMRGT
 56  ACIQFKQAFTFSPTYKAFLC  KQYLNLYPVAGQRPGLCQVF  ADATPTGWGLGMGHQRMRGT
 57  ACIQAKQAFTFSPTYKAFLS  KQYLNLYPVARQRPGLCQVF  ADATPTGWGLAIGNQRMRGT
 58  ACIQSKQAFTFSPTYKAFLC  KQYLNLYPVARQRPGLCQVF  ADATPTGWGLAIGHQRMRGT
158  ACIqsKQAFTFSPTYKAFLc  kQYlnLypVArQRpgLCQVF  ADATPTGWGLaiGhqrMRGt
```

FIG. 4M

```
     721
39   FVAPLPIHTAELLAACFARS   RSGAKLIGTDNSVVLSRKYT   SFPWLLGCAANWILRGTSFV
40   FVAPLPIHTAELLAACFARS   RSGAKLIGTDNSVVLSRKYT   SFPWLLGCAANWILRGTSFV
41   FVVPLPIHTAELLAACFARD   RSGAKLIGTDNSVVLSRKYT   SFPWLLGCAANWILRGTSFV
42   FVAPLPIHTAELLAACFARD   RSGAKLIGTDNSVVLSRKYT   SFPWLLGCAANWILRGTSFV
43   LWLLCRSILRNS
44   FVAPLPIHTAELLAACFARS   RSGAKLIGTDNSVVLSRKYT   SFPWLLGCAANWILRGTYFV
45   FVAPLPIHTAELLAACFARS   RSGANLIGTDNSVVLSRKYT   SFPWLLGCAANWILRGTYFV
47   FVSPLPIHTAELLAACFARS   RSGAKLIGTDNSVVLSRKYT   SFPWLLGCAANWILRGTSFV
48   FVSPLPIHTAELLAACFARS   RSGAKLIGTDNSVVLSRKYT   SFPWLLGCAANWILRGTSFV
49   FVSPLPIHTVELLAACFARS   RSGAKLIGTDNSVVLSRKYT   SFPWLLGCAANWILRGTSFV
50   FVSPLPIHTAELLAACFARS   RSGAKLIGTDNSVVLSRKYT   SFPWLLGCAANWILRGTSFV
51   FVAPLPIHTAELLAACFARS   RSGAKLIGTDNSVVLSRKYT   SFPWLLGCTANWILRGTSFV
52   FVAPLPIHTAELLAACFARS   RSGAKLIGTDNSVVLSRKYT   SFPWLLGCAANWILRGTSFV
53   FVAPLPIHTAELLAACFARS   RSGAKLIGTDNSVVLSRKYT   SFPWLLGCAANWILRGTSFV
54   FSAPLPIHTAELLAACFARS   RSGANIGTDNSVVLSRKYT    SFPWLLGCAANWILRGTSFV
55   FLARLPIHTAELLAACFARS   RSGANIGTDNSVVLSRKYT    SYPWLLGCAANWILRGTSFV
56   FSAPLPIHTAELLAACFARS   RSGANILGTDNSVVLSRKYT   SFPWLLGCAANWILRGTSFV
57   FSAPLPIHTAELLAACFARS   RSGANILGTDNSVVLSRKYT   SFPWLLGCTANWILRGTSFV
58   IVAPLPIHTAELLAACFARS   RSGAKLIGTDNSVVLSRKYT   SFPWLLGCAANWILRGTSFV
158  fvaplpihtaellAACFARs   RSGAkliGTDNSVVLSRKYT   SfpWLLGCAaNWILRGTSFV
```

FIG. 4N

```
    781
39  YVPSALNPADDPSRGRLGLY  RPLLLLPFRPTTGRTSLYAV  SPSVPSHLPDRVHFASPLHV
40  YVPSALNPADDPSRGRLGLY  RPLLHLPFRPTTGRTSLYAV  SPSVPSHLPDRVHFPSPLHV
41  YVPSALNPADDPSRGRLGLY  RPLLSLPFQPTTGRTSLYAV  SPSVPSHLPVRVHFASPLHV
42  YVPSALNPADDPSRGRLGLY  RPLLHLPFRPTTGRASLYAV  SPSVPSHLPDRVHFASPLHV
43  YVPSALNPADDPSRGRLGLY  RPLLHLRFRPTTGRTSLYAV  SPSVPSHLPDRVHFASPLHV
44  YVPSALNPADDPSRGRLGLI  RPLLHLPFRPTTGRTSLYAV  SPSVPSHLPDRVHFASPLHV
45  YVPSALNPADDPSRGRLGLI  RPLLHLRFRPTTGRTSLYAV  SPSVPSHLPDRVHFASPLHV
46  YVPSALNPADDPSRGRLGLY  RPLLRLPYRPTTGRTSLYAD  SPSVPSHLPDRVHFASPLHV
47  YVPSALNPADDPSRGRLGLY  RPLLRLLYRPTTGRTSLYAD  SPSVPSHLPDRVHFASPLHV
48  YVPSALNPADDPSRGRLGLY  RPLLRLPYRPTTGRTSLYAD  SPSVPSRLPDRVHFASPLHV
49  YVPSALNPADDPSRGRLGLY  RPLLRLPYRPTTGRTSLYAV  SPSVPSHLPVRVHFASPLHV
50  YVPSALNPADDPSRGRLGLY  RPLLRLRLPPTTGRTSLYAV  SPSVPSHLPDRVHFASPLHV
51  YVPSALNPADDPSRGRLGLS  RPLLRLPFQPTTGRTSLYAV  SPSVPSHLPDRVHFASPLHV
52  YVPSALNPADDPSRGRLGLS  RPLLRLPFRPTTGRTSLYAD  SPSVPSHLPDRVHFASPLHV
53  YVPSALNPADDPSRGRLGLY  RPLLHLPFRPTTGRTSLYAV  SPSVPSHLPDRVHFASPLHV
54  YVPSALNPADDPSRGRLGLS  RPLLRLPFRPTTGRTSLYAV  SPSVPSHLPDRVHFASPLHV
55  YVPSALNPADDPSRGRLGLS  RPLLRLPFRPTTGRTSLYAD  SPSVPSHLPDLVHFASPLHV
56  YVPSALNPADDPSRGRLGLS  RPLLRLPFRPTTGRTSLYAD  SPSVPSHLPDRVHFASPLHV
57  YVPSALNPADDPSRGRLGLS  RPLLCLPFRPTTGRTSLYAD  SPSVPSHLPVRVHFASPLHV
58  YVPSALNPADDPSRGRLGLS  RPLLRLPFQPTTGRTSLYAV  SPSVPSHLPVRVHFASPLHI
    158
    YVPSALNPADDPSRGRLGLy  RPLLrLpfrPTTGRtSLYAV  SPSVPShLPdrVHFaSPLHv
```

FIG. 40

| 841 | AWRPP | 39 |
| | AWRPP | 40 |
| | AWRPP | 41 |
| | AWRPP | 42 |
| | AWRPP | 44 |
| | AWRPP | 45 |
| | AWRPP | 47 |
| | AWRPP | 48 |
| | AWRPP | 49 |
| | AWRPP | 50 |
| | AWRPP | 51 |
| | AWRPP | 52 |
| | AWRPP | 53 |
| | AWRPP | 54 |
| | AWRPP | 55 |
| | AWRPP | 56 |
| | AWRPP | 57 |
| | AWRPP | 58 |
| | AWRPP | 158 |

PEPTIDE SPECIFICITY

1 POL455-463
2 POL551-559
3 POL575-583
4 POL655-663
5 POL773-782
6 POL816-824
7 CORE18-27
8 ENV335-343

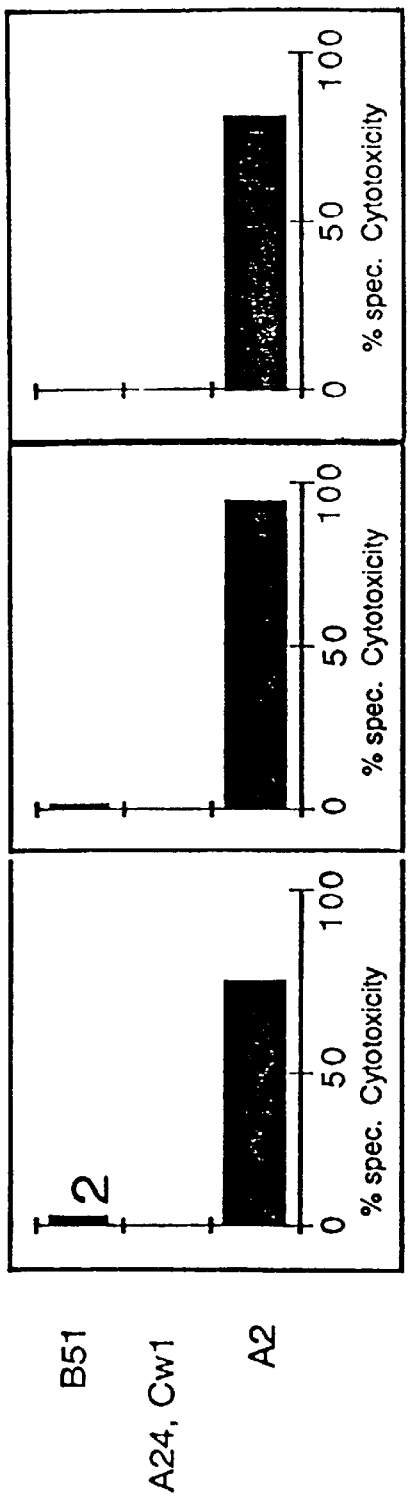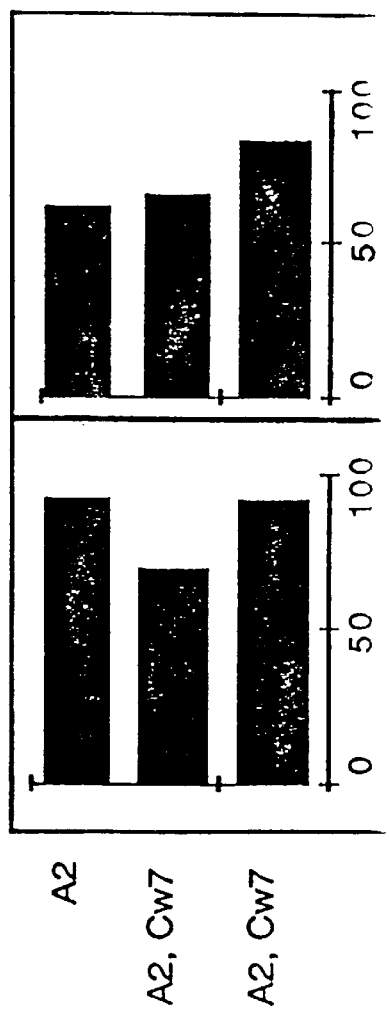
FIG. 8

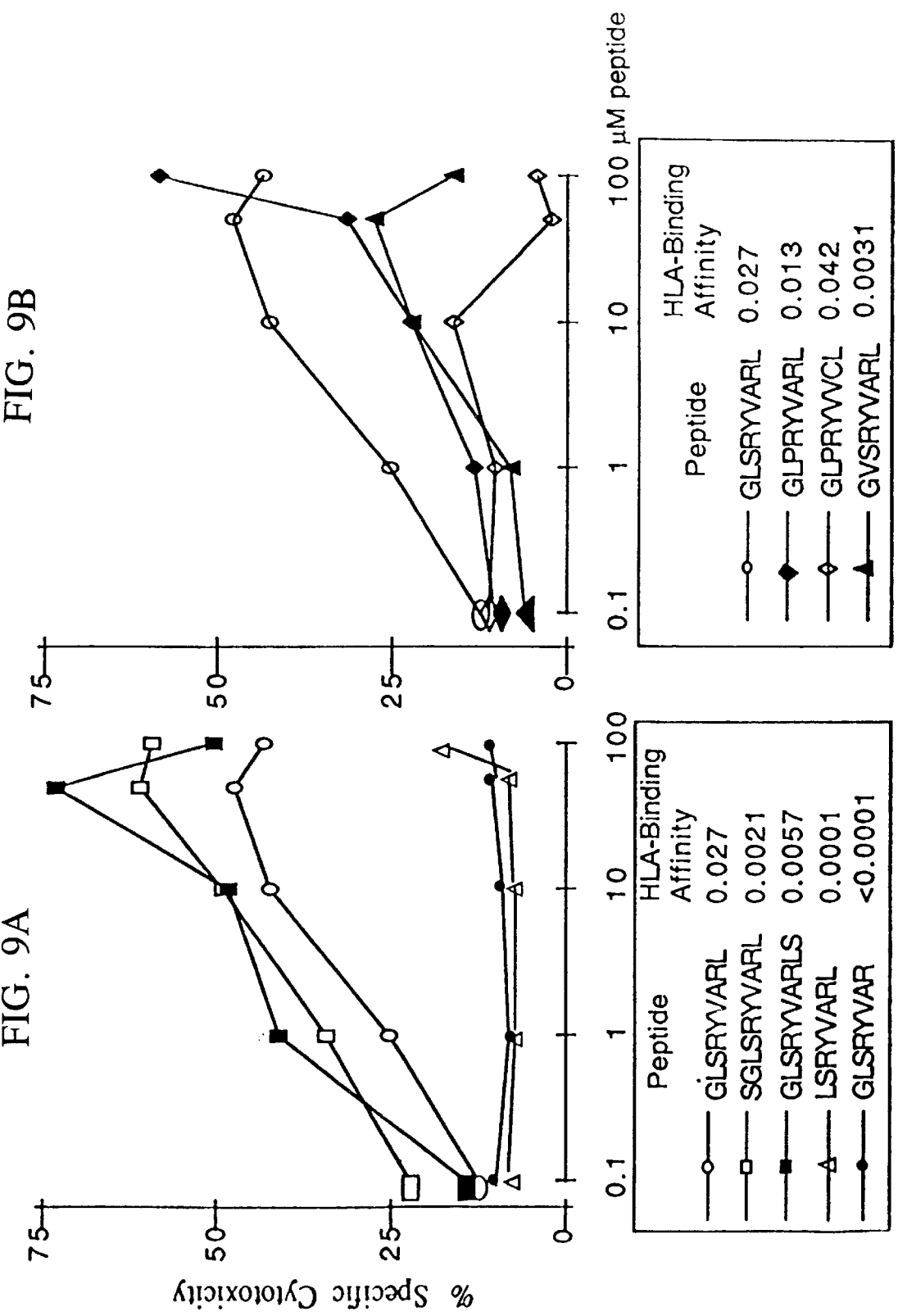

PEPTIDES FOR INDUCING CYTOTOXIC T LYMPHOCYTE RESPONSES TO HEPATITUS B VIRUS

RELATED APPLICATIONS

The present application is filed as a 35 U.S.C. §371 application of PCT international application PCT/US94/08685, filed Aug. 1, 1994, which is a continuation-in-part application of U.S. Ser. No. 08/100,870, filed Aug. 2, 1993 (now abandoned), which is a continuation-in-part of U.S. Ser. No. 07/935,898 filed Aug. 26, 1992 (now abandoned), which is a continuation-in-part of U.S. Ser. No. 07/749,540 filed Aug. 26, 1991 (now abandoned), the disclosures of which are incorporated herein by reference.

GOVERNMENT SUPPORT

This invention was made with government support under Contract No. AI 20001 by the National Institutes of Health. The government has certain rights in this invention.

BACKGROUND OF THE INVENTION

Cytotoxic T lymphocytes (CTLs) play an essential role in fighting cells infected with viruses, intracellular bacteria and parasites, and tumor cells. They do so by direct cytotoxicity and by providing specific and nonspecific help to other immunocytes such as macrophages, B cells, and other T cells. Infected cells or tumor cells process antigen through intracellular events involving proteases. The processed antigen is presented on the cellular surface in the form of peptides bound to HLA class I molecules to T cell receptors on CTLs. MHC class I molecules can also bind exogenous peptides and present them to CTLs without intracellular processing.

At the present time it is difficult to accurately predict from the sequence of an antigenic protein how the protein will be processed and which peptide portions will bind HLA class I molecules and be presented to CTLs. Binding motifs have been predicted for some HLA class I molecules based on sequence analysis of peptides eluted from these molecules (Falk et al., *Nature* 351:290 (1991)). Further, of the peptides that are processed and do bind to HLA class I, which ones will contain CTL-recognizable epitopes is not yet predictable.

Hepatitis B Virus ("HBV") is a non-lytic virus which has currently infected approximately 250 million people worldwide. HBV infection in adults typically leads to an acute disease in the majority of cases, and to a chronic disease state in a minority of patients. This ratio of acute to chronic is reversed when the infection occurs close to the time of birth. There is an increased incidence of hepatocellular carcinoma in chronic HBV infection. A small percentage of individuals who are infected with HBV in adulthood develop fulminant hepatitis associated with a strong immune response with high lethality.

While there is no effective treatment for HBV infection, vaccines have been developed in recent years to prevent HBV infection. The vaccines employ either HBV surface antigen (HBsAg) purified from the plasma of chronic HBV carriers, or HBsAg produced by recombinant DNA technology. Synthetic HBsAg peptide-based vaccines have also been proposed. See, for example, U.S. Pat. Nos. 4,599,230 and 4,599,231. The anti-HBsAg vaccines, however, afford protection in only about 90% of immunized individuals. Those who are unimmunized, or immunized but unprotected, provide a significant reservoir of potential infection.

The contribution of CTLs to immunity to HBV antigens has been difficult to assess. Chisari et al. (*Microbial Pathogen.* 6:31 (1989)) have suggested that liver cell injury may be mediated by an HLA-Class I restricted, $CD8^+$ cytotoxic T cell response to HBV encoded antigens. Class I major histocompatibility (MHC)-restricted cytotoxic T lymphocyte responses have been identified for a variety of other viruses, such as influenza. For example, Townsend et al., *Cell* 44:959 (1986) reported that epitopes of an influenza virus nucleoprotein recognized by cytotoxic T lymphocytes could be defined by synthetic peptides. In attempting to define the cytotoxic T lymphocyte response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). Moriyama et al., *Science* 248:361–364 (1990), have reported that the HBV major envelope antigen is expressed at the hepatocyte surface in a form recognizable by envelope-specific antibodies and by MHC class I-restricted, $CD8^+$ cytotoxic T lymphocytes.

As there is a large reservoir of individuals chronically infected with HBV, it would be desirable to stimulate the immune response of these individuals to respond to appropriate HBV antigens and thereby eliminate their infection. It would also be desirable to prevent the evolution to a chronic HBV infection in individuals suffering from an acute phase infection. Further, as the presently approved HBV vaccines do not elicit protective immunity in about 10% of immunized individuals, it would be desirable to elicit more effective immunity, such as by increasing or diversifying the immunogenicity of the vaccines. Quite surprisingly, the present invention fulfills these and other related needs.

SUMMARY OF THE INVENTION

The present invention provides peptides which induce MHC class I restricted cytotoxic T lymphocyte responses against HBV antigen. The peptides of interest are derived from the sequence of the HBV polymerase protein. In certain embodiments the CTL inducing peptide will have the sequence of HBpol4–13 (Ser-Tyr-Gln-His-Phe-Arg-Lys-Leu-Leu-Leu) [Seq ID No. 12]; HBpol61–69 (Gly-Leu-Tyr-Ser-Ser-Thr-Val-Pro-Val) [Seq ID No. 1]; HBpol108–116 (Arg-Leu-Lys-Leu-Ile-Met-Pro-Ala-Arg) [Seq ID No. 13]; HBpol139–147 (Val-Val-Asn-His-Tyr-Phe-Gln-Thr-Arg) [Seq ID No. 14]; HBpol151–160 (His-Thr-Leu-Trp-Lys-Ala-Gly-Ile-Leu-Tyr) [Seq ID No. 15]; HBpol152–161 (Thr-Leu-Trp-Lys-Ala-Gly-Ile-Leu-Tyr-Lys) [Seq ID No. 16]; HBpol455–463 (Gly-Leu-Ser-Arg-Tyr-Val-Ala-Arg-Leu) [Seq ID No. 2]; HBpol505–514 (Leu-Tyr-Ser-His-Pro-Ile-Ile-Leu-Gly-Phe) [Seq ID No. 17]; HBpol551–559 (Tyr-Met-Asp-Asp-Val-Val-Leu-Gly-Ala) [Seq ID No. 18]; HBpol575–583 (Phe-Leu-Leu-Ser-Leu-Gly-Ile-His-Leu) [Seq ID No. 19]; HBpol655–663 (Ala-Leu-Met-Pro-Leu-Tyr-Ala-Cys-Ile) [Seq ID No. 20]; HBpol748–757 (Gly-Thr-Asp-Asn-Ser-Val-Val-Leu-Ser-Arg) [Seq ID No. 21]; HBpol758–766 (Lys-Tyr-Thr-Ser-Phe-Pro-Trp-Leu-Leu) [Seq ID No. 22]; HBpol773–782 (Ile-Leu-Arg-Gly-Thr-Ser-Phe-Val-Tyr-Val) [Seq ID No. 3]; HBpol803–811 (Ser-Leu-Tyr-Ala-Asp-Ser-Pro-Ser-Val) [Seq ID No. 4]; and HBpol816–824 (Phe-Leu-Leu-Ser-Leu-Gly-Ile-His-Leu) [Seq ID No. 5]; or will have a sequence substantially homologous to one of the foregoing sequences. The peptide can be optionally flanked and/or modified at one or both of the N-and C-termini, as desired. Conservative substitutions, deletions and additions may be made at non-critical residue positions within the selected peptide without substantially adversely affecting its biological activity.

The present invention provides peptides which induce MHC Class I restricted cytotoxic T lymphocyte responses against HBV antigen. The peptides of interest are derived from the HBV nucleocapsid. In certain embodiments the peptides comprises from six to about fifty amino acids and have at least four contiguous amino acids from within the sequence ($HBc_{19-27}$) Leu-Pro-Ser-Asp-Phe-Phe-Pro-Ser-Val, [SEQ ID NO:68] wherein the peptide can be optionally flanked and/or modified at one or both of the N- and C-termini, as desired. In preferred embodiments the peptide sequences are Ala-Thr-Val-Glu-Leu-Leu-Ser-Phe-Leu-Pro-Ser-Asp-Phe-Phe-Pro-Ser-Val, ($HBc_{11-27}$) [SEQ ID NO:67], and Leu-Pro-Ser-Asp-Phe-Phe-Pro-Ser-Val ($HBc_{19-27}$) [SEQ ID NO:68], which regions are conserved among the major subtypes of HBV, although substitutions, deletions and additions may be made to the peptide without substantially adversely affecting its biological activity.

In other embodiments the peptides are from six to about fifty amino acids and have at least four contiguous residues from with the sequence ($HBc_{140-154}$) Leu-Ser-Thr-Leu-Pro-Glu-Thr-Thr-Val-Val-Arg-Arg-Arg-Gly-Arg [SEQ ID NO:71], wherein the peptide can be optionally flanked and/or modified at one or both of the N- and C-termini, as desired. In other embodiments the peptides are derived from at least seven contiguous amino acids of the sequence of $HBc_{111-125}$, wherein $HBc_{111-125}$ for HBV subtype awy has the sequence Gly-Arg-Glu-Thr-Val-Ile-Glu-Tyr-Leu-Val-Ser-Phe-Gly-Val-Trp [SEQ ID NO:70], wherein termini may be also modified as mentioned above. For the HBV subtype adw, the $Ile_{116}$ is replaced by Leu. In yet another embodiment a peptide which induces a MHC Class I-restricted cytotoxic T lymphocyte response is peptide ($HB_{c28-47}$) [SEQ ID NO:72] having the sequence Arg-Asp-Leu-Leu-Asp-Thr-Ala-Ser-Ala-Leu-Tyr-Arg-Glu-Ala-Leu-Glu-Ser-Pro-Glu-His, wherein termini of the selected peptide can also be modified, as desired.

In the various peptide embodiments it will be understood that the peptides can be polymerized, each to itself to form larger homopolymers, or with different peptides to form heteropolymers. In some instances peptides will be combined in a composition as an admixture and will not be linked. The peptide can also be conjugated to a lipid-containing molecules capable of enhancing a T lymphocyte response, or to a different peptide which induces a T-helper cell response, for example.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective cytotoxic T cell responses against HBpol epitopes. For treating these infections it may be particularly desirable to combine the peptides which induce MHC class I restricted cytotoxic T lymphocyte responses against HBV antigen with other peptides or proteins that induce immune response to other HBV antigens, such as HBV envelope or core. To treat individuals with chronic or carrier state infections the compositions may be administered in repeated dosages over a prolonged period of time, as necessary, to resolve or substantially mitigate the infection and/or shedding of virus.

Vaccine compositions for preventing HBV infection, particularly chronic HBV infection, are also provided. The vaccine compositions comprise an immunogenically effective amount of a HBV polymerase peptide mentioned above which induces a MHC class I restricted cytotoxic T lymphocyte response, such as HLA-A2, -A1, -A3, A-11, and/or -A24, and will typically further comprise an adjuvant, e.g., incomplete Freund's adjuvant or aluminum hydroxide. To achieve enhanced protection against HBV, the vaccine can further comprise components which elicit a protective antibody response to other HBV antigen, such as envelope (surface) antigen.

In yet other embodiments the invention relates to methods for diagnosis, where the peptides of the invention are used to determine the presence of lymphocytes in an individual which are capable of a cytotoxic T cell response to HBV polymerase antigen. The absence of such cells determines whether the individual of interest is susceptible to developing chronic HBV infection. Typically the lymphocytes are peripheral blood lymphocytes and the individual of interest is suffering from an acute HBV infection.

BRIEF DESCRIPTION OF THE DRAWINGS

FIGS. 3A and 3B shows that the CTL response to polymerase peptide 803–811 can recognize cells pulsed with peptide and endogenously synthesized polymerase (Vpol), whereas the CTL response to polymerase peptide 61–69 only recognized cells pulsed with the 61–69 peptide.

FIG. 4 shows the aligned amino acid sequences of 20 cloned HBV polymerase proteins (SEQ ID NOS:45–64); line 158 is a consensus sequence (SEQ ID NO:11) where capital letters represent 100% consensus, lower case letters represent >50% consensus, and "." is <50% consensus.

FIG. 8 shows HLA-restriction of epitope Pol455–463. Pol455–463-specific lines from patient A-1 and A-2, generated by stimulation with Pol455–463 peptide, were tested against allogeneic partly HLA-matched EBV-B cells prepulsed overnight with 10 μg/ml of the same peptide. Sharing HLA class I at other loci did not render target cells susceptible to lysis. Cytotoxicity was measured at E:T of 50:1 in a 4 hr $^{51}$Cr-release assay.

FIGS. 9A and B shows recognition of truncated, elongated (SEQ ID NOS:2,39,40,65 and 66) (a) or variant peptides (SEQ ID NOS:2,38,43, and 41, respectively) (b) by Pol455–463 specific CTL-lines, generated by weekly stimulation of PBMC from patient A-1 with peptide Pol455–463 for 4 weeks. Cytotoxicity was measured at E:T of 50:1 in a 4 hr $^{51}$Cr-release assay against JY-EBV cells prepulsed with varying amounts of the same peptide overnight.

DESCRIPTION OF THE SPECIFIC EMBODIMENTS

Figure 1:
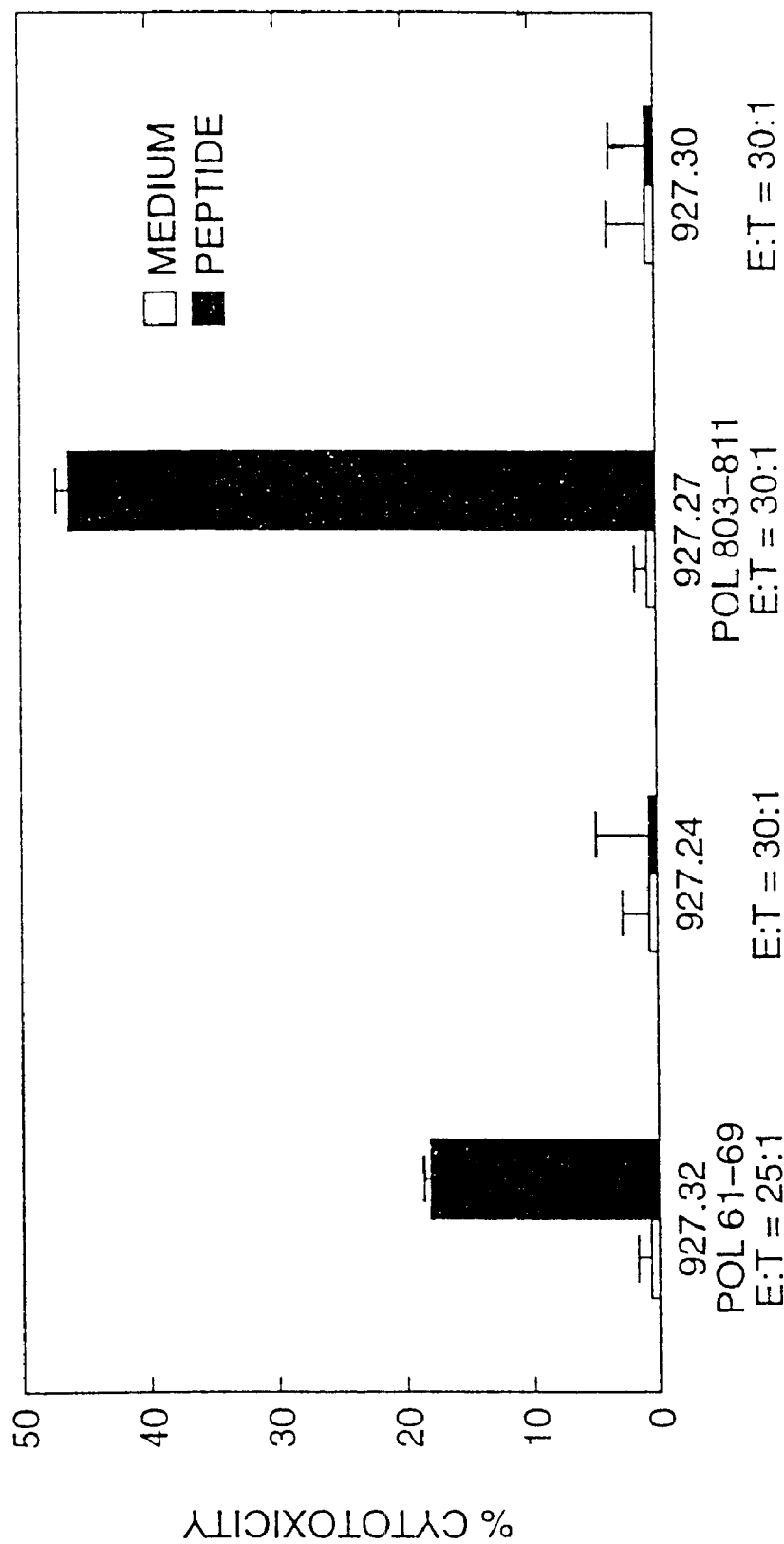
FIG. 1 shows the CTL response to two polymerase peptides that contain the HLA-A2 motif in a patient using target cells pulsed with peptide that match only at HLA-A2.

The present invention provides peptides derived from HBV polymerase proteins for use in compositions and methods for the treatment, prevention and diagnosis of HBV infection. The peptides stimulate MHC HLA-class I restricted cytotoxic T lymphocyte responses against HBV infected cells. The stimulated cytotoxic T lymphocytes are able to kill the infected cells or inhibit viral replication and thus interrupt or substantially prevent infection, including chronic HBV infection. A peptide effective in eliciting a cytotoxic T cell response may also be combined with an immunogen capable of eliciting a T-helper response.

The peptides employed in the invention are derived from the sequence of the HBV polymerase protein (HBpol), particularly CTL epitopes within HBpol4–13, HBpol61–69, HBpol108–116, HBpol139–147, HBpol151–160, HBpol152–161, HBpol455–463, HBpol505–514, HBpol551–559, HBpol575–583, HBpol655–663, HBpol748–757, HBpol758–766, HBpol773–782, HBpol803–811, or HBpol816–824, where the numbering is according to Galibert et al., supra.

By HBV cytotoxic T lymphocyte inducing "peptide" or "oligopeptide" of the present invention is meant a chain of at least four HBV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues derived from an HBc sequence. It may be desirable to optimize peptides of the invention to a length of eight to twelve amino acid residues, more preferably nine to eleven, commensurate in size with endogenously processed viral peptides that are bound to MHC class I molecules on the cell surface. See generally, Schumacher et al., *Nature* 350:703–706 (1991); Van Bleek et al., *Nature* 348:213–216 (1990); Rotzschke et al., *Nature* 348:252–254 (1990); and Falk et al., *Nature* 351:290–296 (1991), which are incorporated herein by reference. As set forth in more detail below, usually the peptides will have at least a majority of amino acids which are homologous to a corresponding portion of contiguous residues of the HBV pol sequences herein, and contain a CTL-inducing epitope.

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. By biological activity is meant the ability to bind an appropriate MHC molecule and induce a cytotoxic T lymphocyte response against HBV antigen or antigen mimetic. By a cytotoxic T lymphocyte response is meant a CD8$^+$ T lymphocyte response specific for an HBV antigen of interest, wherein CD8$^+$, MHC class I-restricted T lymphocytes are activated. The activated T lymphocytes secrete lymphokines (e.g., gamma interferon) liberate products (e.g., serine esterases) that inhibit viral replication in infected autologous cells or transfected cells, with or without cell killing.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

A CTL-inducing HBV peptide embodiment of the invention from the nucleocapsid region comprises from six to thirty-five amino acids and contains at least one HLA-restricted CTL epitopic site from the peptide region HBc$_{11-27}$. A majority of the amino acids of the peptide will be identical or substantially homologous to the amino acids of the corresponding portions of the naturally occurring HBc$_{11-27}$ region, where HBc$_{11-27}$ has the sequence:

I (HBc$_{11-27}$) (SEQ ID NO:67)

Ala-Thr-Val-Glu-Leu-Leu-Ser-Phe-Leu-Pro-Ser-Asp-Phe-Phe-Pro-Ser-Val.

The peptide embodiments of this HBc$_{11-27}$ region can be optionally flanked and/or modified at one or both of the N- and C-termini, as desired, by amino acids from HBV sequences, including HBc, amino acids added to facilitate linking, other N- and C-terminal modifications, linked to carriers, etc., as further described herein. The peptide HBc$_{11-27}$ induces a cytotoxic T lymphocyte response which is mediated by at least the MHC class I molecule HLA-A2.

Within the peptide I region are peptides which comprise the 9-mer peptide HBc$_{19-27}$ and contain a HLA-restricted CTL-inducing epitope, and peptides derived therefrom which contain a CTL-inducing epitopic site(s) of at least four contiguous amino acids of the sequence of HBc$_{19-27}$, wherein HBc$_{19-27}$ has the following sequence:

II (HBc$_{19-27}$) [[Seq. ID No. 4]] (SEQ ID NO:68)

Leu-Pro-Ser-Asp-Phe-Phe-Pro-Ser-Val, wherein the peptide can be flanked and/or modified at one or both termini as mentioned for peptide I above. As with peptide I, peptide II induces a cytotoxic T lymphocyte response which is mediated by at least HLA-A2.

A particularly preferred peptide embodiment in the peptide I/II region is a 10-mer, $HBc_{18-27}$, which has the following sequence:

III ($HBc_{18-27}$) [[Seq. ID No. 5]] (SEQ ID NO:69)

Phe-Leu-Pro-Ser-Asp-Phe-Phe-Pro-Ser-Val, wherein the peptide can be modified and/or flanked as previously mentioned.

Another HBc peptide embodiment of the invention comprises the 15-mer peptide $HBc_{111-125}$, and peptides derived from $HBc_{111-125}$ which contain a CTL-inducing HLA class I-restricted epitopic site(s) of at least seven contiguous amino acids. A majority of the amino acids of the peptide will be identical or substantially homologous to the amino acids of the corresponding portions of the naturally occurring $HBc_{111-125}$ sequence, where $HBc_{111-125}$ has the sequence (for HBV subtype ayw):

IV ($HBc_{111-125}$) [[Seq. ID No. 6]] (SEQ ID NO:70)

Gly-Arg-Glu-Thr-Val-Ile-Glu-Tyr-Leu-Val-Ser-Phe-Gly-Val-Trp.

The peptide from the $HBc_{111-125}$ region can be flanked and/or modified at one or both termini as described herein. In a peptide of the HBV subtype adw, $Ile_{116}$ is replaced by Leu.

In a further another embodiment, a peptide of the invention comprises the 15-mer peptide $HBc_{140-154}$, and peptides derived from $HBc_{140-154}$ which contain a CTL-inducing HLA class I-restricted epitopic site(s) of at least ten contiguous amino acids. A majority of the amino acids of the peptide will be identical or substantially homologous to the amino acids of the corresponding portions of the naturally occurring $HBc_{140-154}$ sequence, where $HBc_{140-154}$ has the sequence (for HBV subtype ayw):

V ($HBc_{140-154}$) [[Seq. ID No. 7]] (SEQ ID NO:71)

Leu-Ser-Thr-Leu-Pro-Glu-Thr-Thr-Val-Val-Arg-Arg-Arg-Gly-Arg

A peptide prepared from this region can be flanked and/or modified at one or both termini as described herein. The peptide V ($HBc_{140-154}$) induces a cytotoxic T lymphocyte response which is mediated by at least one MHC class I molecule, HLA-A31, and can also be restricted by HLA-Aw6S. As shown in more detail in the Example section below, the sequence of $HBc_{141-151}$ contains the minimal, optimally recognized epitope for both the A31 and Aw68 restriction elements.

Yet other CTL-inducing peptides of the invention are from the region of $HBc_{28-47}$, and includes peptides derived from $HBc_{28-47}$ which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBc_{28-47}$ sequence, where $HBc_{28-47}$ has the sequence (for HBV subtype ayw):

VI ($HBc_{28-47}$) [[Seq. ID No. 8]] (SEQ ID NO:72)

Arg-Asp-Leu-Leu-Asp-Thr-Ala-Ser-Ala-Leu-Tyr-Arg-Glu-Ala-Leu-Glu-Ser-Pro-Glu-His, wherein the selected peptide can be flanked and/or modified at one or both termini as described herein.

In other embodiments of the present invention, the peptides of the invention contain CTL-inducing epitopes derived from the polymerase protein. More particularly, the peptides are from the region of $HBpol_{61-69}$ or [$HBpol_{803-11}$] $HBpol_{803-811}$, and include peptides derived from those sequence regions which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBpol_{61-69}$ or $HBpol_{803-811}$ sequences, where $HBpol_{61-69}$ and $HBpol_{803-811}$ have the following sequences (for HBV subtype ayw):

VII ($HBpol_{61-69}$) [[Seq. ID No. 9]] (SEQ ID NO:1)

[Gly-Len-Tyr-Ser-Ser-Thr-Val-Pro-Val]

Gly-Leu-Tyr-Ser-Ser-Thr-Val-Pro-Val, and

VIII ($HBpol_{803-811}$) [[Seq. ID No. 10]] (SEQ ID NO:4)

Ser-Leu-Tyr-Ala-Asp-Ser-Pro-Ser-Val, wherein the selected peptide can be flanked and/or modified at one or both termini as described herein.

Peptides of the present invention which contain anti-HBV CTL-inducing epitopes are also derived from the HBV transcriptional activator protein [x] X. Although a variety of HBx peptides having CTL including activity can be identified as described herein, preferably, the peptides are from the region of $HBx_{126-134}$. Peptides derived from this sequence region contain one or more CTL-inducing ALA class I-restricted epitopic site(s) of at least seven contiguous amino acids. A majority of the amino acids of the peptide prepared from this region will be identical or substantially homologous to the amino acids of the corresponding portions of the naturally occurring $HBx_{126-134}$ sequence, where $HBx_{126-134}$ has the following sequence:

IX (HBx126-134) [[Seq. ID No. ]] (SEQ ID NO:73)

Glu-Ile-Arg-Leu-Lys-Val-Phe-Val-Leu wherein the peptide prepared from this region can be flanked and/or modified at one or both termini as described herein.

CTL-inducing peptides are also derived from the HBV envelope protein, and more particularly, the peptide is $HBenv_{348-357}$ and is HLA class I-restricted, where $HBenv_{348-357}$ has the following sequence (for subtype ayw):

X ($HBenv_{348-357}$) [[Seq. ID No. ]] (SEQ ID NO:74)

Gly-Leu-Ser-Pro-Thr-Val-Trp-Len-Ser-Val, wherein the peptide prepared from this region can be flanked and/or modified at one or both termini as described herein. The sequence for the adw subtype of $HBenv_{348-357}$ has an alanine substituted for valine at the carboxy terminal residue.

The peptides of the invention contain CTL-inducing epitopes derived from various epitopic regions of the HBV polymerase protein. The peptides are from the region of $HBpol_{61-69}$ and include peptides derived from those sequence regions which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBpol_{61-69}$ sequence, where $HBpol_{61-69}$ has the following sequence (for HBV subtype ayw):

($HBpol_{61-69}$) [Seq. ID No. 1]

Gly-Leu-Tyr-Ser-Ser-Thr-Val-Pro-Val, and

The peptide embodiments of this $HBpol_{61-69}$ region and the other polymerase peptide regions described herein can be optionally flanked and/or modified at one or both of the N- and C-termini, as desired, by amino acids from HBV sequences, including HBpol, amino acids added to facilitate linking, other N- and C-terminal modifications, linked to carriers, etc., as further described herein. The peptide HBpol61–69 induces a cytotoxic T lymphocyte response which is mediated by at least the MHC class I molecule HLA-A2.

Other HBpol region peptides containing CTL epitopes of the invention comprises the peptide HBpol 455–463, and peptides derived from HBpol455–463 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol455–463 sequence, where HBpol 455–463 has the sequence (for HBV subtype ayw):

(HBpol 455–463) [Seq ID No. 2]

Gly-Leu-Ser-Arg-Tyr-Val-Ala-Arg-Leu wherein the selected peptide can be flanked and/or modified at one or both termini as described herein. The peptide HBpol 455–463 induces a cytotoxic T lymphocyte response which is mediated by at least the MHC class I molecule HLA-A2.

Yet other HBpol region peptides containing CTL epitopes of the invention comprises the peptide HBpol 773–782, and peptides derived from HBpol773–782 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol 773–782 sequence, where HBpol 773–782 has the sequence (for HBV subtype ayw):

(HBpol 773–782) [Seq ID No. 3]

Ile-Leu-Arg-Gly-Thr-Ser-Phe-Val-Tyr-Val wherein the selected peptide can be flanked and/or modified at one or both termini as described herein. The peptide HBpol 773–782 induces a cytotoxic T lymphocyte response which is mediated by at least the MHC class I molecule HLA-A2. Other HBpol peptide embodiments of the invention are prepared from the region of HBpol803–811. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol803–811 sequence, where HBpol803–811 has the sequence (for HBV subtype ayw):

(HBpol$_{803-811}$) [Seq ID No. 4]

Ser-Leu-Tyr-Ala-Asp-Ser-Pro-Ser-Val, wherein the selected peptide can be flanked and/or modified at one or both termini as described herein. The peptide HBpol 803–811 induces a cytotoxic T lymphocyte response which is mediated by at least the MHC class I molecule HLA-A2.

Other HBpol peptide embodiments of the invention are prepared from the region of HBpol816–824. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol816–824 sequence, where HBpol816–824 has the sequence (for HBV subtype ayw):

(HBpol$_{816-824}$) [Seq ID No. 5]

Phe-Leu-Leu-Ser-Leu-Gly-Ile-His-Leu, wherein the selected peptide can be flanked and/or modified at one or both termini as described herein. The peptide HBpol 816–824 induces a cytotoxic T lymphocyte response which is mediated by at least the MHC class I molecule HLA-A2.

Other HBpol peptide embodiments of the invention are prepared from the regions of HBpol4–13, HBpol108–116, HBpol139–147, HBpol151–160, HBpol152–161, HBpol505–514, HBpol551–559, HBpol575–583, HBpol655–663, HBpol748–757, or HBpol758–766. A peptide prepared from one of the aforementioned regions contains at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol sequence, where the HBpol regions have the sequences (for HBV subtype ayw):

HBpol4–13 [Seq ID No. 12]
Ser-Tyr-Gln-His-Phe-Arg-Lys-Leu-Leu-Leu
HBpol108–116 [Seq ID No. 13]
Arg-Leu-Lys-Leu-Ile-Met-Pro-Ala-Arg
HBpol139–147 [Seq ID No. 14]
Val-Val-Asn-His-Tyr-Phe-Gln-Thr-Arg
HBpol151–160 [Seq ID No. 15]
His-Thr-Leu-Trp-Lys-Ala-Gly-Ile-Leu-Tyr
HBpol152–161 [Seq ID No. 16]
Thr-Leu-Trp-Lys-Ala-Gly-Ile-Leu-Tyr-Lys
HBpol505–514 [Seq ID No. 17]
Leu-Tyr-Ser-His-Pro-Ile-Ile-Leu-Gly-Phe
HBpol551–559 [Seq ID No. 18]
Tyr-Met-Asp-Asp-Val-Val-Leu-Gly-Ala
HBpol575–583 [Seq ID No. 19]
Phe-Leu-Leu-Ser-Leu-Gly-Ile-His-Leu
HBpol655–663 [Seq ID No. 20]
Ala-Leu-Met-Pro-Leu-Tyr-Ala-Cys-Ile
HBpol748–757 [Seq ID No. 21]
Gly-Thr-Asp-Asn-Ser-Val-Val-Leu-Ser-Arg
HBpol758–766 [Seq ID No. 22]
Lys-Tyr-Thr-Ser-Phe-Pro-Trp-Leu-Leu wherein the selected peptide can be flanked and/or modified at one or both termini as described herein. The peptide HBpol151–160 induces a CTL response which is mediated by at least the MHC class I molecule HLA-A1. The peptides HBpol551–559 and HBpol655–663 induce a CTL response which is mediated by at least the MHC class I molecule HLA-A2. The peptide HBpol575–583 induces a CTL response which is mediated by at least the MHC class I molecule HLA-A2.1. The peptides HBpol108–116, HBpol139–147, HBpol152–161, and HBpol748–757 induce a CTL response which is mediated by at least the MHC class I molecule HLA-A3 (HBpol748–757 appearing to also be restricted by A24). The peptides HBpol4–13, HBpol505–514, and HBpol758–766 induce CTL responses which are mediated by at least the MHC class I molecule HLA-A24.

As mentioned above, additional amino acids can be added to the termini of an oligopeptide or peptide to provide for ease of linking peptides one to another, for coupling to a carrier, support or a larger peptide, for reasons discussed herein, or for modifying the physical or chemical properties of the peptide or oligopeptide, and the like. Amino acids such as tyrosine, cysteine, lysine, glutamic or aspartic acid, and the like, can be introduced at the C- or N-terminus of the peptide or oligopeptide. In addition, the peptide or oligopeptide sequences can differ from the natural sequence by being modified by terminal-$NH_2$ acylation, e.g., acetylation, or thioglycolic acid amidation, terminal-carboxy amidation, e.g., ammonia, methylamine, etc. In some instances these modifications may provide sites for linking to a support or other molecule.

It will be understood that the HBV peptides of the present invention or analogs or homologs thereof which have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, e.g., the addition or deletion of amino acids on either the amino terminal or carboxy terminal end, or both, of peptides derived from the sequences disclosed herein. The peptides may be modified to substantially enhance the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

The peptides employed in the subject invention need not be identical to peptides HBpol4–13 (Ser-Tyr-Gln-His-Phe-Arg-Lys-Leu-Leu-Leu) [Seq ID No. 12]; HBpol61–69 (Gly-Leu-Tyr-Ser-Ser-Thr-Val-Pro-Val) [Seq ID No. 1]; HBpol108–116 (Arg-Leu-Lys-Leu-Ile-Met-Pro-Ala-Arg) [Seq ID No. 13]; HBpol139–147 (Val-Val-Asn-His-Tyr-Phe-Gln-Thr-Arg) [Seq ID No. 14]; HBpol151–160 (His-Thr-Leu-Trp-Lys-Ala-Gly-Ile-Leu-Tyr) [Seq ID No. 15]; HBpol152–161 (Thr-Leu-Trp-Lys-Ala-Gly-Ile-Leu-Tyr-Lys) [Seq ID No. 16]; HBpol455–463 (Gly-Leu-Ser-Arg-Tyr-Val-Ala-Arg-Leu) [Seq ID No. 2]; HBpol505–514 (Leu-Tyr-Ser-His-Pro-Ile-Ile-Leu-Gly-Phe) [Seq ID No. 17]; HBpol551–559 (Tyr-Met-Asp-Asp-Val-Val-Leu-Gly-Ala) [Seq ID No. 18]; HBpol575–583 (Phe-Leu-Leu-Ser-Leu-Gly-Ile-His-Leu) [Seq ID No. 19]; HBpol655–663 (Ala-Leu-Met-Pro-Leu-Tyr-Ala-Cys-Ile) [Seq ID No. 20]; HBpol748–757 (Gly-Thr-Asp-Asn-Ser-Val-Val-Leu-Ser-Arg) [Seq ID No. 21]; HBpol758–766 (Lys-Tyr-Thr-Ser-Phe-Pro-Trp-Leu-Leu) [Seq ID No. 22]; HBpol773–782 (Ile-Leu-Arg-Gly-Thr-Ser-Phe-Val-Tyr-Val) [Seq ID No. 3]; HBpol803–811 (Ser-Leu-Tyr-Ala-Asp-Ser-Pro-Ser-Val) [Seq ID No. 4]; or HBpol816–824 (Phe-Leu-Leu-Ser-Leu-Gly-Ile-His-Leu) [Seq ID No. 5], so long as the subject compounds are able to provide for cytotoxic T lymphocytic activity against at least one of the four major subtypes of HBV. Although different strains of HBV exist, they each share at least one common envelope determinant, which is designated "a". Each strain also has two other envelope determinants, one of which is either "d" or "y", and the second is either "w" or "r". Thus, there are four possible subtypes of the virus: adw, ayw, adr, and ayr. The cloning, sequencing and expression of HBV are described in GB 2034323, EP 13828, U.S. Pat. No. 4,935,235, and the complete sequence of the HBV envelope region is also described in Galibert et al., Nature 281:646 (1979), each of the foregoing being incorporated herein by reference. Amino acid sequences are described in the GenBank-72 database for 20 different HBV strains, including 7 of the adw subtype, 5 of the ayw subtype, 7 of the adr subtype, and 1 strain of the ayr subtype, the GenBank sequences also being incorporated herein by reference.

Therefore, the peptides may be subject to various changes, such as insertions, deletions, and substitutions, either conservative or non-conservative, where such changes provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV cytotoxic T lymphocyte stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. Where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequences identified by the present invention, including the representative peptides listed above, there are residues (or those which are substantially functionally equivalent) which allow the peptide to retain their biological activity, i.e., the ability to stimulate a class I-restricted cytotoxic T-lymphocytic response against HBV infected cells or cells which express HBV antigen. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid steric and charge interference which might disrupt binding.

Peptides which tolerate multiple substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the invention provides methods for identifying other epitopic regions associated with said peptide regions capable of inducing MHC-restricted cytotoxic T lymphocyte responses against HBV. The methods comprise obtaining peripheral blood lymphocytes (PBL) from infected or uninfected individuals and exposing (stimulating) the cells with synthetic peptide or polypeptide fragments derived from a peptide region of HBpol4–13 (Ser-Tyr-Gln-His-Phe-Arg-Lys-Leu-Leu-Leu) [Seq ID No. 12]; HBpol61–69 (Gly-Leu-Tyr-Ser-Ser-Thr-Val-Pro-Val) [Seq ID No. 1]; HBpol108–116 (Arg-Leu-Lys-Leu-Ile-Met-Pro-Ala-Arg) [Seq ID No. 13]; HBpol139–147 (Val-Val-Asn-His-Tyr-Phe-Gln-Thr-Arg) [Seq ID No. 14]; HBpol151–160 (His-Thr-Leu-Trp-Lys-Ala-Gly-Ile-Leu-Tyr) [Seq ID No. 15]; HBpol152–161 (Thr-Leu-Trp-Lys-Ala-Gly-Ile-Leu-Tyr-Lys) [Seq ID No. 16]; HBpol455–463 (Gly-Leu-Ser-Arg-Tyr-Val-Ala-Arg-Leu) [Seq ID No. 2]; HBpol505–514 (Leu-Tyr-Ser-His-Pro-Ile-Ile-Leu-Gly-Phe) [Seq ID No. 17); HBpol551–559 (Tyr-Met-Asp-Asp-Val-Val-Leu-Gly-Ala) [Seq ID No. 18]; HBpol575–583 (Phe-Leu-Leu-Ser-Leu-Gly-Ile-His-Leu) [Seq ID No. 19]; HBpol655–663 (Ala-Leu-Met-Pro-Leu-Tyr-Ala-Cys-Ile) [Seq ID No. 20]; HBpol748–757 (Gly-Thr-Asp-Asn-Ser-Val-Val-Leu-Ser-Arg) [Seq ID No. 21]; HBpol758–766 (Lys-Tyr-Thr-Ser-Phe-Pro-Trp-Leu-Leu) [Seq ID No. 22]; HBpol773–782 (Ile-Leu-Arg-Gly-Thr-Ser-Phe-Val-Tyr-Val) [Seq ID No. 3]; HBpol803–811 (Ser-Leu-Tyr-Ala-Asp-Ser-Pro-Ser-Val) [Seq ID No. 4]; or HBpol816–824 (Phe-Leu-Leu-Ser-Leu-Gly-Ile-His-Leu) [Seq ID No. 5]. Pools of overlapping synthetic peptides, each typically about 8 to 20 residues long, preferably 9–12 residues, can be used to stimulate the cells. Active peptides can be selected from pools which induce cytotoxic T lymphocyte activity. The ability of the peptides to induce specific cytotoxic activity is determined by incubating the stimulated PBL with autologous labeled (e.g., $^{51}$Cr) target cells (such as HLA matched macrophages, T cells, fibroblasts or B lymphoblastoid cells) infected or transfected with the HBV subgenomic fragments thereof, such that the targeted antigen is synthesized endogenously by the cell (or the cell is pulsed with the peptide of interest), and measuring specific release of label.

Once a peptide having an epitopic region which stimulates a cytotoxic T lymphocyte response is identified, the MHC restriction element of the response can be determined. This involves incubating the stimulated PBL or short term lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Carbone et al., *J. Exp. Med.* 167:1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HBV proteins would be undesirable in the development of HBV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HBV antigen, e.g., HBpol. Cells having activity are also stimulated with an appropriate T cell mitogen, e.g., phytohemagglutinin (PHA). The restimulated cells are provided with irradiated allogeneic PBLs as an antigen nonspecific source of T cell help, and HBV antigen. To selectively expand the population of cytotoxic T lymphocytes that recognize native HBV antigen and to establish long term lines, PBL from a patient are first stimulated with peptide and recombinant or native HBV antigen, followed by restimulation with HLA-matched B lymphoblastoid cells that stably express the corresponding HBV antigen polypeptide. The cell lines are re-confirmed for the ability to recognize endogenously synthesized antigen using autologous and allogeneic B-lymphoblastoid or other cells transfected or infected with appropriate antigen.

Having identified different peptides of the invention which contribute to inducing anti-HBV cytotoxic T lymphocyte responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g., the HBpol4–13 (Ser-Tyr-Gln-His-Phe-Arg-Lys-Leu-Leu-Leu) [Seq ID No. 12]; HBpol61–69 (Gly-Leu-Tyr-Ser-Ser-Thr-Val-Pro-Val) [Seq ID No. 1]; HBpol108–116 (Arg-Leu-Lys-Leu-Ile-Met-Pro-Ala-Arg) [Seq ID No. 13]; HBpol139–147 (Val-Val-Asn-His-Tyr-Phe-Gln-Thr-Arg) [Seq ID No. 14]; HBpol151–160 (His-Thr-Leu-Trp-Lys-Ala-Gly-Ile-Leu-Tyr) [Seq ID No. 15]; HBpol152–161 (Thr-Leu-Trp-Lys-Ala-Gly-Ile-Leu-Tyr-Lys) (Seq ID No. 16]; HBpol455–463 (Gly-Leu-Ser-Arg-Tyr-Val-Ala-Arg-Leu) [Seq ID No. 2]; HBpol505–514 (Leu-Tyr-Ser-His-Pro-Ile-Ile-Leu-Gly-Phe) [Seq ID No. 17]; HBpol551–559 (Tyr-Met-Asp-Asp-Val-Val-Leu-Gly-Ala) [Seq ID No. 18]; HBpol575–583 (Phe-Leu-Leu-Ser-Leu-Gly-Ile-His-Leu) [Seq ID No. 19]; HBpol655–663 (Ala-Leu-Met-Pro-Leu-Tyr-Ala-Cys-Ile) [Seq ID No. 20]; HBpol748–757 (Gly-Thr-Asp-Asn-Ser-Val-Val-Leu-Ser-Arg) [Seq ID No. 21]; HBpol758–766 (Lys-Tyr-Thr-Ser-Phe-Pro-Trp-Leu-Leu) [Seq ID No. 22]; HBpol773–782 (Ile-Leu-Arg-Gly-Thr-Ser-Phe-Val-Tyr-Val) [Seq ID No. 3]; HBpol803–811 (Ser-Leu-Tyr-Ala-Asp-Ser-Pro-Ser-Val) [Seq ID No. 4]; or HBpol816–824 (Phe-Leu-Leu-Ser-Leu-Gly-Ile-His-Leu) [Seq ID No. 5] peptides, which peptides can be combined in a "cocktail" to provide enhanced immunogenicity for cytotoxic T lymphocyte responses. Moreover, peptides of one region can be combined with peptides of other HBV regions, from the same or different HBV protein, particularly when a second or subsequent peptide has a MHC restriction element different from the first. Other CTL-inducing HBV peptides are described in co-pending application U.S. Ser. Nos. 07/935,898 and 08/024,120, which are incorporated herein by reference. This composition of peptides can be used to effectively broaden the immunological coverage provided by therapeutic, vaccine or diagnostic methods and compositions of the invention among a diverse population.

For example, the different frequencies of HLA alleles among prevalent ethnic groups (caucasian, asian and african blacks) are shown in Table I below. Therapeutic or vaccine compositions of the invention may be formulated to provide potential therapy or immunity to as high a percentage of a population as possible.

TABLE I

HLA ALLELE FREQUENCIES AMONG PREVALENT ETHNIC GROUPS

| HLA Allele | EUC | NAC | AFR | JPN |
|---|---|---|---|---|
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 7.7 | 9.9 | 16.6 | 1.1 |

Abbreviations: EUC, European Caucasian; NAC, North American Caucasian; AFR, African blacks, JPN, Japanese.
*A28 represents the two alleles Aw68 and Aw69

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, a peptide which contains T helper epitopes, heteropolymers with repeating units are provided. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). It will be understood that linkage should not substantially interfere with either of the linked groups to function as described, e.g., as an HBV cytotoxic T cell determinant, peptide analogs, or T helper determinant.

In another aspect the peptides of the invention can be combined or coupled with other peptides which present HBV T-helper cell epitopes, i.e., epitopes which stimulate T cells that cooperate in the induction of cytotoxic T cells to HBV. The T-helper cells can be either the T-helper 1 or T-helper 2 phenotype, for example. T-helper epitopes from HBV sequences have been identified at HBc1-20, having the sequence: Met-Asp-Ile-Asp-Pro-Tyr-Lys-Glu-Phe-Gly-Ala-Thr-Val-Glu-Leu-Leu-Ser-Phe-Leu-Pro [Seq ID No. 6]. Other T-helper epitopes are provided by peptides from the region HBc50–69, having the sequence Pro-His-His-Tyr-Ala-Leu-Arg-Gln-Ala-Ile-Leu-Cys-Trp-Gly-Glu-Leu-Met-Tyr-Leu-Ala [Seq ID No. 7], and from the region of HBc100–139, including HBc100–119 having the sequence Leu-Leu-Trp-Phe-His-Ile-Ser-Cys-Leu-Thr-Phe-Gly-Arg-Glu-Thr-Val-Ile-Glu-Tyr-Leu [Seq ID No. 8] (where $Ile_{116}$ is Leu in the HBV adw subtype), HBc117–131 having the sequence Glu-Tyr-Leu-Val-Ser-Phe-Gly-Val-Trp-Ile-Arg-Thr-Pro-Pro-Ala [Seq ID No. 9], and peptide HBc120-139 having the sequence Val-Ser-Phe-Gly-Val-Trp-Ile-Arg-Thr-Pro-Pro-Ala-Tyr-Arg-Pro-Pro-Asn-Ala-Pro-Ile [Seq ID No. 10]. See, Ferrari et al., *J. Clin. Invest.* 88:214–222 (1991), and U.S. Pat. No. 4,882,145, each incorporated herein by reference.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al., *Molecular Cloning. A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, whose disclosures are each incorporated herein by reference. Thus, fusion proteins which comprise one or more peptide sequences of the invention can be used to present the HBV cytotoxic T cell determinants. For example, a recombinant polymerase protein of the invention is prepared in which the HBpol amino acid sequence is altered so as to more effectively present epitopes of peptide regions described herein to stimulate a cytotoxic T lymphocyte response. By this means a polypeptide is used which incorporates several T cell epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range from about 1 µg to about 2,000 mg of peptide for a 70 kg patient, with dosages of from about 10 µg to about 100 mg of peptide being more commonly used, followed by booster dosages from about 1 µg to about 1 mg of peptide over weeks to months, depending on a patient's CTL response, as determined by measuring HBV-specific CTL activity in PBLs obtained from the patient. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals, about 90% of whom are capable of resolving the infection naturally. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3–6 months after infection. As individuals may develop chronic HBV infection because of an inadequate (or absent) cytotoxic T lymphocyte response during the acute phase of their infection, it is important to provide an amount of immunopotentiating peptide in a formulation and mode of administration sufficient to effectively stimulate a cytotoxic T cell response. Thus, for treatment of chronic hepatitis, a representative dose is in the range of about 1 µg to 1,000 mg, preferably about 5 µg to 100 mg for a 70 kg patient per dose. Administration should continue until at least clinical symptoms or laboratory indicators indicate that the HBV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the cytotoxic T-lymphocyte stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified which are capable of priming CTL in vivo against viral antigens, e.g., tripalmitoyl-S-glycerylcysteinly-seryl-serine ($P_3CSS$), which can effectively prime virus specific cytotoxic T lymphocytes when covalently attached to an appropriate peptide. See, Deres et al., Nature 342:561–564 (1989), incorporated herein by reference. Peptides of the invention can be coupled to $P_3CSS$, for example, and the lipopeptide administered to an individual to specifically prime a cytotoxic T lymphocyte response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection.

The concentration of cytotoxic T-lymphocyte stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Science*, 17th ed., Mack Publishing Company, Easton, Pa. (1985), which is incorporated herein by reference.

The peptides of the invention may also be administered via liposomes, which serve to target the peptides to a particular tissue, such as lymphoid tissue or HBV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, the mode of administration, the peptide being delivered, the stage of disease being treated, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the cytotoxic T-lymphocyte stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included as desired, e.g., lecithin for intranasal delivery.

In another aspect the present invention is directed to vaccines which contain as an active ingredient an immunogenically effective amount of a cytotoxic T-lymphocyte stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., keyhole limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HBV antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 μg to about 500 mg per 70 kilogram patient, more commonly from about 50 μg to about 200 mg per 70 kg of body weight. The peptides are administered to individuals of an appropriate HLA type, e.g., for vaccine compositions of peptides from the region of HBpol61–69 [Seq ID No. 1], Gly-Leu-Tyr-Ser-Ser-Thr-Val-Pro-Val; HBpol455–463 [Seq ID No. 2], Gly-Leu-Ser-Arg-Tyr-Val-Ala-Arg-Leu; HBpol551–559 and HBpol655–663; HBpol773–782 [Seq ID No. 3], Ile-Leu-Arg-Gly-Thr-Ser-Phe-Val-Tyr-Val; HBpol803–811 [Seq ID No. 4], Ser-Leu-Tyr-Ala-Asp-Ser-Pro-Ser-Val; or HBpol816–824 [Seq ID No. 5], Phe-Leu-Leu-Ser-Leu-Gly-Ile-His-Leu, these will be administered to at least HLA-A2 individuals. For peptides from HBpol151–160, these will be administered to at least HLA-A1 individuals. Vaccines comprising peptides from HBpol575–583 will be administered to at least HLA-A2.1 individuals. Vaccines comprising peptides from HBpol575–583 will be administered to at least HLA-A2.1 individuals. Vaccines comprising peptides from HBpol108–116, HBpol139–147, HBpol152–161, and HBpol748–757 will be administered to at least HLA-A3 individuals, and/or A24 individuals in the case of HBpol748–757. The peptides HBpol4–13, HBpol505–514, and HBpol758–766 will be administered to at least HLA-A24 individuals.

In some instances it may be desirable to combine the peptide vaccines of the invention with vaccines which induce neutralizing antibody responses to HBV, particularly to HBV envelope and/or core antigens, such as recombinant HBV env- and/or nucleocapside-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each being incorporated herein by reference. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HBV peptides of the invention. Upon introduction into an acutely or chronically HBV-infected host or into a non-infected host, the recombinant vaccinia virus expresses the HBV peptide and thereby elicits a host cytotoxic T lymphocyte response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy. By ex vivo therapy is meant that therapeutic or immunogenic manipulations are performed outside the body. For example, lymphocytes or other target cells may be removed from a patient and treated with high doses of the subject peptides, providing a stimulatory concentration of peptide in the cell medium far in excess of levels which could be accomplished or tolerated by the patient. Following treatment to stimulate the CTLs, the cells are returned to the host to treat the HBV infection. The host's cells may also be exposed to vectors which carry genes encoding the peptides, as described above. Once transfected with the vectors, the cells may be propagated in vitro or returned to the patient. The cells which are propagated in vitro may be returned to the patient after reaching a predetermined cell density.

In one method, ex vivo CTL responses to a HBV are induced by incubating in tissue culture a patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (an HBV infected cell). To optimize the in vitro conditions for the generation of specific cytotoxic T cells, the culture of stimulator cells is typically maintained in an appropriate serum-free medium. Peripheral blood lymphocytes are conveniently isolated following simple venipuncture or leukapheresis of normal donors or patients and used as the responder cell sources of CTLp. In one embodiment, the appropriate APC are incubated with about 10–100 µM of peptide in serum-free media for 4 hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of the HBV polymerase antigen from which the peptide sequence was derived. Specificity and MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides.

The induction of CTL in vitro requires the specific recognition of peptides that are bound to allele specific MHC class I molecules on APC. Peptide loading of empty major histocompatibility complex molecules on cells allows the induction of primary CTL responses. Since mutant cell lines do not exist for every human MHC allele, it may be advantageous to use a technique to remove endogenous MHC-associated peptides from the surface of APC, followed by loading the resulting empty MHC molecules with the immunogenic peptides of interest. The use of non-transformed, non-infected cells, and preferably, autologous cells of patients as APC is desirable for the design of CTL induction protocols directed towards development of ex vivo CTL therapies. Typically, prior to incubation of the APCs with the CTLp to be activated, an amount of antigenic peptide is added to the APC or stimulator cell culture, of sufficient quantity to become loaded onto the human Class I molecules to be expressed on the surface of the APCs. Resting or precursor CTLs are then incubated in culture with the appropriate APCs for a time period sufficient to activate the CTLs. Preferably, the CTLs are activated in an antigen-specific manner. The ratio of resting or precursor CTLs to APCs may vary from individual to individual and may further depend upon variables such as the amenability of an individual's lymphocytes to culturing conditions and the nature and severity of the disease condition or other condition for which the described treatment modality is used. Preferably, however, the CTL:APC ratio is in the range of about 30:1 to 300:1. The CTL/APC may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged molecules may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$–$5\times10^7$ cells used in mice.

Methods of reintroducing cellular components are known in the art and include procedures such as those exemplified in U.S. Pat. No. 4,844,893 to Honsik, et al. and U.S. Pat. No. 4,690,915 to Rosenberg, which are incorporated herein by reference. For example, administration of activated CTLs via intravenous infusion is typically appropriate.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE I

HLA-Restricted CTL Response to HBV Polymerase Epitopes

This Example describes the identification of an HLA-A2 restricted CTL response to two HBV polymerase peptides in a patient with acute viral hepatitis. The epitopes are present in amino acid sequences $HBpol_{61-69}$ [Seq ID No. 1] Gly-Leu-Tyr-Ser-Ser-Thr-Val-Pro-Val (GLYSSTVPV) (also designated peptide 927.32) and $HBpol_{803-811}$ [Seq ID No. 4] Ser-Leu-Tyr-Ala-Asp-Ser-Pro-Ser-Val (SLYADSPSV) (also designated peptide 927.27).

The CTL induced by the HBpol peptides were identified in PBMCs from a patient with acute hepatitis according to the procedure set forth in Example VI of pending application U.S. Ser. No. 07/935,898, except that the PMBCs were stimulated with individual peptides rather than peptide mixtures. The resulting CTL lines and/or clones were then tested for the ability to kill HLA-A2 matched target cells that were either pulsed with the peptide or that expressed the corresponding endogenous polymerase antigen (Vpol or EBO-pol). Construction of the vaccinia based Vpol and Epstein-Barr virus based EBO-pol constructs was as described in Example II of U.S. Ser. No. 07/935,898.

Figure 2:
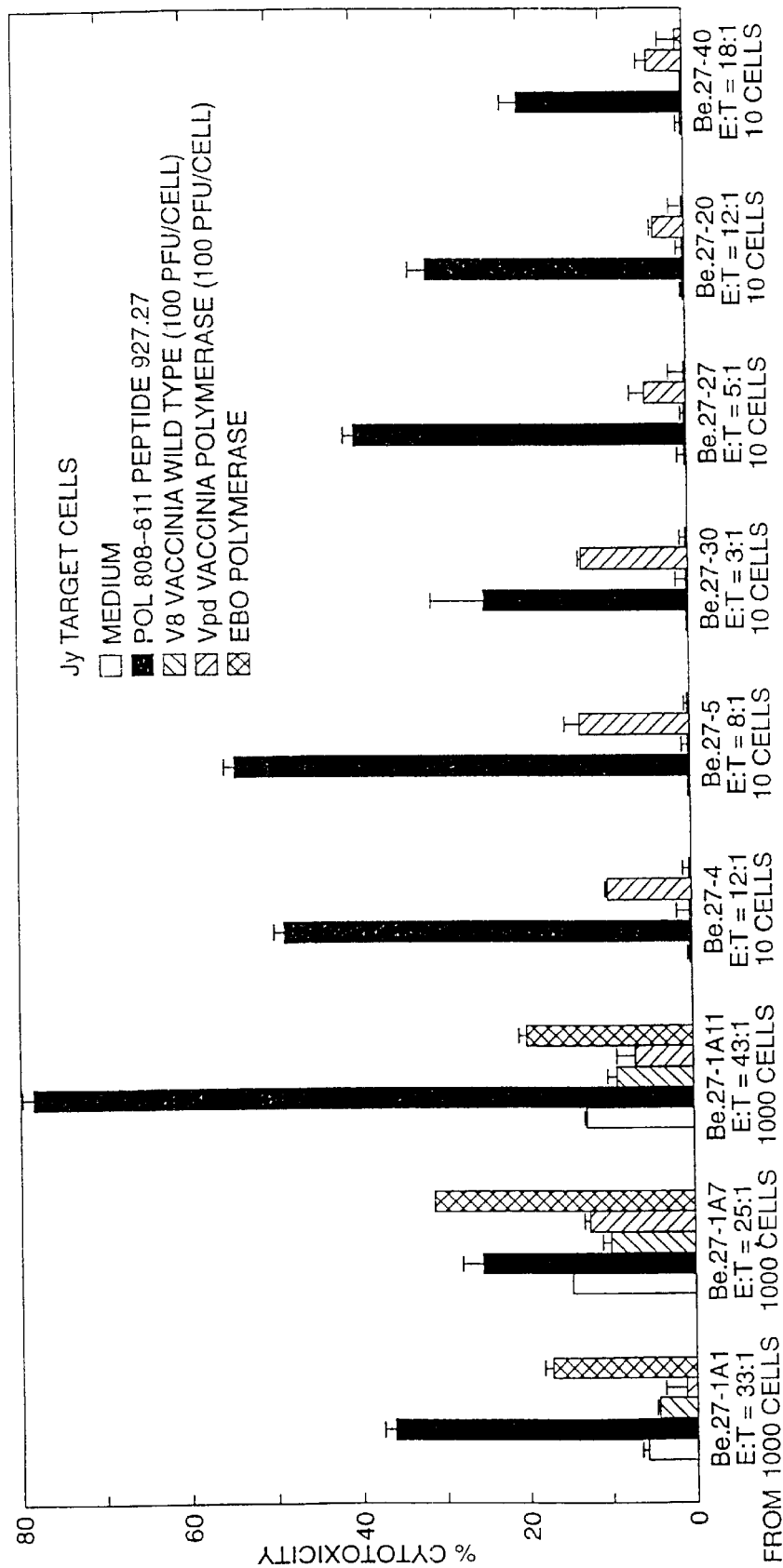
FIG. 2 shows the ability of several polymerase 803–811 peptide specific clones to recognize endogenously synthesized polymerase.

As shown in FIG. 1, both peptides $HBpol_{803-811}$ and $HBpol_{61-69}$ stimulated CTL responses in a patient (HLA-A2$^+$) using target cells pulsed with peptide, whereas other peptides 927.24 (WILRGTSFR) [Seq ID No. 23] and 927.30 (DLNLGNLNV) [Seq ID No. 24] and media controls did not stimulate the specific CTL response. The ability of the $HBpol_{803-811}$ specific clones to recognize endogenously synthesized polymerase antigen (Vpol and EBO-pol) is shown in FIG. 2. Two clones, designated Be.27-1A1 and Be.27-1A5, were identified that recognized the $HBpol_{803-811}$ peptide. As shown in FIG. 3, CTL responses to $HBpol_{61-69}$ and $HBpol_{803-811}$ were shown with target cells pulsed with homologous peptide, but only the $HBpol_{803-811}$ clone showed a response to endogenously synthesized Vpol antigen.

EXAMPLE II

This example demonstrates that acutely infected patients with clinically apparent viral hepatitis develop an HLA class I restricted CTL response to multiple epitopes in the conserved functional domains of the HBV polymerase protein, while persistently infected patients with chronic hepatitis and normal uninfected controls do not.

Nine HLA-A2 positive patients with acute hepatitis B, nine patients with chronic hepatitis B and ten healthy uninfected subjects were studied (Table II). The diagnosis of acute hepatitis B was based on clinical and biochemical evidence of acute liver injury according to standard diagnostic criteria, together with serological evidence of acute HBV infection, i.e., hepatitis B surface antigen (HBsAg, hepatitis B e antigen (HBeAg) and IgM anti-HBc antibody (IgM HBc-Ab), and the absence of serologic evidence of hepatitis delta or hepatitis C virus infection. Six of the nine patients recovered completely with normalization of serum transaminases and clearance of HBsAg and HBeAg within four months of initial diagnosis; the remaining three patients were lost to follow up. All patients with chronic hepatitis B were repeatedly serologic positive for HBsAg for more than six months and displayed mildly to moderately elevated serum ALT activity. Normal controls had no clinical history of HBV infection and were serologically negative for all HBV markers.

The amino acid sequence of HBV polymerase was screened for 9-mers and 10-mers containing the HLA-A2 allele specific binding motif. This search yielded 220 candidate peptides. Out of this group 44 peptides were selected based on conservation in at least 4 of the 7 HBV adw sequences in the GenBank Database. Lyophilized peptides were reconstituted at 20 mg/ml in DMSO and diluted to 1 mg/ml with RPMI 1640 medium.

TABLE II

Characteristics of Subjects Studied

| Subject | Sex | Diagnosis | HLA class I haplotype |
|---|---|---|---|
| A-1 | Male | Acute | A2, A24, B51, B53, Cw1 |
| A-2 | Male | Acute | A2, A63, B44, B54, Cw7 |
| A-3 | Male | Acute | A2, A24, B27, B71/72, Cw1, Cw4 |
| A-4 | Female | Acute | A2, A31, B51, B6, Cw3 |
| A-5 | Male | Acute | A2, A30, B44, B35, Cw4, Cw7 |
| A-6 | Female | Acute | A2, A69, B53, Cw4 |
| A-7 | Female | Acute | A2, A74, B62, B57, Cw3, Cw6 |
| A-8 | Male | Acute | A2, A68, B58, B27, Cw1, Cw6 |
| A-9 | Male | Acute | A2, A30, B35, Cw5 |
| CH-1 | Male | Chronic | A2, A23, B44 |
| CH-2 | Male | Chronic | A2, A1, B8, B44, Cw7, Cw4 |
| CH-3 | Male | Chronic | A2, A68, B59, B44, Cw5, Cw7 |
| CH-4 | Male | Chronic | A2, B7801, B13, Cw7 |
| CH-5 | Male | Chronic | A2, A30, B44, B13, Cw6 |
| CH-6 | Male | Chronic | A2, A34, B8, B27, Cw7 |
| CH-7 | Male | Chronic | A2, A33, B62, B67, Cw8 |
| CH-8 | Male | Chronic | A2, A69, B41, B52 |
| CH-9 | Male | Chronic | A2, A25, B18, Cw6 |
| N-1 | Female | Normal | A2, A32, B18, B60, Cw3, Cw7 |
| N-2 | Male | Normal | A2, B44, Cw7 |
| N-3 | Male | Normal | A2, A1, B8, B18, Cw7 |
| N-4 | Female | Normal | A2, B44, Cw63 |
| N-5 | Male | Normal | A2, A23, B5, B58, Cw2, Cw6 |
| N-6 | Male | Normal | A2, B35, B56, Cw1, Cw3 |
| N-7 | Male | Normal | A2, A11, B8, B62, Cw4, Cw7 |
| N-8 | Female | Normal | A2, A3, B7, B60, Cw3, Cw7 |
| N-9 | Male | Normal | A2, A11, B35, B44, Cw4 |
| N-10 | Male | Normal | A2, A3, B13, B35, Cw4 |

The binding affinity of the peptides to the class I molecule was determined by competitive binding assays using the radiolabeled peptide FLPSDYFPSV [Seq ID No. 25] representing HBc18–27. The peptide was iodinated to a specific activity of $5$–$10\times10^7$ cpm/mol by the chloramine T method of Buus et al., *Science* 235: 1353 (1987), incorporated herein by reference. Purified class I molecules (10 to 50 nM) were incubated at room temp. with various doses of the peptides, together with 5 to 10 nM of the labeled peptide and 1 μM human β2-microglobulin in PBS, pH 7.0, 0.05% NP-40, 1 mM PMSF, 1.3 mM 1,10-phenanthroline, 73 μM pepstatin A, 8 mM EDTA, and 200 μM TLCK. After 48 hrs., class I-peptide complexes were separated from free peptide by gel filtration on either a TSK2000 (7.8 mm×15 cm) column eluted with PBS pH 6.5, 0.5% NP-40, 0.1% NaN$_3$, or a Sephadex G-50 column (22 ml bed volume) eluted with the same buffer at pH 7.0. Class I-bound and free radioactivity was measured and the doses of peptides yielding 50% inhibition of the binding of the labeled peptide (IC50) were calculated. Before conducting inhibition assays, purified class I molecules were titered in the presence of a fixed amount of labeled peptide to determine the concentration necessary to bind 10 to 30% of the total radioactivity added. All subsequent inhibition assays were then performed using these class I concentrations. Each peptide was tested in two to four independent experiments.

Fifteen of the peptides displayed an HLA-A2.1 binding affinity ratio greater than 0.01 (Table III), a threshold below which most peptides are not immunogenic. In addition two peptides which contain HLA-A2 restricted CTL epitopes were included for comparison, HBc18–27 and HBs335–343.

peptide, rIL-2 and irradiated (3000 rad) autologous feeder cells and they were tested for cytotoxic activity on day 14. Selected cultures that displayed peptide specific cytolytic activity were separated into CD4+ and CD8+ populations by panning onto anti-CD4 coated flasks (Applied Immunosciences, Santa Clara, Calif.) and restimulated as described above.

CTL lines were established as described above and enriched in highly cytotoxic CD8+ CTLs by cloning at 10 and 3 cells per well in 96-well microwell plates in the presence of 0.5 μg/ml CD3-specific monoclonal antibody (Coulter Immunology, Hialeah, Fla.), rIL-2 (100 U/ml) and 10$^5$ irradiated (3000 rad) allogeneic PBMC. HBV specific clones were established by cloning at 1 and 0.3 cells per well in the same way. Growing cultures were tested for cytotoxic activity against peptide-primed target cells on day 17 and cytotoxic lines and clones were expanded in a 24-well plate and restimulated every 7 to 10 days as described above.

For the cytotoxicity assays, target cells consisted of either 1) allogeneic HLA-matched and mismatched B-LCL (Amer. Soc. Histocompat. Immunogenetics, Boston, Mass.), incubated overnight with synthetic peptides at 10 μg/ml; 2) stable B-LCL transfectants that express HBsAg or HBpolAg produced by transfection of the EBV-transformed B-LCL with a panel of EBV-based expression vectors that contain

TABLE III

Characteristics of Peptides Tested

| Peptide | Amino Acid Sequence | Seq ID No. | Frequency in HBV subtypes total (20) | adw (7) | ayw (5) | adr (7) | ayr (1) | Binding affinity | Acute HBV patients tested | Responders | % 51Cr Release Mean | Range |
|---|---|---|---|---|---|---|---|---|---|---|---|---|
| Pol527–53 | LLAQFTSAI | 26 | 19 | 6 | 5 | 7 | 1 | 9.6000 | 2 | 0 | | |
| *Pol575–583 | FLLSLGIHL | 19 | 19 | 6 | 5 | 7 | 1 | 0.5200 | 9 | 6 | 38 | 16–81 |
| *Pol816–824 | SLYADSPSV | 5 | 8 | 4 | 4 | 0 | 0 | 0.3500 | 9 | 3 | 30 | 25–32 |
| Pol502–510 | KLHLYSHPI | 27 | 19 | 6 | 5 | 7 | 1 | 0.2900 | 3 | 0 | | |
| *Pol655–665 | ALMPLYACI | 28 | 19 | 6 | 5 | 7 | 1 | 0.2000 | 5 | 2 | 19 | 17–21 |
| *Pol551–559 | YMDDVVLGA | 18 | 18 | 5 | 5 | 7 | 1 | 0.1600 | 7 | 2 | 21 | 17–25 |
| Pol504–512 | HLYSHPIIL | 29 | 16 | 4 | 4 | 7 | 1 | 0.1300 | 2 | 0 | | |
| *Pol455–463 | GLSRYVARL | 2 | 11 | 7 | 4 | 0 | 0 | 0.1200 | 9 | 6 | 57 | 20–95 |
| Pol526–535 | FLLAQFTSAI | 30 | 19 | 6 | 5 | 7 | 1 | 0.0710 | 2 | 0 | | |
| Pol149–158 | YLHTLWKAGI | 31 | 20 | 7 | 5 | 7 | 1 | 0.0560 | 3 | 0 | | |
| Pol772–780 | WILRGTSFV | 32 | 16 | 6 | 5 | 4 | 1 | 0.0180 | 4 | 0 | | |
| *Pol773–782 | ILRGTSFVYV | 3 | 16 | 6 | 5 | 4 | 1 | 0.0160 | 7 | 3 | 18 | 16–21 |
| Pol765–774 | LLGCAANWIL | 33 | 16 | 6 | 5 | 4 | 1 | 0.0140 | 2 | 0 | | |
| Pol424–432 | NLSWLSLDV | 34 | 18 | 5 | 5 | 7 | 1 | 0.0130 | 3 | 0 | | |
| *Core18–27 | FLPSDFPPSV | 35 | 9 | 5 | 4 | 0 | 0 | 1.5000 | 9 | 4 | 64 | 54–78 |
| *Env335–343 | WLSLLVPFV | 36 | 20 | 7 | 5 | 7 | | 0.7200 | 9 | 6 | 66 | 21–88 |

To stimulate PBMC with the selected synthetic peptides and rHBcAg, PBMC from patients and normal donors were separated on Ficoll-Histopaque density gradients, washed three times in Hanks Balanced Salt Solution (HBSS), resuspended in RPMI 1640 supplemented with L-glutamine (2 mM), gentamicin (10 μg/ml), and 10% heat-inactivated human AB serum and plated in a 24-well plate at 4×10$^6$ cells/well. rHBcAG (Biogen, Cambridge, Mass.) was added to the cell cultures at 1 μg/ml and the synthetic peptides at 10 μg/ml. In some of the studies with healthy uninfected blood donors rHBcAg was either omitted or replaced by 10 μg/ml tetanus toxoid (Connaught Laboratories, Swiftwater, Pa.) since these individuals had not been previously exposed to HBV and did not benefit from rHBcAg-induced T cell help. On days 3 and 10, 1 ml of RPMI with 10% human AB serum and rIL-2 at 10 U/ml final concentration was added to each well. On day 7, the cultures were restimulated with the corresponding coding regions of the ayw subtype (Guilhot et al., J. Virol. 66: 2670 (1992), incorporated herein by reference); or 3) B-LCL infected with recombinant vaccinia viruses (a recombinant vaccinia virus construct that encodes the HBV polymerase protein (Vpol) was produced by insertion of a 2766 fragment representing nucleotides 2290–1874 of the HBV genome (ayw subtype) into the SmaI site of the pSCII vector by standard techniques as described in Chakrabarti et al., Mol. Cell. Biol. 5: 3403 (1985), incorporated herein by reference. Vaccinia-infected targets were prepared by infection of 10$^6$ cells at 50 PFU/cell on a rocking plate at room temp. for 1 h followed by a single wash and overnight incubation at 37° C. Target cells were then labeled with 100 μCi of $^{51}$Cr (Amersham Corp., Arlington Heights, Ill.) for 1 h and washed four times with HBSS. Cytolytic activity was determined in a standard 4-h $^{51}$Cr release assay using U-bottomed 96-well plates containing 5,000 targets/well. Stimulated PBMC from patients and normal controls were performed in duplicate. Percent cytotoxicity was determined from the formula 100× ((experimental release−spontaneous release)/(maximum release−spontaneous release)). Maximum release was determined by lysis of targets by detergent (1% Triton X-100; Sigma Chemical Co., St. Louis, Mo.). Spontaneous release was <20% of maximal release in all assays. The assay was considered positive if the specific $^{51}$Cr release from target cells containing antigen was ≧15% higher than the nonspecific $^{51}$Cr release from antigen nonspecific $^{51}$Cr release from antigen negative target cells and the nonspecific lysis was less than 15% of maximum.

As shown in Table III, eight of the nine acutely infected patients responded to at least one of the polymerase peptides and, as can be seen from Table III, six of the peptides were recognized by at least one patient, suggesting that they represented HLA-A2 restricted epitopes. The HLA binding ratio of 5 of 6 of these peptides was greater than 0.1, supporting a direct relationship between binding affinity and immunogenicity even among this group of high affinity peptides.

The HLA-A2 binding affinity of a peptide did not appear to be the only requirement for immunogenicity since the peptide (LLAQFTSAI) [Seq ID No. 26] with the highest binding affinity (9.600) did not elicit an immune response while one with a 600-times lower affinity (0.016) did. To exclude the possibility that this extremely high affinity peptide may have triggered potentially responsive CTL precursors to undergo apoptosis, PBMC were also stimulated with lower concentrations of this peptide (0.3, 1, 3 and 10 μg/ml) without inducing a CTL response, suggesting that nonresponsiveness to this and other high affinity peptides is probably due to other mechanisms.

Figure 5:
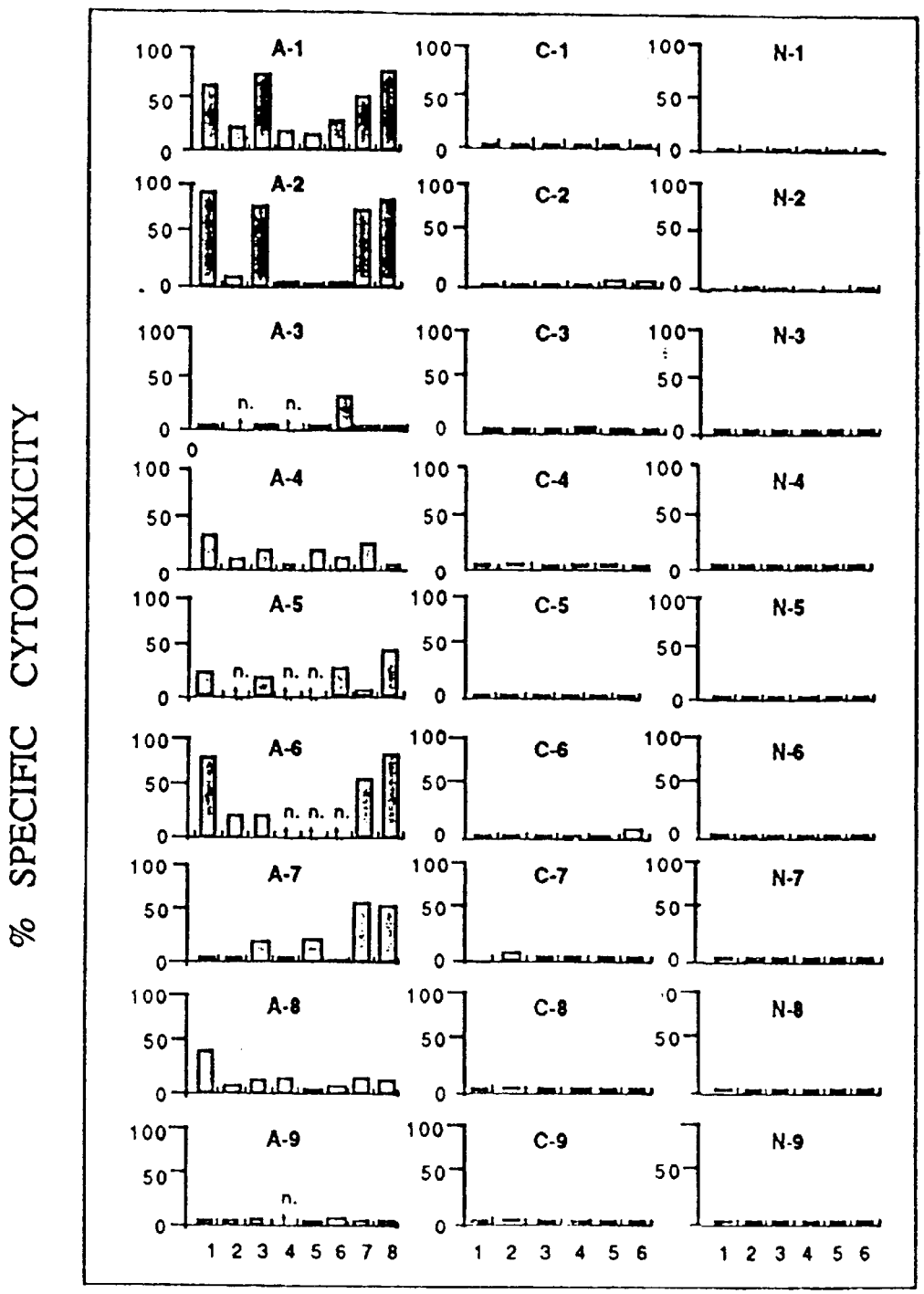
FIG. 5 shows HBV specific CTL response in patients with acute hepatitis (A-1–A-9), chronic hepatitis (C-1–C-9) and normal subjects (N-1–N-9). PBMC were stimulated with the peptides indicated for 2 weeks and tested in a 4-h $^{51}$Cr-release assay against JY target cells prepulsed overnight with the same peptide. Peptide-specific cytotoxicity was measured by subtracting the $^{51}$Cr-release by JY target cells not prepulsed with the peptide from the $^{51}$Cr-release by JY target cells prepulsed with the peptide. Results shown represent percent specific lysis in a 4 hr $^{51}$Cr-release assay at an E:T of 50:1.

The CTL responses of nine acutely infected patients who responded to one or more polymerase peptides are summarized in FIG. 5. Five of these patients also recognized the two control peptides, HBc18–27 and HBenv335–343, while one patient recognized only HBenv335–343, and one patient responded to neither. These results demonstrate the clonality and multispecificity of the CTL response against the polymerase protein during acute viral hepatitis. Importantly, nine of the 10 uninfected controls responded to any of the peptides used in this example (nine of these controls are shown in FIG. 5), suggesting that the CTL responses observed in the acutely infected patients represented in vitro secondary responses that were primed by exposure to infected cells in vivo. None of the nine patients with chronic hepatitis produced a response, suggesting that the vigor of the HBV specific CTL response has a role in determining which patients will clear the virus and which patients will not.

Figure 6:
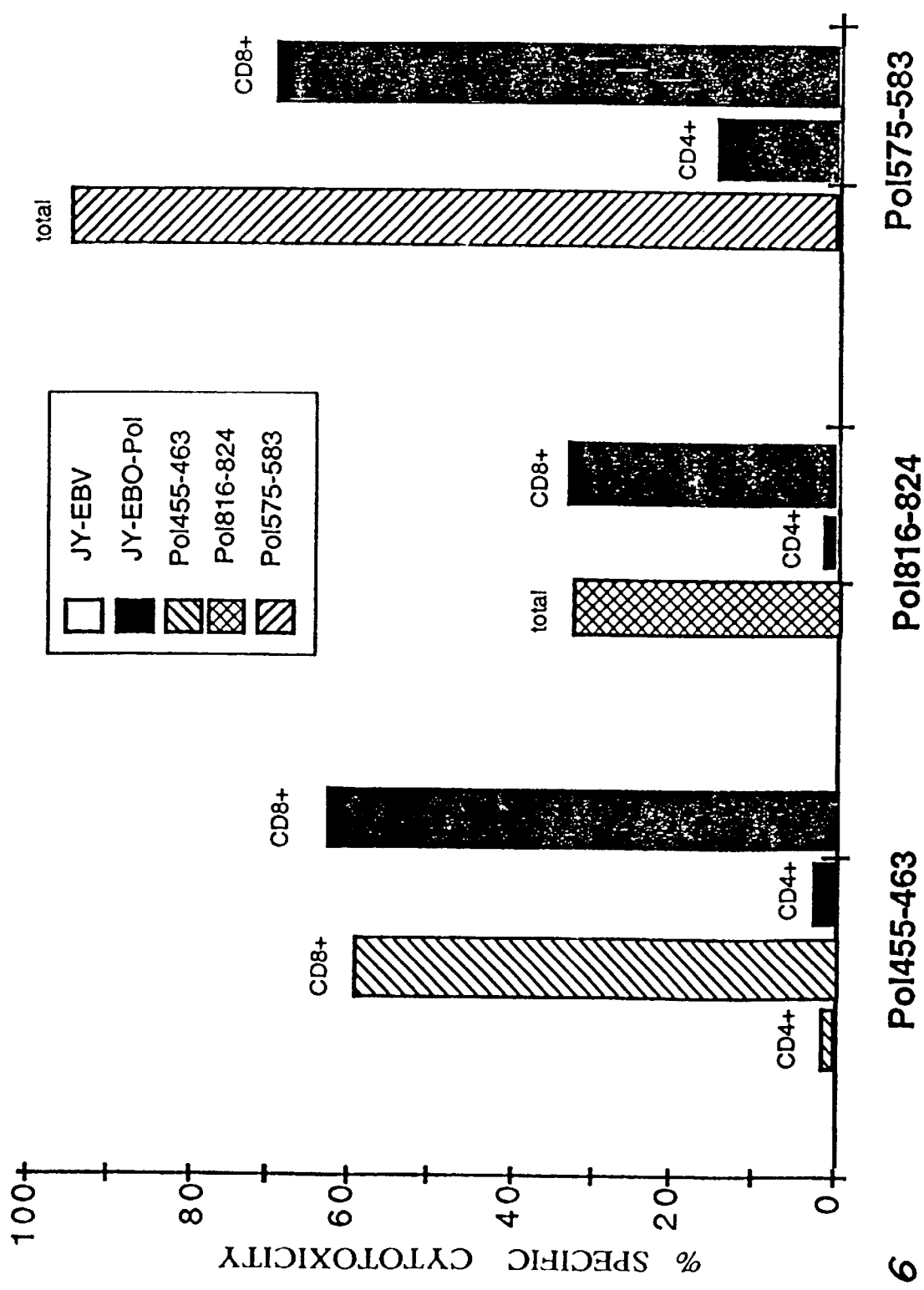
FIG. 6 shows CD8+ cells recognize endogenously synthesized antigen in target cells sharing the HLA-A2 allele (Patient A-1). Epitope-specific lines were generated by stimulating PBMC with the individual peptide for three weeks with weekly restimulation. On day 15 of CD4+ (positive selection) and CD8+ (negative selection) enriched lines were generated from the original bulk culture by panning. FACS-analysis showed an average enrichment by a factor of 3. Results shown represent percent specific lysis in a 4 hr $^{51}$Cr-release assay at an E:T of 30:1. Targets (JY-EBV) were either pulsed with the corresponding peptide overnight stably transfected with the polymerase expression vector.

Having identified two HLA-A2 patients (A-1 and A-2) with acute hepatitis who responded strongly to HBpol575–583 and HBpol455–463 and HBpol816–824 (Table III), these patients and peptides were chosen for further analysis. After two weeks of in vitro stimulation, selected cultures that displayed peptide specific CTL responses were enriched for CD4+ and CD8+ subsets by panning using positive and negative selection, respectively, and they were restimulated with peptide and tested for recognition of endogenously processed polymerase antigen after one additional week of culture. As shown in FIG. 6, the CTL response to these epitopes was mediated by CD8+ T cells since only the CD8+ fraction of each cell line recognized target cells that were either pulsed with the corresponding peptide or stably transfected with the polymerase expression vector. These results suggest that the peptides represent the native epitopes that are produced by the cellular processing of the polymerase protein, and that they are presented in the context of class I HLA molecules.

To obtain pure CD8+ cell lines and to characterize the T cell response at the clonal level, each of the three responding cell lines was cloned by limiting dilution in the presence of anti-CD3, irradiated allogeneic PBL and IL-2. All of the derivative cytotoxic lines were highly enriched in CD8+ cells as determined by FACS analysis (0.5–1.0×10$^6$ cells were washed once in PBS with 5% BSA and 0.02% sodium azide, the pelleted cells were then stained with a fluorescent probe conjugated anti-CD4 and anti-CD8 monoclonal antibody (Leu3a or Leu2a), and similarly labeled control antibody for 30 min. at 4° C., and after 3 washes in PBS with 5% BSA and 0.02% sodium azide, cells were analyzed with a FACScan flow cytometer). Furthermore, 5 of the 6 HBpol455–463 specific CTL clones derived in this manner also consisted of CD8+ cells.

Figure 7:
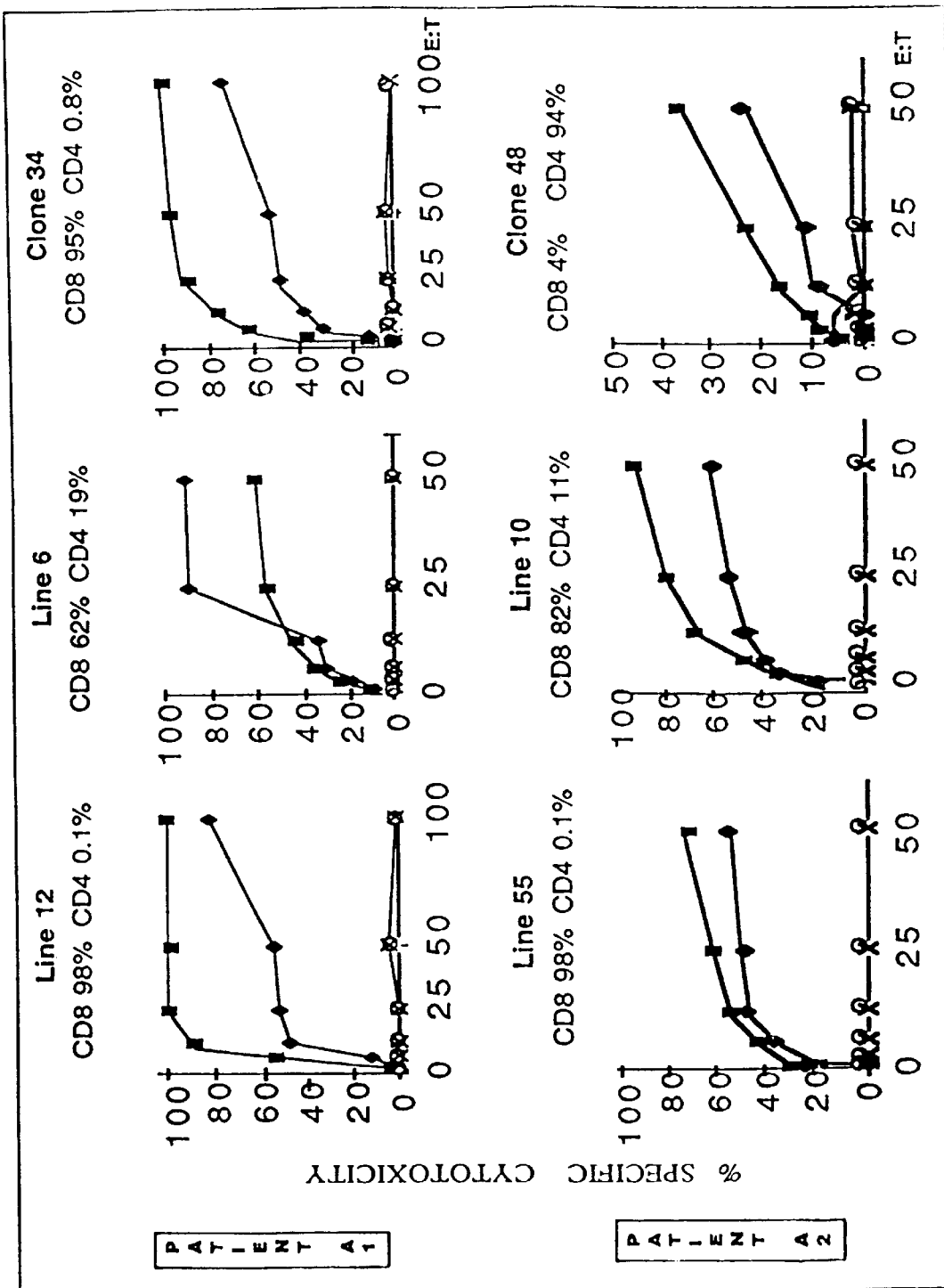
FIG. 7 shows CTL-response to Pol455–463 GLSRY-VARL [Seq ID No. 2]. Epitope-specific lines and clones, generated by stimulation with Pol455–463 peptide, were tested at varying E:T ratios against targets cells (JY-EBV), pulsed with the corresponding peptide (■) overnight or infected with recombinant vaccinia virus that express the HBV polymerase polypeptide (♦), in a standard 4 hr $^{51}$Cr-release assay. Wild-type vaccinia virus (Wt) (X) or JY-EBV peptides without peptide (○) were used as a control.

Four highly cytotoxic long term CTL lines and two clones specific for HBpol455–463 pulsed targets were chosen for further analysis (FIG. 7). The strength of the cytotoxic activity was assessed by varying the amount of the peptide used to pulse the target cells and by varying the effector to target ratios. The CTL displayed peptide dose dependent cytotoxic activity that recognized targets pulsed with peptide concentrations as low as 10 nM (Table IV), and they efficiently lysed both peptide pulsed and vaccinia-pol infected targets at E:T ratios as low as 1.6:1 (FIG. 7). Target cells pulsed with no peptide or with an irrelevant peptide (Table V), which is an HLA-A2 restricted epitope in HCV-infected patients, were not lysed, now were cells infected by the control recombinant vaccinia virus that expresses the HBV envelope protein, indicating the specificity of the CTL.

TABLE IV

Recognition GLSRYVARL-pulsed JY-EBV by CTL is peptide-dose dependent [Seq ID No. 2]

| | | JY-EBV pulsed with | | | | |
| --- | --- | --- | --- | --- | --- | --- |
| Patient | Line | 10 μM GLSRYVARL | 1 μM GLSRYVARL | 0.1 μM GLSRYVARL | 0.01 μM GLSRYVARL | no peptide |
| A-1 | 67–68 | 41% | 26% | 19% | 13% | 5% |
| A-2 | 10 | 75% | 56% | 52% | 25% | 12% |
| A-2 | 30 | 69% | 40% | 40% | 19% | 6% |

TABLE V

Induction of CTL with variant peptides to
GLSRYVARL [Seq ID No. 2] and an HCV epitope KLVALGINAV [Seq ID No. 37]

| | % Specific Cytotoxicity Against JY-EBV Preincubated with | | | | |
|---|---|---|---|---|---|
| Peptide During CTL-Induction | GLSRYVARL Seq ID 2 | GLPRYVARL Seq ID 38 | SGLSRYVARL Seq ID 39 | GLSRYVARLS Seq ID 40 | KLVALGINAV Seq ID 37 |
| GLSRYVARL | 54% | 18% | 40% | 41% | 2% |
| GLPRYVARL | 1% | 0% | 1% | 0% | |
| SGLSRYVARL | 0% | 0% | 0% | 0% | |
| GLSRYVARLS | 1% | 1% | 0% | 0% | |

To identify the restriction element used by the HBpol455–463 specific CTL, cytotoxic lines and clones from patients A-1 and A-2 were tested against allogeneic EBV-B cell lines sharing individual HLA class I alleles with the effector cells. As shown in FIG. 8, not only was HLA-A2 the sole class I allele shared by these two patients, but their CTL only lyse peptide pulsed target cells that share this allele. Thus, HBpol455–463 specific CTLs from both patients are HLA-A2 restricted.

Peptides containing carboxy- and amino-terminal truncations and elongations of the HBpol455–463 sequence were synthesized to determine the optimal length and the precise termini of the epitope. As shown in FIG. 9A, truncation of Gly455 or Leu463 greatly reduced the HLA binding affinity of the peptides and totally abrogated their recognition by CTL induced by the original peptide HBpol455–463. Elongation of this peptide by adding a single Ser residue normally present upstream of the amino terminus or downstream of the carboxy-terminus of HBpol455–463 did not diminish its recognition by CTL (FIG. 9A), and may have even increased recognition, despite the fact that the HLA-A2 binding affinity of the extended peptides was reduced 4–10 fold relative to the original peptide (FIG. 9A). The Ser-extended peptides did not induce CTL, as shown in Table V.

Direct sequencing of the PCR products amplified from the serum of 5 of the 9 patients with acute hepatitis B by nested PCR demonstrated that the deduced HBV amino acid sequence was identical to GLSRYVARL [Seq ID No. 2] in these patients. The sequence is present in 7/7 and 4/5 adw and ayw subtype sequences in GenBank. The amino acid sequence of the remaining ayw isolate in the database is GVSRYVARL [Seq ID No. 41], while the sequence of 6/7 adr and 1/1 ayr isolates is GLPRYVARL [Seq ID No. 42] and the sequence of the remaining adr isolate is GLPRYVVCL [Seq ID No. 43].

Peptides containing sequences of these different viral subtypes were tested for recognition by GLSRYVARL stimulated [Seq ID No. 2] PBMC to assess cross-reactivity of the CTL response. None of the variants was efficiently recognized by the CTL. GLSRYVVCL [Seq ID No. 44] was not recognized, even at very high peptide concentration, despite the fact that its HLA-A2.1 binding affinity was greater than the prototype peptide GLSRYVARL [Seq ID No. 2]. Thus, Ser457, Ala461 and Arg462 may represent T cell receptor contact sites (epitope residues) in this peptide. A substitution in Ser457 in GLPRYVARL [Seq ID No. 42] variant yielded more than a 10-fold reduction in its recognition by the CTL, while decreasing the HLA binding affinity 2-fold.

The GVSRYVARL [Seq ID No. 41] variant which contained the substitution at Leu456, a presumptive HLA contact site (agretope residue), was poorly recognized by the CTL, commensurate with the 9-fold reduction in its HLA-A2 binding affinity. However, the amino- and carboxy-terminally extended peptides described above were well recognized by the CTL despite the fact that they displayed comparably reduced HLA-A2 binding affinities (FIG. 9A). This suggests that Leu456 not only serves as an agretope residue, but may also influence the T cell receptor binding affinity of the peptide.

EXAMPLE X

Identification of CTL-Specific HBc Epitopes

Three patients (M. B., J. P. and J. V.) were studied during the acute phase of viral hepatitis type B. Diagnosis of acute hepatitis was based on the finding of elevated values of SGPT activity (at least 10 times the upper level of the normal; mean SGPT value peak being 2179 IU/L), associated with the detection of IgM anti-HBcAg antibodies in the serum. All patients recovered completely from the illness, with normalization of serum transaminase and clearance of HBsAg. They were antibody negative to δAg and to hepatitis C virus. Patient J. P. was A2, A3, B44, B35, Cw4, DR1, DR2, DRw8, and DQw1; V. J. was A2, A11, B44, B62, Cw5, DR4, DRw12; B. M. was A2, B38, B27, DR5, DRw52 and DQw3. Thus, all patients were HLA-A2 positive. Peripheral blood lymphocytes from these patients were analyzed for HBV specific CTL activity either immediately after isolation, after 1 or 2 weeks of stimulation with autologous stimulator cells transfected with HBV expression vectors as described below, or after stimulation with a panel of 4 pools of overlapping synthetic peptides which were 10 to 20 residues long, each comprising 5 to 6 peptides covering the entire HBV nucleocapsid (core and pre-core) region (ayw subtype). The peptides which comprised each pool (Mixes 1–4) are set out in Example XV.

Peptide-specific CTL were generated from the PBL of the three patients with acute hepatitis as follows. PBL were cultured at $4 \times 10^6$ cells per ml in RPMI 1640 containing 10% AB serum plus either 10 μg/ml of a peptide pool containing the $HBc_{11-27}$ peptide or the $HBc_{11-27}$ peptide and 1 μg/ml of recombinant (r)HBcAg (Biogen, Geneva, Switzerland), in a 24 well plate (Corning). After 4 days of culture, the cells were re-fed with RPMI 1640 containing 10% FCS and 20 U/ml rIL2 (Hoffman-LaRoche, Basel, Switzerland). In the case of patient V. J. the peptide-primed cells were restimulated after 1 week of culture with $HBc_{11-27}$ peptide and rHBcAg (1 mg/ml) in the presence of autologous irradiated (3500 RAD) PBL as antigen presenting cells. The peptide-primed cells from patient J. P. were restimulated on day 7 with 1 μg/ml of phytohemagglutinin (PHA) in the presence of allogeneic irradiated (7000 RAD) PBL. Cytotoxic activity was assessed after 7 days (patient M. B.) or 14 days (patients V. J. and J. P.) of culture.

Cytotoxic activity was assessed by incubating the stimulated PBL with autologous or allogeneic (HLA-matched or mismatched) $^{51}$Cr-labelled, peptide pulsed (20 μg/ml for 1 hr) BCL cells for 4 hr in round-bottomed 96-well plates at effector to target (E/T) ratios of 100 (M. B.) or 10 (V. J., J. P.). Parental BCL cells not pulsed with peptide served as negative controls. Per cent target cell lysis was calculated from the formula (E−M/T−M)×100, where E=experimental $^{51}$Cr release (cpm); M=$^{51}$Cr release in presence of culture medium (which ranged between 15–25% of total counts); and T=total $^{51}$Cr released by 10% Triton X.

HBV specific CTL activity was reproducibly observed only following stimulation with the panel of overlapping nucleocapsid peptides. Peptide specific CTL activity was consistently elicited only with one of the four peptide pools and recognition was limited to a single peptide within that pool, consisting of residues 11–27 of hepatitis B core antigen (HBcAg) of the sequence Ala-Thr-Val-Glu-Leu-Leu-Ser-Phe-Leu-Pro-Ser-Asp-Phe-Phe-Pro-Ser-Val, [[Seq. ID. No. 2]] (SEQ ID NO:73), which is conserved among the major subtypes of HBV. This is a dominant epitope in HLA-A2 positive patients with acute viral hepatitis.

Following one week of stimulation with a peptide mixture containing the HBc$_{11-27}$ determinant, lymphocytes from patient M. B. specifically lysed autologous and HLA-A2 matched B-lymphoblastoid cells (BCL) incubated with the peptide. A peptide-specific CTL line was also established from PBL derived from patient V. J. by stimulation with the HBc$_{11-27}$ peptide plus recombinant HBV-core antigen, as a source of antigen specific T cell help (Ferrari et al., *J. Immunol.* 145:3422 (1990) for expansion of the HBc$_{11-27}$ specific CTL, followed by restimulation by the same reagents. Similarly, an HBc$_{11-27}$ specific CTL line was established using PBL from patient J. P. by 1 week of peptide and HBcAg stimulation followed by restimulation with PHA and irradiated allogenic PBL as an antigen nonspecific source of T cell help. The procedures resulted in establishment of short term CTL lines that were able to lyse peptide-pulsed autologous and allogeneic HLA-A2 positive target cells, but not HLA-A2 mismatched targets, demonstrating that peptide recognition by the CTL was HLA-A2 restricted.

In separate experiments performed as generally described herein, peptides HBc$_{19-27}$ and HBc$_{18-27}$ were found to specifically stimulate CTL activity in a manner restricted by at least HLA-A2. In other experiments peptides HBc$_{28-47}$ and HBc$_{111-125}$ were shown to specifically stimulate CTL activity against HBV antigens, and peptide HBc$_{140-154}$ stimulated CTL activity in a manner that appeared to be restricted to at least HLA-A31.

EXAMPLE XI

CTLs Specific for HBc Peptides Recognize Recombinant HBV Core Antigen

The short term, peptide-specific CTL lines from the three patients of Example X were tested for the capacity to recognize endogenously synthesized HBV core antigen using autologous and allogenic BCL targets transfected or infected with the HBV core expression vectors.

Two different eukaryotic expression systems were used. Recombinant vaccinia viruses that express either the HBV core (Vcore) or precore (Vprecore) polypeptides (subtype ayw) were used as described in Schlicht and Schaller, *J. Virol.* 63:5399 (1989), incorporated herein by reference. Additionally, EBV-B cells were stably transfected with a panel of recombinant plasmids which express the HBV core (EBO-core) and envelope (EBO-env) polypeptide (subtype ayw) in an Epstein-Barr virus based vector (EBOpLPP) as described in Canfield et al., *Mol. Cell. Biol.* 10:1367 (1990), incorporated herein by reference.

Effector cells derived from patient M. B. and J. P. after 7 and 14 days of stimulation as described in Example X were incubated with target cells for 4 hours at E/T ratios of 100:1 and 10:1, respectively. Before $^{51}$Cr-labeling, BCL targets were either infected with recombinant vaccinia viruses at a multiplicity of infection of 20 for 14 hours, to allow the expression of HBV-encoded gene products or, for patient J. P., transfected with EBV-based episomal vectors previously shown to induce efficient expression of either envelope (EBO-env) or nucleocapsid antigen (EBO-core).

The CTL specifically lysed autologous BCL that transiently or stably expressed the HBV core polypeptide but not the HBV envelope antigens. By employing a panel of HLA-A2 matched and mismatched allogenic target cells, specific recognition of endogenously synthesized native (recombinant) core antigen was also to be HLA-A2 restricted.

EXAMPLE XII

Sequential Stimulation With Nucleocapsid Transfectants Produces Anti-HBV CTL of High Affinity Stimulation with peptide antigen can induce CTL with low affinity for the corresponding endogenous protein (Carbon. et al., *J. Exp. Med.* 167:1767 (1988)), such that repetitive peptide stimulation may yield CTL that recognize the synthetic peptide but not native antigen. In order to selectively expand the population of CTL that recognize native nucleocapsid antigen and to establish long term lines for further analysis, PBL from patient J. V. were stimulated for 1 week with peptide HBc$_{11-27}$ plus recombinant HBcAg, following which the activated PBL were restimulated with HLA-matched transfected BCL that stably expressed the HBV nucleocapsid polypeptide.

The details were as follows. After two weeks of stimulation with HBc$_{11-27}$ peptide and rHBcAg, the peptide-specific CTL line J. V. was further restimulated every seven days with irradiated (7000 RAD) HLA class I-matched EBO-core transfectants (1×10$^6$/ml) plus autologous irradiated (3000 RAD) PBL (5×10$^6$/ml) and rHBcAg (1 mg/ml in RPMI+ 10% FCS+20 U/ml of rIL2. [As shown in FIG. 4A, the] The cytolytic activity was tested against HLA-A2 matched BCL either prepulsed with HBc$_{11-27}$ peptide or cultured in medium alone and against EBO transfectants expressing endogenously synthesized nucleocapsid or envelope antigens. Experiments were performed before (2 weeks) and after (4 weeks) two rounds of stimulation with EBO-core transfectants (E/T ratio=20:1).

Prior to restimulation the CTL displayed a high level of cytotoxicity towards peptide pulsed targets with only minimal specific killing of target cells expressing endogenously synthesized antigen. Following restimulation with the nucleocapsid transfectant, T cells displayed increased killing of targets that express endogenously synthesized antigen concomitant with a decrease in killing of peptide pulsed target cells.

Recognition of endogenously synthesized antigen increased progressively with time following restimulation. Recognition of endogenously synthesized HBV nucleocapsid antigens by CTL line V. J. during weeks 3, 4 and 5 of culture after 1, 2 or 3 sequential rounds of stimulation with EBO-core transfectants (E/T=20:1). These results suggest that CTL with higher affinity for the endogenously produced antigen were being selected.

The cytolytic activity towards HLA-A2 matched and mismatched BCL targets infected with recombinant vaccinia viruses (as described in Example XI) after 5 weeks of culture (E/T=50:1) was also assessed.

These results suggest that naturally processed nucleocapsid antigen is similar, but not identical, to the synthetic $HBc_{11-27}$ peptide used to expand the CTL precursor population. The fact that this sequential stimulation worked so well, when many prior attempts to detect HBV specific CTL in freshly isolated PBL without prior stimulation failed, suggests that the HBV specific CTL precursors are present in the peripheral blood compartment at very low frequency. The failure to induce HBc specific CTL solely by in vitro stimulation with stably transfected autologous BCL, which served as excellent target cells, suggest that higher epitope densities are generally required for CTL induction compared with the density required for lysis.

The phenotype of the $HBc_{11-27}$ specific CTL was assessed by incubating HBV core transfectants and nucleocapsid specific CTL line from patient V. J. with antibodies specific for the differentiation markers CD4 and CD8. The V. J. CTL line was tested against A2-positive EBO-core and EBO-env targets in the presence of saturating concentrations (0.6 µg/ml) of $IgG_1$ monoclonal antibodies anti-Leu-3a (CD4) and anti-Leu-2a (CD8), obtained from Becton-Dickinson. Antibodies were added to the culture at the initiation of the chromium release assay. Antigen specific lysis was blocked by 80% with antibodies to CD8 whereas no inhibition was obtained with antibodies to CD4. These results demonstrate that the $HBc_{11-12}$, specific, HLA-A2 restricted CTL activity is mediated exclusively by CD8 positive cells.

EXAMPLE XIII $HBc_{11-27}$ Specific CTL Recognize an Epitope Shared by the HBV Core and Precore Region Encoded Polypeptides The $HBc_{11-27}$ epitope(s) are located within two independent nucleocapsid polypeptides (core and precore), one of which (precore) contains an amino terminal signal sequence that leads to its translocation into the endoplasmic reticulum and secretion as hepatitis Be antigen (HBeAg) (Uy et al., *Virology* 155:89 (1986); Roosinck et al., *Mol. Cell. Biol.* 6:1393 (1986); and Standring et al., *Proc. Natl. Acad. Sci. USA* 85:8405 (1988)). The core polypeptide is primarily a cytoplasmic and nuclear protein (HBcAg) and is not secreted (Roosinck and Siddiqui, *J. Virol.* 61:955 (1987), and McLachlan et al., *J. Virol.* 61:683 (1987)). To determine whether one or both polypeptides serve to generate the HLA-A2 restricted $HBc_{11-27}$ specific CTL epitope(s), HLA-A2 positive BCL target cells were infected with recombinant vaccinia viruses engineered to express the native core and precore polypeptides independently, as described in Example XI. CTL line J. V. was used as a source of effector cells in a 4 hr $^{51}Cr$ release assay E:T ratios of 20, 10, and 5.

The results showed that both target cell lines were killed to an equivalent degree by $HBc_{11-27}$ specific CTL line from patient V. J., demonstrating that HBcAg and HBeAg shared a common intracellular processing pathway and that they are cross-reactive at the HLA class I restricted CTL level.

EXAMPLE XIV

Immunodominance of the $HBc_{11-27}$ CTL Epitope in HLA-A2 Haplotype Individuals To assess the immunodominance in the HLA-A2 haplotype of the CTL epitope(s) contained in peptide $HBc_{11-27}$, eight additional subjects with self-limited acute hepatitis B infection, four patients with chronic active hepatitis B, and eight healthy subjects without evidence of previous exposure to HBV (all HLA-A2 positive) were repeatedly tested.

All of the acute patients serially studied (every 7–10 days) during the symptomatic and the recovery periods of the disease efficiently recognized autologous target cells pulsed with peptide $HBc_{11-27}$ as well as with MIX4. Restriction experiments performed with MIX4-stimulated PBMC from four of them confirmed that CTL recognition of peptide $HBc_{11-27}$ was HLA-A2 restricted. Patient to patient variations in the patten of response to the peptide were observed during the course of the illness. The cytolytic activity was generally detectable during the icteric phase when transaminase values were high; in some patients the response was long-lasting, being still detectable when GPT levels had already become normal, and in other subjects the lytic activity became undetectable 2 or 3 weeks after the transaminase peak when GPT levels were still slightly altered. The lack of a constant association between CTL activity and SGPT levels suggested the peripheral blood compartment only partially reflected immune events taking place in the liver at the site of antigen synthesis and cellular injury.

Three of the four chronic patients (each one tested two or three times, following the same experimental protocol used for the acute patients), did not show cytolytic activity against autologous macrophages pulsed with peptide $HBc_{11-27}$, while one patient displayed detectable, though very low levels of cytotoxicity against the relevant peptide sequence. The lytic activity against peptide $HBc_{11-27}$ was not detectable in normal HLA-A2 positive control subjects, demonstrating that this response was not due to in vitro priming and that peptide stimulation selectively expanded a specific T cell population pre-primed in vivo by HBV infection.

These results show a clear correlation between the CTL response to core peptide $HBc_{11-27}$ and acute HBV infection in patients who succeed in clearing the virus.

EXAMPLE XV

Identification of CTL Activity Restricted to HLA-A31 and Aw68

This Example describes the identification of a CTL response to an HBV nucleocapsid epitope that is restricted by two independent HLA class I molecules, HLA-A31 and HLA-Aw68.

Six patients, five male and one female, with acute hepatitis B, and nine normal blood donors were studied (Table VI). The diagnosis of acute hepatitis B was based on standard diagnostic criteria including clinical and biochemical evidence of severe liver cell injury with alanine aminotransferase (ALT) activity at least 20 fold higher than the upper limits of normal, together with serological evidence of acute HBV infection, including hepatitis surface antigen (HBsAg) and IgM anti HBc antibody (IgM HBc-Ab) and the absence of serological evidence of infection by the hepatitis delta or hepatitis C viruses (using commercially available reagents obtained from Abbott Laboratories, North Chicago, Ill.). All patients recovered completely from the illness, with normalization of serum transaminase and clearance of HBsAg within 4 months of initial diagnosis.

TABLE VI

HLA Class of the Patients Studied and of the
HLA-A31 and Aw68 Normal Donors Used to Produce Target Cells

HLA CLASS I

PATIENT

| | |
|---|---|
| E.W. | A31, Aw68, B35, Cw3, Cw4 |
| H.P. | A2, Aw68, B35, Bw62, Cw3, Cw4 |
| V.T. | A25, A31, B7, BI8 |
| H.F. | A31, Aw68, Bw61, Cw3 |
| Q.M. | Aw36, Aw68, B49, Bw62, Cw1 |
| V.P. | A24, Aw68, B35, Bw67 |
| C.N. | A24, Aw68, Bw60, Cw3 |

DONOR

| | |
|---|---|
| a | A1, A31, B17, Bw60 |
| b | A2, A31, B27, B44, Cw1 |
| c | A3, A31, B7, B27 |
| d | A34, A31, B14, B35, Cw4 |
| e | A3, A31, B7 |
| f | A31, Aw68, B35, Bw60 |
| g | A3, Aw68, B7, B44, Cw7 |
| h | A1, Aw68, B8, B38, Cw7 |
| i | A11, Aw68, B35, B44, Cw4 |

PBMC from patients and normal donors were separated on Ficoll-Hypaque density gradients, washed three times in Hanks balanced salt solution (HBSS), resuspended in RPMI 1640 medium supplemented with L-glutamine (2 mM), penicillin (50 U/ml), streptomycin (50 µg/ml), and HEPES (10 mM) containing 10% heat-inactivated human AB serum and plated in 24/well plate at $4 \times 10^6$ cells/well. The synthetic peptides each at 10 µg/ml were added to cell cultures as follows: Mixture 1, core residues 1–20, 20–34, 28–47, 50–69, 70–89, 61–80; Mixture 2, core residues 82–101, 100–119, 120–139, 140–155, 155–169, 169–183; Mixture 3, pre-core residue 20-core residue 2, core residues 50–59, 117–131, 131–145, 111–125; and Mixture 4, core residues 11–27, 91–110, 147–160, 162–176. rHBcAg (Biogen, Geneva, Switzerland) was added at 1 µg/ml to derive the benefit of a helper T cell response within the culture during the first week of stimulation. At day 3, 1 ml of RPMI with 10% human AB serum and rIL2 at 10 U/ml final concentration was added in each well. The cultured PBMC were tested for CTL activity on day 7, and short term CTL lines that displayed CTL activity specific for the peptide mixture used during the first week of stimulation were expanded by restimulation as described below.

HBV core-specific CTL line H1 was generated from patient H. P., initially cultured with peptide Mix 2 plus rHBcAg, by weekly restimulation with $5 \times 10^5$ autologous PBMC irradiated (3000 rads) in RPMI plus 10% human AB serum, rIL2 (20U/ml) and peptide Mix 2 (first restimulation) or with peptide 140–155 (10 µg/ml) for all subsequent stimulations. CTL line E4 (from patient E. W.) and the CTL lines from 4 additional patients (V. T., H. F., Q. M., C. N.) were established by stimulating PBMC with peptide 140–155 plus rHBcAg for the first week, with weekly restimulation thereafter with peptide 140–155 and rIL2. The PBMC of the normal uninfected controls were stimulated similarly except that in selected instances tetanus toxoid was substituted for rHBc during the first week of stimulation to provide an alternate source of T cell help, since these individuals had not been exposed to HBcAg.

HBV specific CTL clones were generated by limiting dilution at 1 cell/well in 96 well microtiter plates from an HBV specific CTL line E4 (patient E. W.). After depletion of CD4+ T cells from the CTL line by incubation with a CD4-specific monoclonal antibody (Becton Dickinson, Mountain View, Calif.) plus complement, the cells were plated in the presence of PHA at 1 µ/ml, CD3-specific monoclonal antibody at 0.5 µg/ml (Coulter Immunology, Hialeah, Fla.) rIL—2 (20U/ml) and irradiated (5000 rads) allogeneic PBMC $10^5$/well. HBV specific clones were restimulated in a 24 well plate with 105 irradiated (9000 rads) autologous transfectants expressing the HBV core region (described above), with $2 \times 10^6$ allogeneic irradiated (3000 rads) PBMC feeder cells per well, in RPMI 1640 medium containing 10% heat inactivated FCS and 1 L2 20 U/ml.

For target cell lines, autologous and allogeneic EBV—transformed B lymphoblastoid cell lines (LCL) were either purchased from The American Society for Histocompatibility and Immunogenetics (Boston, Mass.) or established from a pool of patients and normal donors as described above. The cells were maintained in RPMI with 10% (vol/vol) heat-inactivated FCS. Short term lines of autologous PBMC blasts were produced by stimulating peripheral blood PBMC with PHA at 1 µg/ml in RPMI with 10% FCS, 10 U/ml rIL2 for 7 days before use as target cells.

Cytotoxicity Assays were performed using target cells of either a) autologous PHA stimulated blasts or allogeneic HLA matched and mismatched B-LCL incubated overnight with synthetic peptides at 10 pg/ml; b) stable B-LCL transfectants described above; or c) B-LCL infected with recombinant vaccinia viruses. Vaccinia infected targets were prepared by infection of $1 \times 10^6$ cells at 50 plaque-forming U/cell on a rocking plate at room temperature for one hour followed by a single wash and overnight incubation at 37° C. Target cells were then labeled with 100 µCi of $^{51}$Cr for one hour and washed three times with HBSS. Cytolytic activity was determined in a standard 4 hour $^{51}$Cr-release assay using U—bottom 96 well plates containing 5000 targets per well. Stimulated PBMC were tested at E:T ratios between 70–100:1, whereas EBV core specific CTL lines were tested at E:T ratios between 4–50:1, and normal donors stimulated PBMC at E:T ratio of 60:1. All assays were performed in duplicate. Percent cytotoxicity was determined from the formula: 100×[(experimental release−spontaneous release)/(maximum release−spontaneous release)). Maximum release was determined by lysis of targets by detergent (1% Triton X-100, Sigma). Spontaneous release was less than 25% of maximal release in all assays.

PBMC from 2 patients (E. W. and H. P.) with acute HBV infection were stimulated for 7 days with the peptide mixtures described above and then tested for cytolytic activity against autologous $^{51}$Cr-labeled, PHA-activated blasts prepulsed with the same peptide mixture or with media. Responses were observed to mixture 2 in both patients. The remaining cells were restimulated for a second week with peptide mixture 2 and the antigenic specificity of the restimulated CTL line was established with autologous PHA activated blast targets prepulsed with the individual peptides contained within the mixture. By this approach, peptide HBcAg 140–155 was shown to be responsible for the CTL activity induced by Mix 2 for both patients. No cytotoxic activity was observed using unstimulated PBMC of patient E. W. as effectors against autologous B-LCL fed with peptide HBcAg 140–155, suggesting that specific CTL were present at low frequency in the peripheral blood during acute HBV infection. Patient H. P. also displayed a CTL response to Mix 4, ultimately shown to be specific for core residues 11–27 and to be restricted by HLA-A2. This demonstrated that multiple, independently restricted CTL responses to non-overlapping CTL epitopes present on the same viral protein were readily detectable during acute HBV infection.

HBcAg 140–155 specific CTL lines were generated by weekly stimulation of PBMC either with Mix 2 or with an active constituent peptide (core residues 140–155). Line E4 (patient E. W.) was started in the presence of rHBcAg and peptide HBcAg 140–155; line H1 (patient H. P.) was started in the presence of rHBc and Mix 2. After four weeks of restimulation, the HLA class I restriction of CTL line H1 was tested by using several allogeneic target cells that were partially matched with the effector cells at the HLA class I loci but were completely HLA class II mismatched. The results illustrate that the CTL activity was HLA-Aw68 restricted.

The HBcAg 140–155 specific CTL line E4 was cloned at 1 cell/well in the presence of anti-CD3, PHA and allogeneic PBL as feeder cells. After 2 to 3 weeks, 15% of the seeded wells showed proliferation, and the growing cell populations were tested for specific lysis of autologous B-LCL preincubated with HBcAg 140–155. Two clones (3D11, 2D7) that displayed highly efficient specific cytotoxic activity were selected for further analysis. The clones were tested against autologous and allogeneic target cells partially matched with the effectors at the level of HLA class I and class II alleles. The cytolytic activity of clone 3D11 was found to be HLA-A31 restricted and the cytolytic activity of clone 2D7, derived from the same patient, was HLA-Aw68 restricted. Both clones displayed the CD4–, CD8+ phenotype by flow cytometry.

These results were confirmed and extended by analysis of 4 additional HLA-A31 or Aw68 positive patients with acute HBV infection (H. F., V. T., Q. M., C. N.). In all these patients, HBcAg 140–155 specific CTL lines were generated as described for line E4 (Table VII). Using partially HLA matched allogeneic target cells, the CTL response was shown to be restricted by the HLA-A31 allele in patient VT.; it was clearly HLA-Aw68 restricted in patient Q. M. and most likely Aw68 restricted in patient C. N., whereas the response in patient H. F. was too weak to permit analysis.

TABLE VII

HBcAg140–155 Specific CTL Response of CTL Lines From HLA-A31 and Aw68 Patients With Acute HBV Infection

| Patient | HLA Match | TARGET HBcAg 140–155 (% Specific Lysis) | Media |
|---|---|---|---|
| V.T. | A31 | 75 | 34 |
| H.F. | ALL | 10 | 1 |
| Q.M. | Aw68 | 23 | 0 |
| C.N. | Aw68, A24 | 25 | 10 |

PBMC stimulated with HBcAg 140–155 plus rHBcAg (1 µg/ml).

The ability of HBcAg 140–155 specific CTL lines and clones to lyse target cells that express endogenously synthesized HBcAg was determined. Two polyclonal CTL lines (E4, and H1) and two clones derived from line E4 (3D11, and 2D7) were tested for by using autologous and allogeneic target cells that had been infected with recombinant vaccinia viruses or stably transfected with the EBV based expression vectors that direct the synthesis of the HBV core and precore proteins by the cell. Line H1 was tested against endogenously synthesized core protein induced by the recombinant vaccinia virus, and line E4 was tested against endogenously synthesized core and precore proteins induced by both expression vectors. Clones 3D11 and 2D7 were tested only against endogenously synthesized core and precore proteins induced by the recombinant vaccinia viruses. Significant levels of specific cytolytic activity were detected in all cases. Recognition of endogenously synthesized antigen by HBcAg 140–155 peptide specific lines and clones demonstrated that the CTL epitope represented by the core sequence 140–155 is generated by the intracellular processing of endogenously synthesized HBV core and precore proteins, and that these CTL are primed in vivo during HBV infection. The latter conclusion is confirmed by the inability to establish HBcAg 140–155 specific CTL lines from 6 HLA-A31 positive or from 4 HLA-Aw68 positive normal uninfected controls.

To determine the minimum, optimally recognized HLA A31 and Aw68 restricted epitope within HBcAg 140–155, carboxy- and amino-terminal truncations of HBcAg 140–155 were produced, as shown in Table VIII. Clone 3D11, which is HLA A31 restricted, and clone 2D7, which is HLA Aw68 restricted, were effector cells used to define the fine specificity of the CTL response. Autologous B-LCL were preincubated with the truncated peptides and used as targets with the two clones. The data indicate that sequence 141–151 is the minimal, optimally recognized epitope for both restriction elements. From Table VIII it appears that residue 151 (Arg) defines the carboxy-terminus of the epitope recognized by both CTL clones although residue 150, which is also an arginine, can also serve as the carboxy-terminal residue, but less efficiently, for both clones as long as residue 141 serves as amino-terminus. Although residue 141 (Ser) appears to be the optimal amino-terminal residue, the data indicate that residue 142 (Thr) can also serve as the amino-terminus of the epitope for both clones if Arg 151 is the carboxy-terminal residue. In contrast, only the HLA-Aw6B restricted clone (2D7) can utilize Thr 142 if the carboxy-terminus of the peptide is extended beyond residue 151.

TABLE VIII

FINE SPECIFICITY ANALYSIS OF CYTOTOXIC ACTIVITY OF CLONES 3D11 AND 2D7

| | | Clone 3D11 Restriction Element A31 Percent $^{51}$CR Release | Clone 2D7 Element Aw68 $^{51}$CR Release | SEQ ID NO: |
|---|---|---|---|---|
| 140–155 | LSTLPETTVVRRRGRS | 72 | 62 | 76 |
| 140–154 | LSTLPETTVVRRRGR | 63 | 60 | 71 |
| 140–153 | LSTLPETTVVRRRG | 75 | 66 | 77 |
| 140–152 | LSTLPETTVVRRR | 77 | 69 | 78 |
| 140–151 | LSTLPETTVVRR | 72 | 67 | 79 |
| 140–150 | LSTLPETTVVR | 0 | 6 | 80 |
| 141–155 | STLPETTVVRRRGRS | 81 | 66 | 81 |
| 141–154 | STLPETTVVRRRGR | 79 | 67 | 82 |
| 141–153 | STLPETTVVRRRG | 79 | 59 | 83 |
| 141–152 | STLPETTVVRRR | 68 | 68 | 84 |
| 141–151 | STLPETTVVRR | 69 | 66 | 85 |
| 141–150 | STLPETTVVR | 20 | 52 | 86 |
| 141–149 | STLPETTVV | 0 | 3 | 87 |
| 142–155 | TLPETTVVRRRGRS | 8 | 63 | 88 |
| 142–154 | TLPETTVVRRRGR | 18 | 54 | 89 |
| 142–153 | TLPETTVVRRRG | 8 | 56 | 90 |
| 142–152 | TLPETTVVRRR | 2 | 37 | 91 |
| 142–151 | TLPETTVVRR | 47 | 60 | 92 |
| 142–150 | TLPETTVVR | 0 | 0 | 93 |
| 143–155 | LPETTVVRRRGRS | 0 | 0 | 94 |
| 143–154 | LPETTVVRRRGR | 0 | 0 | 95 |
| 143–153 | LPETTVVRRRG | 0 | 0 | 96 |
| 143–152 | LPETTVVRRR | 0 | 2 | 97 |
| 143–151 | LPETTVVRR | 0 | 0 | 98 |

To more precisely define the boundaries of the epitope(s), a dose titration analysis was conducted in which the two CTL clones were incubated with allogeneic HLA-A31 and HLA-Aw68 positive target cells preincubated with peptides 140–151, 141–150, 141–151, 141–152, 142–151 at different molar concentrations ranging from $_{10-3}$ μM to 1μM. Residues 141–151 represent a minimal optimally recognized epitope recognized by both of the CTL clones. Amino-terminal elongation by one residue did not affect efficiency of target lysis by either clone, while the addition of one amino acid at the carboxy terminus reduced the CTL response ten-fold for both HLA A31 and Aw68 restricted clones, demonstrating that both HLA alleles bind and present the same peptide to their corresponding CTL.

EXAMPLE XVI

HLA-Restricted CTL Response To HBV Polymerase Epitopes

This Example describes the identification of an HLA-A2 restricted CTL response to two HBV polymerase peptides in a patient with acute viral hepatitis. The epitopes are present in amino acid sequences HBpol$_{61-69}$ [[Seq. ID No. 9]] (SEQ ID NO:1) Gly-Leu-Tyr-Ser-Ser-Thr-Val-Pro-Val (GLYSSTVPV) (also designated peptide 927.32 in the FIGS.) and HBpol$_{803-811}$ [[Seq. ID No. 10]] (SEQ ID NO:6) Ser-Leu-Tyr-Ala-Asp-Ser-Pro-Ser-Val (SLYADSPSV) (also designated peptide 927.27 in the FIGS.).

The CTL induced by the HBpol peptides were identified in PBMCs from a patient with acute hepatitis according to the procedure set forth in Example XV, except that the PMBCs were stimulated with individual peptides rather than peptide mixtures. The resulting CTL lines and/or clones were then tested for the ability to kill HLA-A2 matched target cells that were either pulsed with the peptide or that expressed the corresponding endogenous polymerase antigen (Vpol or EBO-pol). Construction of the vaccinia based Vpol and Epstein-Barr virus based EBO-pol constructs was as described in Example XI.

Both peptides HBpol$_{803-811}$ and HBpol$_{61-69}$ stimulated CTL responses in a patient [(HLA-A2*)] (HLA-A2$^+$) using target cells pulsed with peptide, whereas other peptides 927.24 (WILRGTSFR; SEQ ID NO:23) and 927.30 (DLNLGNLNV; SEQ ID NO:24) and media controls did not stimulate the specific CTL response. The ability of the HBpol$_{803-811}$ specific clones to recognize endogenously synthesized polymerase antigen (Vpol and EBO-pol) was shown. Two clones, designated Be.27-1A1 and Be.27-1A5, were identified that recognized the HBpol$_{803-811}$ peptide. CTL responses to HBpol$_{61-69}$ and HBpol$_{803-811}$ were shown with target cells pulsed with homologous peptide, but only the HBpol$_{803-811}$ clone showed a response to endogenously synthesized Vpol antigen.

EXAMPLE XVII

HLA-Restricted CTL Response to HBV X Protein

This Example describes the identification of an HLA-A2 restricted CTL response in a patient with acute viral hepatitis to a peptide sequence derived from the HBV X protein. The CTL epitope is present in a peptide of the amino acid sequence HBx$_{126-134}$ [[Seq. ID No. 9] Glu-Ile-Arg-Leu-Lys-Val-Phe-Val-Leu] (SEQ ID NO:73) Glu-Ile-Arg-Leu-Lys-Val-Phe-Val-Leu (EIRLKVFVL).

The CTL induced by the HBpol peptides were identified in PBMCs from a patient with acute hepatitis according to the procedure set forth in Example XV, except that the PMBCs were stimulated with individual peptides rather than peptide mixtures. The resulting CTL lines were then tested for the ability to kill HLA-A2 matched target cells that were pulsed with the peptide.

CTL were stimulated by HBx peptide 126–134 where the amino terminal residue had been substituted with an alanine residue (EIRLKVFVL→AIRLKVFVL, SEQ ID NO:99). CTL that recognized the analog peptide also recognized the peptide with the wild type sequence. On the other hand, the wild type peptide was not able to induce a specific CTL response detectable with cells pulsed with either peptide.

EXAMPLE XIX

HLA-Restricted CTL Response to HBenv348–357

This Example describes the identification of an HLA-A2 restricted CTL response in a patient with acute viral hepatitis to a peptide sequence derived from the HBV envelope protein. The CTL epitope is present in a peptide of the amino acid sequence HBenv$_{348-357}$ [[Seq. ID No. 10]] (SEQ ID NO:74) Gly-Leu-Ser-Pro-Thr-Val-Trp-Leu-Ser-Val (subtype ayw) (Ala is substituted for the C-terminal Val in subtype adw).

The CTL induced by the HBenv 348–357 peptide were identified in PBMCs from a patient with acute hepatitis according to the procedure set forth in Example XV, except that the PMBCs were stimulated with individual peptide rather than peptide mixtures. The resulting CTL line was then tested for the ability to kill HLA-A2 matched target cells that were pulsed with the peptide or that expressed endogenous envelope antigens of ayw or adw subtypes.

CTL stimulated by HBenv peptide 348–357 responded to target cells (at effector:target cell ratio of 3:1) pulsed with peptide (designated 884.01-ayw) and to endogenous envelope antigen of the ayw subtype, but did not recognize the adw subtype, presumably due to the difference in the carboxy-terminal amino acid residue (Ala substituted for Val).

The results described in the foregoing Examples illustrate that the CTL response to HBV in man appears to be quite polyvalent, presumably to afford efficient protection from this serious viral infection. Furthermore the data indicate that the peptide stimulation strategy employed herein is both efficient and effective for the identification and analysis of the polyvalent response, restricted as it is by the polymorphic HLA class I locus. As additional HLA allele specific binding motifs are identified, HBV-derived peptides containing these motifs can be used for in vitro stimulation of CTL precursors.

All publications, patents and patent applications mentioned in this specification are herein incorporated by reference into the specification to the same extent as if each individual publication, patent or patent application was specifically and individually indicated to be incorporated herein by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An HBV immunogenic peptide composition comprising an immunogenic peptide of 50 amino acids or less in length, wherein said peptide comprises at least one of the following: at least four contiguous amino acids of an amino acid sequence of $HBc_{19-27}$, or at least 10 contiguous amino acids of an amino acid sequence of $HBc_{140-154}$;

and further wherein the peptide, or a fragment thereof, binds to an appropriate HLA molecule to form a complex recognized by cytotoxic T cells which T cells recognize a native HBV core protein antigen.

2. The composition of claim 1, wherein the peptide comprises at least four contiguous amino acids of the amino acid sequence $HBc_{19-27}$.

3. The composition of claim 1, wherein the peptide comprises at least ten contiguous amino acids of the amino acid sequence $HBc_{140-154}$.

4. The composition of claim 1, wherein the peptide is 25 amino acids or less in length.

5. The composition of claim 1, wherein the peptide comprises $HBc_{19-27}$.

6. The composition of claim 1, wherein the peptide comprises $HBc_{18-27}$.

7. The composition of claim 1, wherein the peptide comprises $HBc_{11-27}$.

8. The composition of claim 1 wherein the peptide comprises $HBc_{140-154}$, $HBc_{140-153}$, $HBc_{140-152}$, $HBc_{140-151}$, $HBc_{141-151}$, $HBc_{141-155}$, $HBc_{141-154}$, $HBc_{141-153}$, $HBc_{141-152}$, $HBc_{141-150}$, $HBc_{142-155}$, $HBc_{142-154}$, $HBc_{142-153}$, $HBc_{142-152}$, or $HBc_{142-151}$.

9. The composition of claim 1, wherein the peptide comprises $HBc_{141-151}$.

10. The composition of claim 1, wherein the peptide is 8, 9, 10, or 11 amino acids in length, when the peptide comprises at least four contiguous amino acids of an amino acid sequence of $HBc_{19-27}$; or is 10 or 11 amino acids in length, when the peptide comprises at least ten contiguous amino acids of an amino acid sequence of $HBc_{140-154}$.

11. The composition of claim 10, wherein the peptide is $HBc_{18-27}$.

12. The composition of claim 10, wherein the peptide is $HBc_{19-27}$.

13. The composition of claim 10, wherein the peptide is $HBc_{141-151}$.

14. The composition of claim 1 comprising the peptide and a pharmaceutically acceptable carrier.

15. The composition according to claim 14, wherein the peptide is in a therapeutically effective human dose and the pharmaceutically acceptable carrier is in a human dose.

16. The composition of claim 14, wherein the pharmaceutically acceptable carrier comprises a liposome.

17. The composition of claim 14, wherein the composition comprises the peptide in the form of a recombinant nucleic acid molecule that encodes the peptide.

18. The composition of claim 17, wherein the composition comprises the peptide in a form of nucleic acids that encode the peptide and at least one additional peptide.

19. The composition of claim 1 comprising the peptide and a second immunogenic peptide.

20. The composition of claim 19, wherein the second immunogenic peptide elicits a T-helper cell-mediated immune response.

21. The composition of claim 19, wherein the second immunogenic peptide elicits a cytotoxic T lymphocyte response.

22. The composition of claim 19, wherein the immunogenic peptide and the second immunogenic peptide are conjugated to form a heteropolymer.

23. A method of stimulating a cytotoxic T cell response, said method comprising:
providing an HBV immunogenic peptide of 50 amino acids or less in length wherein said peptide comprises at least one of the following: at least four contiguous amino acids of an amino acid sequence of $HBc_{19-27}$, or at least 10 contiguous amino acids of an amino acid sequence of $HBc_{140-154}$;
complexing the peptide, or a fragment thereof, with an appropriate HLA molecule; and,
contacting an HLA-restricted CTL, which T cell recognizes a native HBV core protein antigen, with the complex of the provided peptide and the HLA molecule, whereby a CTL response is stimulated.

24. The method of claim 23, wherein the complexing step occurs in vitro.

25. The method of claim 23, wherein the complexing step occurs in vivo.

26. The method of claim 23, wherein the providing step comprises expressing a recombinant nucleic acid that encodes the peptide.

27. The method of claim 23, wherein the providing step provides the peptide and a second immunogenic peptide.

28. The method of claim 27, wherein the second immunogenic peptide elicits a T-helper cell-mediated immune response.

29. The method of claim 27, wherein the second immunogenic peptide elicits a cytotoxic T cell immune response.

30. An HBV immunogenic peptide composition comprising a peptide of 20 amino acids or less in length, wherein the peptide comprises at least seven contiguous amino acids of $HBc_{28-47}$;
and further, wherein the peptide, or a fragment thereof, binds to an appropriate HLA molecule to form a complex recognized by cytotoxic T cells which T cells recognize a native HBV core protein antigen.

31. The composition of claim 30, wherein the peptide comprises $HBc_{28-47}$.

32. The composition of claim 30 comprising the peptide and a pharmaceutically acceptable carrier.

33. The composition according to claim 32, wherein the peptide is in a therapeutically effective human dose and the pharmaceutically acceptable carrier is in a human dose.

34. The composition of claim 32, wherein the pharmaceutically acceptable carrier comprises a liposome.

35. The composition of claim 32, wherein the composition comprises the peptide in the form of a recombinant nucleic acid molecule that encodes the peptide.

36. The composition of claim 35, wherein the composition comprises the peptide in a form of nucleic acids that encode the peptide and at least one additional peptide.

37. The composition of claim 30 comprising the peptide and a second immunogenic peptide.

38. The composition of claim 37, wherein the second immunogenic peptide elicits a T-helper cell-mediated immune response.

39. The composition of claim 37, wherein the second immunogenic peptide elicits a cytotoxic T lymphocyte response.

40. The composition of claim 37, wherein the immunogenic peptide and the second immunogenic peptide are conjugated to form a heteropolymer.

41. A method of stimulating a cytotoxic T cell response, said method comprising:
providing an HBV immunogenic peptide of 20 amino acids or less in length, wherein the peptide comprises at least seven contiguous amino acids of $HBc_{28-47}$;
complexing the peptide, or a fragment thereof, with an appropriate HLA molecule; and,
contacting an HLA-restricted CTL, which T cell recognizes a native HBV core protein antigen, with the complex of the provided peptide and the HLA molecule, whereby a CTL response is stimulated.

42. The method of claim 41, wherein the complexing step occurs in vitro.

43. The method of claim 41, wherein the complexing step occurs in vivo.

44. The method of claim 41, wherein the providing step comprises expressing a recombinant nucleic acid that encodes the peptide.

45. The method of claim 41, wherein the providing step provides the peptide and a second immunogenic peptide.

46. The method of claim 45, wherein the second immunogenic peptide elicits a T-helper cell-mediated immune response.

47. The method of claim 45, wherein the second immunogenic peptide elicits a cytotoxic T cell immune response.

48. An HBV immunogenic peptide composition comprising a peptide of 17 amino acids or less in length, wherein the peptide comprises at least seven contiguous amino acids of $HBc_{111-125}$;
and further, wherein the peptide, or a fragment thereof, binds to an appropriate HLA molecule to form a complex recognized by cytotoxic T cells which T cells recognize a native HBV core protein antigen.

49. The composition of claim 48, wherein the peptide comprises $HBc_{111-125}$.

50. The composition of claim 48 comprising the peptide and a pharmaceutically acceptable carrier.

51. The composition according to claim 50, wherein the peptide is in a therapeutically effective human dose and the pharmaceutically acceptable carrier is in a human dose.

52. The composition of claim 50, wherein the pharmaceutically acceptable carrier comprises a liposome.

53. The composition of claim 52, wherein the composition comprises the peptide in the form of a recombinant nucleic acid molecule that encodes the peptide.

54. The composition of claim 53, wherein the composition comprises the peptide in a form of nucleic acids that encode the peptide and at least one additional peptide.

55. The composition of claim 48 comprising the peptide and a second immunogenic peptide.

56. The composition of claim 55, wherein the second immunogenic peptide elicits a T-helper cell-mediated immune response.

57. The composition of claim 55, wherein the second immunogenic peptide elicits a cytotoxic T lymphocyte response.

58. The composition of claim 55, wherein the immunogenic peptide and the second immunogenic peptide are conjugated to form a heteropolymer.

59. A method of stimulating a cytotoxic T cell response, said method comprising:

providing an immunogenic peptide of 17 amino acids or less in length, wherein the peptide comprises at least seven contiguous amino acids of $HBc_{111-125}$;

complexing the peptide, or a fragment thereof, with an appropriate HLA molecule; and, contacting an HLA-restricted CTL, which T cell recognizes a native HBV core protein antigen, with the complex of the provided peptide and the HLA molecule, whereby a CTL response is stimulated.

60. The method of claim 59, wherein the complexing step occurs in vitro.

61. The method of claim 59, wherein the complexing step occurs in vivo.

62. The method of claim 59, wherein the providing step comprises expressing a recombinant nucleic acid that encodes the peptide.

63. The method of claim 59, wherein the providing step provides the peptide and a second immunogenic peptide.

64. The method of claim 63, wherein the second immunogenic peptide elicits a T-helper cell-mediated immune response.

65. The method of claim 63, wherein the second immunogenic peptide elicits a cytotoxic T cell immune response.

* * * * *

UNITED STATES PATENT AND TRADEMARK OFFICE
CERTIFICATE OF CORRECTION

PATENT NO.    : 6,607,727 B1
DATED         : August 19, 2003
INVENTOR(S)   : Francis V. Chisari et al.

It is certified that error appears in the above-identified patent and that said Letters Patent is hereby corrected as shown below:

Column 6,
Line 64, "II ($HBc_{19-27}$) [[Seq ID No. 4]] (SEQ ID NO:68)" should read
-- II ($HBc_{19-27}$) (SEQ ID NO:68) --.

Column 7,
Line 7, "III ($HBc_{18-27}$) [[Seq. ID No. 5]] (SEQ ID NO:69)" should read
-- III ($HBc_{18-27}$) (SEQ ID NO:69) --.
Line 21, "IV ($HBc_{111-125}$) [[Seq. ID No. 6]] (SEQ ID NO:70)" should read
-- IV ($HBc_{111-125}$) (SEQ ID NO:70) --.
Line 37, "V ($HB_{c140-154}$) [[Seq. ID No. 7]] (SEQ ID NO:71)" should read
-- V ($HB_{c140-154}$) (SEQ ID NO:71) --.
Line 58, "VI ($HBc_{28-47}$) [[Seq. ID No. 8]] (SEQ ID NO:72)" should read
-- VI ($HBc_{28-47}$) (SEQ ID NO:72) --.

Column 8,
Lines 10-12, "VII ($HBpol_{61-69}$) [[Seq. ID No. 9]] (SEQ ID NO:1) [Gly-Len-Tyr-Ser-Ser-Thr-Val-Pro-Val] Gly-Leu-Tyr-Ser-Ser-Thr-Val-Pro-Val" should read
-- VII ($HBpol_{61-69}$) (SEQ ID NO:1) Gly-Leu-Tyr-Ser-Ser-Thr-Val-Pro-Val --.
Line 13, "VIII ($HBpol_{803-811}$) [[Seq ID No. 10]] (SEQ ID NO:4)" should read
-- VIII ($HBpol_{803-811}$) (SEQ ID NO:4) --.
Line 31, "IX (HBx126-134) [[Seq. ID No. ]] (SEQ ID NO:73)" should read
-- IX (HBx126-134) (SEQ ID NO:73) --.
Lines 40-41, " X ($HBenv_{348-357}$) [[Seq. ID No. ]] (SEQ ID NO:74) Gly-Leu-Ser-Pro-Thr-Val-Trp-Len-Ser-Val" should read
-- X ($HBenv_{348-357}$) (SEQ ID NO:74) Gly-Leu-Ser-Pro-Thr-Val-Trp-Leu-Ser-Val --.

Column 30,
Line 24, "EXAMPLE X" should read -- EXAMPLE III --.
Line 49, "Example XV" should read -- Example VIII --.

Column 31,
Lines 19-20, "[[Seq. ID. No. 2]] (SEQ ID NO:73)" should read -- (SEQ ID NO:73) --.
Line 52, "EXAMPLE XI" should read -- EXAMPLE IV --.
Line 57, "Example X" should read -- Example III --.

Column 32,
Line 6, "Example X" should read -- Example III --.
Line 23, "EXAMPLE XII" should read -- EXAMPLE V --.

UNITED STATES PATENT AND TRADEMARK OFFICE
CERTIFICATE OF CORRECTION

PATENT NO. : 6,607,727 B1
DATED : August 19, 2003
INVENTOR(S) : Francis V. Chisari et al.

It is certified that error appears in the above-identified patent and that said Letters Patent is hereby corrected as shown below:

Column 33,
Line 6, "Example XI" should read -- Example IV --.
Line 35, "EXAMPLE XIII" should read -- EXAMPLE VI --.
Line 55, "Example XI" should read -- Example IV --.
Line 62, "EXAMPLE XIV" should read -- EXAMPLE VII --.

Column 34,
Line 43, "EXAMPLE XV" should read -- EXAMPLE VIII --.

Column 39,
Line 13, "EXAMPLE XVI" should read -- EXAMPLE IX --.

Column 39,
Lines 20-21, "$HBpol_{61-69}$ [[Seq. ID No. 9]] (SEQ ID NO:1)" should read -- $HBpol_{61-69}$ (SEQ ID NO:1) --.
Line 23, "$HBpol_{803-811}$ [[Seq. ID No. 10]] (SEQ ID NO:6)" should read -- $HBpol_{803-811}$ (SEQ ID NO:6) --.
Line 28, "Example XV" should read -- Example VIII --.
Line 36, "Example XI" should read -- Example IV --.
Line 52, "EXAMPLE XVII" should read -- EXAMPLE X --.
Lines 60-61, "$HBx_{126-134}$ [[Seq. ID No. 9] Glu-Ile-Arg-Leu-Lys-Val-Phe-Val-Leu] (SEQ ID NO:73)" should read -- $HBx_{126-134}$ (SEQ ID NO:73) --.
Line 65, "Example XV" should read -- Example VIII --.

Column 40,
Line 12, "EXAMPLE XIX" should read -- EXAMPLE XI --.
Lines 21-22, "$HBenv_{348-357}$ [[Seq. ID No. 10]] (SEQ ID NO:74)" should read -- $HBenv_{348-357}$ (SEQ ID NO:74) --.
Line 28, "Example XV" should read -- Example VIII --.

UNITED STATES PATENT AND TRADEMARK OFFICE
CERTIFICATE OF CORRECTION

PATENT NO. : 6,607,727 B1
DATED : August 19, 2003
INVENTOR(S) : Francis V. Chisari et al.

It is certified that error appears in the above-identified patent and that said Letters Patent is hereby corrected as shown below:

Column 164,
Line 65, "of claim 52" should read -- of claim 50 --.

Signed and Sealed this

Twenty-sixth Day of July, 2005

JON W. DUDAS
*Director of the United States Patent and Trademark Office*

SEQUENCE LISTING (1) GENERAL INFORMATION:

(iii) NUMBER OF SEQUENCES: 99

(2) INFORMATION FOR SEQ ID NO: 1:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Gly Leu Tyr Ser Ser Thr Val Pro Val
1               5

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Gly Leu Ser Arg Tyr Val Ala Arg Leu
1               5

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Ile Leu Arg Gly Thr Ser Phe Val Tyr Val
1               5                   10

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Ser Leu Tyr Ala Asp Ser Pro Ser Val
1               5

(2) INFORMATION FOR SEQ ID NO: 5:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Phe Leu Leu Ser Leu Gly Ile His Leu
1               5

(2) INFORMATION FOR SEQ ID NO: 6:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Met Asp Ile Asp Pro Tyr Lys Glu Phe Gly Ala Thr Val Glu Leu Leu
1               5                   10                  15

Ser Phe Leu Pro
            20

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Pro His His Tyr Ala Leu Arg Gln Ala Ile Leu Cys Trp Gly Glu Leu
1               5                   10                  15

Met Tyr Leu Ala
            20

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Leu Leu Trp Phe His Ile Ser Cys Leu Thr Phe Gly Arg Glu Thr Val
1               5                   10                  15

Ile Glu Tyr Leu
            20

(2) INFORMATION FOR SEQ ID NO: 9:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Glu Tyr Leu Val Ser Phe Gly Val Trp Ile Arg Thr Pro Pro Ala (2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

```
Val Ser Phe Gly Val Trp Ile Arg Thr Pro Pro Ala Tyr Arg Pro Pro
 1               5                  10                  15

Asn Ala Pro Ile
            20
```

(2) INFORMATION FOR SEQ ID NO: 11:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Modified-site
        (B) LOCATION: 1..845
        (D) OTHER INFORMATION: /product= "OTHER"
            /note= "Xaa = any amino acid
            (<50% consensus)"

(xi) SEQUENCE DESCRIPTION: SEQ ID NO: 11:

```
Met Pro Leu Ser Tyr Gln His Phe Arg Lys Leu Leu Leu Leu Asp Asp
 1               5                  10                  15

Gly Thr Glu Ala Gly Pro Leu Glu Glu Glu Leu Pro Arg Leu Ala Asp
                20                  25                  30

Glu Gly Leu Asn Arg Arg Val Ala Glu Asp Leu Asn Leu Gly Asn Leu
                35                  40                  45

Asn Val Ser Ile Pro Trp Thr His Lys Val Gly Asn Phe Thr Gly Leu
 50                  55                  60

Tyr Ser Ser Thr Val Pro Val Phe Asn Pro Glu Trp Gln Thr Pro Ser
 65                  70                  75                  80

Phe Pro Xaa Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Asn Xaa Thr Lys Tyr Leu Pro Leu Asp
                115                 120                 125

Lys Gly Ile Lys Pro Tyr Tyr Pro Glu His Xaa Val Asn His Tyr Phe
130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Phe Gln Thr Ser Thr
                180                 185                 190

Arg His Gly Asp Glu Ser Phe Cys Ser Gln Ser Ser Gly Ile Leu Ser
                195                 200                 205
```

-continued

```
Arg Ser Pro Val Gly Pro Cys Xaa Arg Ser Gln Leu Xaa Gln Ser Arg
    210                 215                 220
Leu Gly Leu Gln Pro Gln Gln Gly Xaa Leu Ala Arg Arg Gln Gln Gly
225                 230                 235                 240
Arg Ser Gly Ser Ile Arg Ala Arg Val His Pro Thr Thr Arg Arg Xaa
                245                 250                 255
Phe Gly Val Glu Pro Ser Gly Ser His Ile Asp Asn Xaa Ala Ser
                260                 265                 270
Ser Ser Ser Cys Leu His Gln Ser Ala Val Arg Lys Ala Ala Tyr
    275                 280                 285
Ser His Leu Ser Thr Ser Lys Arg Gln Ser Ser Gly His Ala Val
    290                 295                 300
Glu Leu His Asn Xaa Pro Pro Asn Ser Ala Arg Ser Gln Ser Glu Gly
305                 310                 315                 320
Pro Val Phe Ser Cys Trp Trp Leu Gln Phe Arg Asn Ser Lys Pro Cys
                325                 330                 335
Ser Asp Tyr Cys Leu Xaa His Ile Val Asn Leu Leu Glu Asp Trp Gly
                340                 345                 350
Pro Cys Thr Glu His Gly Glu His Xaa Ile Arg Ile Pro Arg Thr Pro
            355                 360                 365
Ala Arg Val Thr Gly Gly Val Phe Leu Val Asp Lys Asn Pro His Asn
370                 375                 380
Thr Thr Glu Ser Arg Leu Val Val Asp Phe Ser Gln Phe Ser Arg Gly
385                 390                 395                 400
Xaa Thr Arg Val Ser Trp Pro Lys Phe Ala Val Pro Asn Leu Gln Ser
                405                 410                 415
Leu Thr Asn Leu Leu Ser Ser Asn Leu Ser Trp Leu Ser Leu Asp Val
                420                 425                 430
Ser Ala Ala Phe Tyr His Ile Pro Leu His Pro Ala Ala Met Pro His
        435                 440                 445
Leu Leu Val Gly Ser Ser Gly Leu Ser Arg Tyr Val Ala Arg Leu Ser
    450                 455                 460
Ser Asn Ser Arg Ile Ile Asn Xaa Gln His Gly Thr Met Gln Asn Leu
465                 470                 475                 480
His Asp Ser Cys Ser Arg Asn Leu Tyr Val Ser Leu Leu Leu Leu Tyr
                485                 490                 495
Lys Thr Phe Gly Arg Lys Leu His Leu Tyr Ser His Pro Ile Ile Leu
                500                 505                 510
Gly Phe Arg Lys Ile Pro Met Gly Val Gly Leu Ser Pro Phe Leu Leu
            515                 520                 525
Ala Gln Phe Thr Ser Ala Ile Cys Ser Val Val Arg Arg Ala Phe Pro
530                 535                 540
His Cys Leu Ala Phe Ser Tyr Met Asp Asp Val Val Leu Gly Ala Lys
545                 550                 555                 560
Ser Val Gln His Leu Glu Ser Leu Phe Thr Ala Val Thr Asn Phe Leu
                565                 570                 575
Leu Ser Leu Gly Ile His Leu Asn Pro Asn Lys Thr Lys Arg Trp Gly
            580                 585                 590
Tyr Ser Leu Asn Phe Met Gly Tyr Val Ile Gly Ser Trp Gly Thr Leu
    595                 600                 605
Pro Gln Glu His Ile Val Gln Lys Ile Lys Gln Cys Phe Arg Lys Leu
610                 615                 620
```

```
Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ser Lys Gln Ala Phe Thr Phe Ser
                660                 665                 670

Pro Thr Tyr Lys Ala Phe Leu Cys Lys Gln Tyr Leu Asn Leu Tyr Pro
                675                 680                 685

Val Ala Arg Gln Arg Pro Gly Leu Cys Gln Val Phe Ala Asp Ala Thr
690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
                740                 745                 750

Val Val Leu Ser Arg Lys Tyr Thr Ser Phe Pro Trp Leu Leu Gly Cys
                755                 760                 765

Ala Ala Asn Trp Ile Leu Arg Gly Thr Ser Phe Val Tyr Val Pro Ser
770                 775                 780

Ala Leu Asn Pro Ala Asp Asp Pro Ser Arg Gly Arg Leu Gly Leu Tyr
785                 790                 795                 800

Arg Pro Leu Leu Arg Leu Pro Phe Arg Pro Thr Thr Gly Arg Thr Ser
                805                 810                 815

Leu Tyr Ala Val Ser Pro Ser Val Pro Ser His Leu Pro Asp Arg Val
                820                 825                 830

His Phe Ala Ser Pro Leu His Val Ala Trp Arg Pro Pro
                835                 840                 845

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

Ser Tyr Gln His Phe Arg Lys Leu Leu Leu
1               5                   10

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Arg Leu Lys Leu Ile Met Pro Ala Arg
1               5

(2) INFORMATION FOR SEQ ID NO: 14:

(i) SEQUENCE CHARACTERISTICS:
        (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 14:

Val Val Asn His Tyr Phe Gln Thr Arg
1               5

(2) INFORMATION FOR SEQ ID NO: 15:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 15:

His Thr Leu Trp Lys Ala Gly Ile Leu Tyr
1               5                  10

(2) INFORMATION FOR SEQ ID NO: 16:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Thr Leu Trp Lys Ala Gly Ile Leu Tyr Lys
1               5                  10

(2) INFORMATION FOR SEQ ID NO: 17:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Leu Tyr Ser His Pro Ile Ile Leu Gly Phe
1               5                  10

(2) INFORMATION FOR SEQ ID NO: 18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 18:

Tyr Met Asp Asp Val Val Leu Gly Ala
1               5

(2) INFORMATION FOR SEQ ID NO: 19:

(i) SEQUENCE CHARACTERISTICS:
```

(A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 19:

Phe Leu Leu Ser Leu Gly Ile His Leu
1               5

(2) INFORMATION FOR SEQ ID NO: 20:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Ala Leu Met Pro Leu Tyr Ala Cys Ile
1               5

(2) INFORMATION FOR SEQ ID NO: 21:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 21:

Gly Thr Asp Asn Ser Val Val Leu Ser Arg
1               5                   10

(2) INFORMATION FOR SEQ ID NO: 22:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 22:

Lys Tyr Thr Ser Phe Pro Trp Leu Leu
1               5

(2) INFORMATION FOR SEQ ID NO: 23:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Trp Ile Leu Arg Gly Thr Ser Phe Arg
1               5

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Asp Leu Asn Leu Gly Asn Leu Asn Val
1               5

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Phe Leu Pro Ser Asp Tyr Phe Pro Ser Val
1               5                   10

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Leu Leu Ala Gln Phe Thr Ser Ala Ile
1               5

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Lys Leu His Leu Tyr Ser His Pro Ile
1               5

(2) INFORMATION FOR SEQ ID NO: 28:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Ala Leu Met Pro Leu Tyr Ala Cys Ile
1               5

(2) INFORMATION FOR SEQ ID NO: 29:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

His Leu Tyr Ser His Pro Ile Ile Leu
1               5

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Phe Leu Leu Ala Gln Phe Thr Ser Ala Ile
1               5                   10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Tyr Leu His Thr Leu Trp Lys Ala Gly Ile
1               5                   10

(2) INFORMATION FOR SEQ ID NO: 32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Trp Ile Leu Arg Gly Thr Ser Phe Val
1               5

(2) INFORMATION FOR SEQ ID NO: 33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Leu Leu Gly Cys Ala Ala Asn Trp Ile Leu
1               5                   10

(2) INFORMATION FOR SEQ ID NO: 34:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Asn Leu Ser Trp Leu Ser Leu Asp Val
1              5

(2) INFORMATION FOR SEQ ID NO: 35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Phe Leu Pro Ser Asp Phe Pro Pro Ser Val
1              5                  10

(2) INFORMATION FOR SEQ ID NO: 36:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Trp Leu Ser Leu Leu Val Pro Phe Val
1              5

(2) INFORMATION FOR SEQ ID NO: 37:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Lys Leu Val Ala Leu Gly Ile Asn Ala Val
1              5                  10

(2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Gly Leu Pro Arg Tyr Val Ala Arg Leu
1              5

(2) INFORMATION FOR SEQ ID NO: 39:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Ser Gly Leu Ser Arg Tyr Val Ala Arg Leu
1               5                   10

(2) INFORMATION FOR SEQ ID NO: 40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Gly Leu Ser Arg Tyr Val Ala Arg Leu Ser
1               5                   10

(2) INFORMATION FOR SEQ ID NO: 41:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Gly Val Ser Arg Tyr Val Ala Arg Leu
1               5

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Gly Leu Pro Arg Tyr Val Ala Arg Leu
1               5

(2) INFORMATION FOR SEQ ID NO: 43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Gly Leu Pro Arg Tyr Val Val Cys Leu
1               5

(2) INFORMATION FOR SEQ ID NO: 44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

```
Gly Leu Ser Arg Tyr Val Val Cys Leu
1               5
```

(2) INFORMATION FOR SEQ ID NO: 45:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 45:

```
Met Pro Leu Ser Tyr Gln His Phe Arg Lys Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
                35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
                100                 105                 110

Ala Arg Phe Tyr Pro Asn Leu Thr Lys Tyr Leu Pro Leu Asp Lys Gly
                115                 120                 125

Ile Lys Pro Tyr Tyr Pro Glu His Ala Val Asn His Tyr Phe Lys Thr
                130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
                180                 185                 190

Gly Asp Glu Ser Phe Cys Ser Gln Ser Ser Gly Ile Leu Ser Arg Ser
                195                 200                 205

Pro Val Gly Pro Cys Val Arg Ser Gln Leu Lys Gln Ser Arg Leu Gly
                210                 215                 220

Leu Gln Pro Gln Gln Gly Ser Met Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Thr
```

-continued

```
                260                 265                 270
Ser Ser Cys Leu His Gln Ser Ala Val Arg Lys Thr Ala Tyr Ser His
            275                 280                 285

Leu Ser Thr Ser Lys Arg Gln Ser Ser Gly His Ala Val Glu Phe
290                 295                 300

His Asn Ile Pro Pro Ser Ser Ala Arg Ser Gln Ser Glu Gly Pro Ile
305                 310                 315                 320

Phe Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
            355                 360                 365

Val Thr Gly Gly Val Phe Leu Val Asp Lys Asn Pro His Asn Thr Thr
370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
                420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
            450                 455                 460

Ser Arg Asn Ile Asn His Gln His Gly Ala Met Gln Asp Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
            595                 600                 605

Glu His Ile Val Leu Lys Leu Lys Gln Cys Phe Arg Lys Leu Pro Val
610                 615                 620

Asn Ser Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Lys Gln Tyr Leu Asn Leu Tyr Pro Val Ala
            675                 680                 685
```

```
Arg Gln Arg Ser Gly Leu Cys Gln Val Phe Ala Asp Ala Thr Pro Thr
    690                 695                 700

Gly Trp Gly Leu Ala Ile Gly His Arg Met Arg Gly Thr Phe Val
705                 710                 715                 720

Ala Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Leu Leu Pro Phe Arg Pro Thr Thr Gly Arg Thr Ser Leu Tyr
                805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
        835                 840

(2) INFORMATION FOR SEQ ID NO: 46:

(i) SEQUENCE CHARACTERISTICS:
         (A) LENGTH: 845 amino acids
         (B) TYPE: amino acid
         (C) STRANDEDNESS: <Unknown>
         (D) TOPOLOGY: linear (ii) MOLECULE TYPE: protein (ix) FEATURE:
         (A) NAME/KEY: Modified-site
         (B) LOCATION: 16..18
         (D) OTHER INFORMATION: /product= "OTHER"
             /note= "Xaa = unknown"

(xi) SEQUENCE DESCRIPTION: SEQ ID NO: 46:

Met Pro Leu Ser Tyr Gln His Phe Arg Lys Leu Leu Leu Leu Asp Xaa
1               5                   10                  15

Xaa Xaa Glu Ala Gly Pro Leu Glu Glu Glu Leu Pro Arg Leu Ala Asp
            20                  25                  30

Glu Gly Leu Asn Arg Arg Val Ala Glu Asp Leu Asn Leu Gly Asn Leu
        35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro His Ile His Leu Gln Glu Asp Ile Ile Asn Arg Cys Gln Gln
                85                  90                  95

Tyr Val Gly Pro Leu Thr Val Asn Glu Lys Arg Arg Leu Lys Leu Ile
            100                 105                 110

Met Pro Ala Arg Phe Tyr Pro Asn Leu Thr Lys Tyr Leu Pro Leu Asp
        115                 120                 125

Lys Gly Ile Lys Pro Tyr Tyr Pro Glu His Ala Val Asn His Tyr Phe
    130                 135                 140

Lys Thr Arg His Tyr Leu His Thr Leu Trp Lys Ala Gly Ile Leu Tyr
145                 150                 155                 160
```

```
Lys Arg Glu Thr Thr Arg Ser Ala Ser Phe Cys Gly Ser Pro Tyr Ser
                165                 170                 175
Trp Glu Gln Glu Leu Gln His Gly Arg Leu Val Phe Gln Thr Ser Thr
            180                 185                 190
Arg His Gly Asp Glu Ser Phe Cys Ser Gln Ser Ser Gly Ile Leu Ser
        195                 200                 205
Arg Ser Pro Val Gly Pro Cys Val Arg Ser Gln Leu Lys Gln Ser Arg
    210                 215                 220
Leu Gly Leu Gln Pro Gln Gln Gly Ser Leu Ala Arg Gly Lys Ser Gly
225                 230                 235                 240
Arg Ser Gly Ser Ile Arg Ala Arg Val His Pro Thr Thr Arg Arg Ser
                245                 250                 255
Phe Gly Val Glu Pro Ser Gly Ser Gly His Ile Asp Asn Ser Ala Ser
            260                 265                 270
Ser Thr Ser Ser Cys Leu His Gln Ser Ala Val Arg Lys Thr Ala Tyr
        275                 280                 285
Ser His Leu Ser Thr Ser Lys Arg Gln Ser Ser Gly His Ala Val
    290                 295                 300
Glu Leu His Asn Ile Pro Pro Ser Ser Ala Arg Pro Gln Ser Glu Gly
305                 310                 315                 320
Pro Ile Leu Ser Cys Trp Trp Leu Gln Phe Arg Asn Ser Lys Pro Cys
                325                 330                 335
Ser Asp Tyr Cys Leu Thr His Ile Val Asn Leu Leu Glu Asp Trp Gly
            340                 345                 350
Pro Cys Thr Glu His Gly Glu His Asn Ile Arg Ile Pro Arg Thr Pro
        355                 360                 365
Ala Arg Val Thr Gly Gly Val Phe Leu Val Asp Lys Asn Pro His Asn
    370                 375                 380
Thr Thr Glu Ser Thr Leu Val Val Asp Phe Ser Gln Phe Ser Arg Gly
385                 390                 395                 400
Ser Thr His Val Ser Trp Pro Lys Phe Ala Val Pro Asn Leu Gln Ser
                405                 410                 415
Leu Thr Asn Leu Leu Ser Ser Asn Leu Ser Trp Leu Ser Leu Asp Val
            420                 425                 430
Ser Ala Ala Phe Tyr His Ile Pro Leu His Pro Ala Ala Met Pro His
        435                 440                 445
Leu Leu Val Gly Ser Ser Gly Leu Pro Arg Tyr Val Val Cys Leu Ser
    450                 455                 460
Ser Thr Ser Lys Asn Ile Asn Tyr Gln His Gly Thr Met Gln Asp Leu
465                 470                 475                 480
His Asp Ser Cys Ser Arg Asn Leu Tyr Val Ser Leu Phe Leu Leu Tyr
                485                 490                 495
Lys Thr Phe Gly Arg Lys Leu His Leu Tyr Ser His Pro Ile Ile Leu
            500                 505                 510
Gly Phe Arg Lys Ile Pro Met Gly Val Gly Leu Ser Pro Phe Leu Leu
        515                 520                 525
Ala Gln Phe Thr Ser Ala Ile Cys Ser Val Val Arg Arg Ala Phe Pro
    530                 535                 540
His Cys Leu Ala Phe Ser Tyr Met Asp Asp Val Val Leu Gly Ala Lys
545                 550                 555                 560
Ser Val Gln His Leu Glu Ser Leu Phe Thr Ser Ile Thr Asn Phe Leu
                565                 570                 575
```

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Cys Trp Gly Thr Leu
            595                 600                 605

Pro Gln Glu His Ile Val Leu Lys Ile Lys Gln Cys Phe Arg Lys Leu
            610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
            645                 650                 655

Met Pro Leu Tyr Ala Cys Ile Gln Ser Lys Gln Ala Phe Thr Phe Ser
            660                 665                 670

Pro Thr Tyr Lys Ala Phe Leu Cys Lys Gln Tyr Leu Asn Leu Tyr Pro
            675                 680                 685

Val Ala Arg Gln Arg Ser Gly Leu Cys Gln Val Phe Ala Asp Ala Thr
            690                 695                 700

Pro Thr Gly Trp Gly Leu Ala Ile Gly His Arg Arg Met Arg Gly Thr
705                 710                 715                 720

Phe Val Ala Pro Leu Pro Ile His Thr Ala Glu Leu Ala Ala Cys
            725                 730                 735

Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
            755                 760                 765

Ala Ala Asn Trp Ile Leu Arg Gly Thr Ser Phe Val Tyr Val Pro Ser
770                 775                 780

Ala Leu Asn Pro Ala Asp Asp Pro Ser Arg Gly Arg Leu Gly Leu Tyr
785                 790                 795                 800

Arg Pro Leu Leu His Leu Pro Phe Arg Pro Thr Thr Gly Arg Thr Ser
            805                 810                 815

Leu Tyr Ala Val Ser Pro Ser Val Pro Ser His Leu Pro Asp Arg Val
            820                 825                 830

His Phe Pro Ser Pro Leu His Val Ala Trp Arg Pro
            835                 840                 845

(2) INFORMATION FOR SEQ ID NO: 47:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 47:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
            50                  55                  60

Ser Thr Val Pro Val Leu Asn Pro Glu Ser Gln Thr Pro Ser Phe Pro
65                  70                  75                  80

-continued

```
Asn Ile His Leu Gln Glu Asp Ile Ile Asn Arg Cys Gln Gln Tyr Val
             85                  90                  95
Gly Pro Leu Thr Val Asn Glu Lys Arg Arg Leu Lys Leu Ile Met Pro
            100                 105                 110
Ala Arg Phe Tyr Pro Asn Leu Thr Lys Tyr Leu Pro Leu Asp Lys Gly
            115                 120                 125
Ile Lys Pro Tyr Tyr Pro Glu His Ala Val Asn His Tyr Phe Lys Thr
130                 135                 140
Arg His Tyr Leu His Thr Leu Trp Lys Ala Gly Ile Leu Tyr Lys Arg
145                 150                 155                 160
Glu Thr Thr Arg Ser Ala Ser Phe Cys Gly Ser Pro Tyr Ser Trp Glu
                165                 170                 175
Gln Glu Leu Arg His Gly Arg Leu Val Phe Gln Thr Ser Thr Arg His
            180                 185                 190
Gly Asp Glu Ser Phe Cys Ser Gln Ser Ser Gly Ile Leu Ser Arg Ser
            195                 200                 205
Pro Val Gly Pro Cys Val Arg Ser Gln Leu Lys Gln Ser Arg Leu Gly
            210                 215                 220
Leu Gln Pro Gln Gln Gly Ser Leu Ala Arg Gly Asn Gln Gly Arg Ser
225                 230                 235                 240
Gly Arg Leu Arg Ala Arg Val His Pro Thr Thr Arg Arg Ser Phe Gly
                245                 250                 255
Val Glu Pro Ser Gly Ser Gly His Ile Asp Asn Ser Ala Ser Ser Ala
            260                 265                 270
Ser Ser Cys Phe His Gln Ser Ala Val Arg Lys Thr Ala Tyr Ser His
            275                 280                 285
Leu Ser Thr Ser Lys Arg Gln Ser Ser Ser Gly His Ala Val Glu Leu
290                 295                 300
His Asn Ile Pro Pro Ser Ser Ala Arg Ser Gln Ser Glu Gly Pro Ile
305                 310                 315                 320
Phe Ser Cys Trp Trp Leu Gln Phe Arg Asn Ser Lys Pro Cys Ser Asp
                325                 330                 335
Tyr Cys Leu Thr His Ile Val Asn Leu Leu Glu Asp Trp Gly Pro Cys
            340                 345                 350
Thr Glu His Gly Glu His Asn Ile Arg Ile Pro Arg Thr Pro Ala Arg
            355                 360                 365
Val Thr Gly Gly Val Phe Leu Val Asp Lys Asn Pro His Asn Thr Thr
370                 375                 380
Glu Ser Arg Leu Val Val Asp Phe Ser Gln Phe Ser Arg Gly Ser Thr
385                 390                 395                 400
His Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
            420                 425                 430
Ala Phe Tyr His Ile Pro Leu His Pro Ala Ala Met Pro His Leu Leu
            435                 440                 445
Val Gly Ser Ser Gly Leu Pro Arg Tyr Val Ala Arg Leu Ser Ser Thr
450                 455                 460
Ser Arg Asn Ile Asn Tyr Gln His Gly Thr Met Gln Asp Leu His Asp
465                 470                 475                 480
Ser Cys Ser Arg Asn Leu Tyr Val Ser Leu Leu Leu Leu Tyr Lys Thr
                485                 490                 495
Phe Gly Arg Lys Leu His Leu Tyr Ser His Pro Ile Ile Leu Gly Phe
```

```
                500             505             510
Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
        530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Leu Lys Leu Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Gln Gln Tyr Leu His Leu Tyr Pro Val Ala
        675                 680                 685

Arg Gln Arg Ser Gly Leu Cys Gln Val Phe Ala Asp Ala Thr Pro Thr
    690                 695                 700

Gly Trp Gly Leu Ala Ile Gly His Arg Arg Met Arg Gly Thr Phe Val
705                 710                 715                 720

Val Pro Leu Pro Ile His Thr Ala Glu Leu Leu Ala Ala Cys Phe Ala
                725                 730                 735

Arg Asp Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Ser Leu Pro Phe Gln Pro Thr Thr Gly Arg Thr Ser Leu Tyr
                805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
        835                 840
```

(2) INFORMATION FOR SEQ ID NO: 48:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 48:

Met Pro Leu Ser Tyr Gln His Phe Arg Lys Leu Leu Leu Leu Asp Asp

-continued

```
1               5                   10                  15

Glu Ala Gly Pro Leu Glu Glu Leu Pro Arg Leu Ala Asp Glu Gly
            20              25              30

Leu Asn Arg Arg Val Ala Glu Asp Leu Asn Leu Gly Asn Leu Asn Val
        35              40              45

Ser Ile Pro Trp Thr His Lys Val Gly Asn Phe Thr Gly Leu Tyr Ser
50              55              60

Ser Thr Val Pro Val Phe Asn Pro Glu Trp Gln Thr Pro Ser Phe Pro
65              70              75              80

Asn Ile His Leu Gln Glu Asp Ile Ile Asn Arg Cys Gln Gln Tyr Val
            85              90              95

Gly Pro Leu Thr Val Asn Glu Lys Arg Arg Leu Lys Leu Ile Met Pro
            100             105             110

Ala Arg Phe Tyr Pro Asn Leu Thr Lys Tyr Leu Pro Leu Asp Lys Gly
            115             120             125

Ile Lys Pro Tyr Tyr Pro Glu His Ala Val Asn His Tyr Phe Lys Thr
            130             135             140

Arg His Tyr Leu His Thr Leu Trp Lys Ala Gly Ile Leu Tyr Lys Arg
145             150             155             160

Glu Thr Thr Arg Ser Ala Ser Phe Cys Gly Ser Pro Tyr Ser Trp Glu
                165             170             175

Gln Glu Leu Gln His Gly Arg Leu Val Phe Gln Thr Ser Thr Arg His
            180             185             190

Gly Asp Glu Ser Phe Cys Ser Gln Ser Ser Gly Ile Leu Ser Arg Ser
            195             200             205

Pro Val Gly Pro Cys Ile Arg Ser Gln Leu Lys Gln Ser Arg Leu Gly
    210             215             220

Leu Gln Pro Gln Gln Gly Ser Leu Ala Arg Gly Lys Ser Gly Arg Ser
225             230             235             240

Gly Ser Ile Trp Ala Arg Val His Pro Thr Thr Arg Arg Ser Phe Gly
                245             250             255

Val Glu Pro Ser Gly Ser Gly His Ile Asp Asn Ser Ala Ser Ser Ala
            260             265             270

Ser Ser Cys Leu Tyr Gln Ser Ala Val Arg Lys Thr Ala Tyr Ser His
            275             280             285

Leu Ser Thr Ser Lys Arg Gln Ser Ser Ser Gly His Ala Val Glu Leu
            290             295             300

His Asn Ile Pro Pro Ser Cys Ala Arg Ser Gln Ser Glu Gly Pro Ile
305             310             315             320

Ser Ser Cys Trp Trp Leu Gln Phe Arg Asn Ser Glu Pro Cys Ser Asp
                325             330             335

Tyr Cys Leu Thr His Ile Val Asn Leu Leu Glu Asp Trp Gly Pro Cys
            340             345             350

Thr Glu His Gly Glu His Asn Ile Arg Ile Pro Arg Thr Pro Ala Arg
            355             360             365

Val Thr Gly Gly Val Phe Leu Val Asp Lys Asn Pro His Asn Thr Thr
            370             375             380

Glu Ser Arg Leu Val Val Asp Phe Ser Gln Phe Ser Arg Gly Ser Thr
385             390             395             400

His Val Ser Trp Pro Lys Phe Ala Val Pro Asn Leu Gln Ser Leu Thr
                405             410             415

Asn Leu Leu Ser Ser Asn Leu Ser Trp Leu Ser Leu Asp Val Ser Ala
            420             425             430
```

```
Ala Phe Tyr His Ile Pro Leu His Pro Ala Ala Met Pro His Leu Leu
        435                 440                 445
Val Gly Ser Ser Gly Leu Pro Arg Tyr Val Ala Arg Leu Ser Ser Thr
450                 455                 460
Ser Arg Asn Ile Asn Tyr Gln His Gly Thr Met Gln Asp Leu His Asp
465                 470                 475                 480
Ser Cys Ser Arg Asn Leu Tyr Val Ser Leu Leu Leu Tyr Lys Thr
                485                 490                 495
Phe Gly Arg Lys Leu His Leu Tyr Ser His Pro Ile Ile Leu Gly Phe
                500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
        530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
                565                 570                 575
Leu Gly Ile His Leu Asn Pro His Lys Thr Lys Arg Trp Gly Tyr Ser
                580                 585                 590
Leu Asn Phe Met Gly Tyr Val Ile Gly Ser Trp Gly Thr Leu Pro Gln
        595                 600                 605
Glu His Ile Val Leu Lys Ile Lys Gln Cys Phe Arg Lys Leu Pro Val
        610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
                660                 665                 670
Tyr Lys Ala Phe Leu Cys Lys Gln Tyr Leu His Leu Tyr Pro Val Ala
                675                 680                 685
Arg Gln Arg Ser Gly Leu Cys Gln Val Phe Ala Asp Ala Thr Pro Thr
        690                 695                 700
Gly Trp Gly Leu Ala Ile Gly Gln Ser Gly Met Arg Gly Thr Phe Val
705                 710                 715                 720
Ala Pro Leu Pro Ile His Thr Ala Glu Leu Leu Ala Ala Cys Phe Ala
                725                 730                 735
Arg Ser Arg Ser Gly Ala Lys Leu Ile Gly Thr Asp Asn Ser Val Val
                740                 745                 750
Leu Ser Arg Lys Tyr Thr Ser Phe Pro Trp Leu Leu Gly Cys Ala Ala
                755                 760                 765
Asn Trp Ile Leu Arg Gly Thr Ser Phe Val Tyr Val Pro Ser Ala Leu
        770                 775                 780
Asn Pro Ala Asp Asp Pro Ser Arg Gly Arg Leu Gly Leu Tyr Arg Pro
785                 790                 795                 800
Leu Leu His Leu Pro Phe Arg Pro Thr Thr Gly Arg Ala Ser Leu Tyr
                805                 810                 815
Ala Val Ser Pro Ser Val Pro Ser His Leu Pro Val Arg Val His Phe
                820                 825                 830
Ala Ser Pro Leu His Val Ala Trp Arg Pro Pro
                835                 840
```

(2) INFORMATION FOR SEQ ID NO: 49:

(i) SEQUENCE CHARACTERISTICS:
        (A) LENGTH: 730 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 49:

```
Met Pro Leu Ser Tyr Gln His Phe Arg Lys Leu Leu Leu Asp Asp
 1               5                  10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
                35                  40                  45

Ser Ile Pro Trp Thr His Lys Val Gly Asn Phe Thr Gly Leu Tyr Ser
 50                  55                  60

Ser Thr Val Pro Val Phe Asn Pro Glu Trp Gln Thr Pro Ser Phe Pro
 65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
                100                 105                 110

Ala Arg Phe Tyr Pro Asn Leu Thr Lys Tyr Leu Pro Leu Asp Lys Gly
                115                 120                 125

Ile Lys Pro Tyr Tyr Pro Glu His Ala Val Asn His Tyr Phe Lys Thr
 130                 135                 140

Arg His Tyr Leu His Thr Leu Trp Lys Ala Gly Ile Leu Tyr Lys Arg
 145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
                180                 185                 190

Gly Asp Glu Ser Phe Cys Ser Gln Ser Ser Gly Ile Leu Ser Arg Ser
                195                 200                 205

Pro Val Gly Pro Cys Val Arg Ser Gln Leu Thr Gln Ser Arg Leu Gly
 210                 215                 220

Leu Gln Pro Gln Gln Gly Ser Leu Ala Arg Gly Lys Ser Gly Arg Ser
 225                 230                 235                 240

Gly Ser Ile Arg Ala Arg Val His Pro Thr Thr Arg Arg Ser Phe Gly
                245                 250                 255

Val Glu Pro Ala Gly Ser Gly Arg Ile Asp Asn Arg Ala Ser Ser Thr
                260                 265                 270

Ser Ser Cys Leu His Gln Ser Ala Val Arg Lys Thr Ala Tyr Ser His
                275                 280                 285

Leu Ser Thr Ser Lys Arg Gln Ser Ser Ser Gly His Ala Val Glu Leu
                290                 295                 300

His Asn Ile Pro Pro Ser Ser Ala Arg Pro Gln Ser Glu Gly Pro Ile
 305                 310                 315                 320

Leu Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
                340                 345                 350
```

```
Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asp Leu His Asp
465                 470                 475                 480

Ser Cys Ser Arg Asn Leu Tyr Val Ser Leu Leu Leu Tyr Lys Thr
                485                 490                 495

Phe Gly Arg Lys Leu His Leu Tyr Ser His Pro Ile Ile Leu Gly Phe
                500                 505                 510

Arg Lys Ile Pro Met Gly Gly Leu Ser Pro Phe Leu Leu Ala Gln
            515                 520                 525

Phe Thr Ser Ala Ile Cys Ser Val Val Arg Arg Ala Phe Pro His Cys
    530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Cys Trp Gly Thr Leu Pro Gln
            595                 600                 605

Glu His Ile Val Leu Lys Ile Lys Gln Cys Phe Arg Lys Leu Pro Val
    610                 615                 620

Asn Arg Pro Ile Asp Trp Lys Val Cys Gln Arg Leu Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Lys Gln Tyr Leu Asn Leu Tyr Pro Val Ala
            675                 680                 685

Arg Gln Arg Ser Gly Leu Cys Gln Val Phe Ala Asp Ala Thr Pro Thr
    690                 695                 700

Gly Trp Gly Leu Ala Ile Gly His Ser Arg Met Arg Gly Pro Leu Trp
705                 710                 715                 720

Leu Leu Cys Arg Ser Ile Leu Arg Asn Ser
                725                 730

(2) INFORMATION FOR SEQ ID NO: 50:

(i) SEQUENCE CHARACTERISTICS:
        (A) LENGTH: 842 amino acids
        (B) TYPE: amino acid
        (C) STRANDEDNESS: <Unknown>
```

(D) TOPOLOGY: linear (ii) MOLECULE TYPE: protein (xi) SEQUENCE DESCRIPTION: SEQ ID NO: 50:

```
Met Pro Leu Ser Tyr Gln His Phe Arg Lys Leu Leu Leu Leu Asp Asp
1               5                   10                  15

Glu Ala Gly Pro Leu Glu Glu Leu Pro Arg Leu Ala Asp Glu Asp
            20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
                100                 105                 110

Ala Arg Phe Tyr Pro Lys Leu Thr Lys Tyr Leu Pro Leu Asp Lys Gly
            115                 120                 125

Ile Lys Pro Tyr Tyr Pro Glu His Ala Val Asn His Tyr Phe Lys Thr
            130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
            195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val Pro Pro Thr Thr Arg Arg Ser Phe Gly
                245                 250                 255

Val Glu Pro Ser Gly Ser Gly His Ile Asp Asn Arg Ala Ser Ser Thr
            260                 265                 270

Ser Ser Cys Leu His Gln Ser Ala Val Arg Lys Thr Ala Tyr Ser His
            275                 280                 285

Leu Ser Thr Ser Lys Arg Gln Ser Ser Ser Gly His Ala Val Glu Leu
290                 295                 300

His His Ile Ser Pro Ser Pro Ala Arg Ser Gln Ser Glu Gly Pro Ile
305                 310                 315                 320

Phe Ser Ser Trp Trp Leu Gln Phe Arg Asn Ser Lys Pro Cys Cys Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
            355                 360                 365

Val Thr Gly Gly Val Phe Leu Val Asp Lys Asn Pro His Asn Thr Thr
            370                 375                 380

Glu Ser Arg Leu Val Val Asp Phe Ser Gln Phe Ser Arg Gly Ser Thr
```

-continued

```
385                 390                 395                 400

His Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
                420                 425                 430
Ala Phe Tyr His Ile Pro Leu His Pro Ala Ala Met Pro His Leu Leu
                435                 440                 445
Val Gly Ser Ser Gly Leu Pro Arg Tyr Val Ala Arg Leu Ser Ser Thr
                450                 455                 460
Ser Arg Asn Ile Asn His Gln His Gly Thr Met Gln Asp Leu His Asp
465                 470                 475                 480
Ser Cys Ser Arg Asn Leu Tyr Val Ser Leu Leu Leu Tyr Lys Thr
                485                 490                 495
Phe Gly Arg Lys Leu His Leu Tyr Ser His Pro Ile Ile Leu Gly Phe
                500                 505                 510
Arg Lys Ile Pro Met Gly Gly Gly Leu Ser Pro Phe Leu Leu Ala Gln
                515                 520                 525
Phe Thr Ser Ala Ile Cys Ser Val Val Arg Arg Ala Phe Pro His Cys
                530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
                565                 570                 575
Leu Gly Ile His Leu Asn Pro Asn Lys Thr Lys Arg Trp Gly Tyr Ser
                580                 585                 590
Leu Asn Phe Met Gly Tyr Val Ile Gly Ser Trp Gly Thr Leu Pro Gln
                595                 600                 605
Glu His Ile Val Leu Lys Ile Lys Gln Cys Phe Arg Lys Leu Pro Val
                610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
                660                 665                 670
Tyr Lys Ala Phe Leu Cys Lys Gln Tyr Leu His Leu Tyr Pro Val Ala
                675                 680                 685
Arg Arg Thr Ala Leu Cys Gln Val Phe Ala Asp Ala Thr Pro Thr Gly
                690                 695                 700
Trp Gly Leu Ala Ile Gly His Arg Arg Met Arg Gly Thr Phe Val Ala
705                 710                 715                 720
Pro Leu Pro Ile His Thr Ala Glu Leu Leu Ala Ala Cys Phe Ala Arg
                725                 730                 735
Ser Arg Ser Gly Ala Lys Leu Ile Gly Thr Asp Asn Ser Val Val Leu
                740                 745                 750
Ser Arg Lys Tyr Thr Ser Phe Pro Trp Leu Leu Gly Cys Ala Ala Asn
                755                 760                 765
Trp Ile Leu Arg Gly Thr Tyr Phe Val Tyr Val Pro Ser Ala Leu Asn
770                 775                 780
Pro Ala Asp Asp Pro Ser Arg Gly Arg Leu Gly Leu Ile Arg Pro Leu
785                 790                 795                 800
Leu His Leu Arg Phe Arg Pro Thr Thr Gly Arg Thr Ser Leu Tyr Ala
                805                 810                 815
```

Val Ser Pro Ser Val Pro Ser His Leu Pro Asp Arg Val His Phe Ala
            820                 825                 830

Ser Pro Leu His Val Ala Trp Arg Pro Pro
            835                 840

(2) INFORMATION FOR SEQ ID NO: 51:

(i) SEQUENCE CHARACTERISTICS:
        (A) LENGTH: 842 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 51:

Met Pro Leu Ser Tyr Gln His Phe Arg Lys Leu Leu Leu Asp Asp
1               5                   10                  15

Glu Ala Gly Pro Leu Glu Glu Leu Pro Arg Leu Ala Asp Glu Asp
                20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
                100                 105                 110

Ala Arg Phe Tyr Pro Lys Leu Thr Lys Tyr Leu Pro Leu Asp Lys Gly
                115                 120                 125

Ile Lys Pro Tyr Tyr Pro Glu His Ala Val Asn His Tyr Phe Lys Thr
        130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
                180                 185                 190

Gly Asp Glu Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
        210                 215                 220

Leu Gln Pro Gln Gln Gly Ser Leu Ala Arg Gly Lys Ser Gly Arg Ser
225                 230                 235                 240

Gly Ser Ile Arg Ala Arg Val Pro Pro Thr Thr Arg Arg Ser Phe Gly
                245                 250                 255

Val Glu Pro Ser Gly Ser Gly His Ile Asp Asn Arg Ala Ser Ser Thr
                260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Gly His Ala Val Glu Leu
        290                 295                 300

His His Ile Ser Pro Ser Pro Ala Arg Ser Gln Ser Glu Gly Pro Ile
305                 310                 315                 320

-continued

```
Phe Ser Ser Trp Trp Leu Gln Phe Arg Asn Ser Lys Pro Cys Ser Asp
            325                 330                 335
Tyr Cys Leu Thr His Ile Val Asn Leu Leu Glu Asp Trp Gly Pro Cys
            340                 345                 350
Thr Glu His Gly Glu His Asn Ile Arg Ile Pro Arg Thr Pro Ala Arg
            355                 360                 365
Val Thr Gly Gly Val Phe Leu Val Asp Lys Asn Pro His Asn Thr Thr
    370                 375                 380
Glu Ser Arg Leu Val Val Asp Phe Ser Gln Phe Ser Arg Gly Ser Thr
385                 390                 395                 400
His Val Ser Trp Pro Lys Phe Ala Val Pro Asn Leu Gln Ser Leu Thr
            405                 410                 415
Asn Leu Leu Ser Ser Asn Leu Ser Trp Leu Ser Leu Asp Val Ser Ala
            420                 425                 430
Ala Phe Tyr His Ile Pro Leu His Pro Ala Ala Met Pro His Leu Leu
            435                 440                 445
Val Gly Ser Ser Gly Leu Pro Arg Tyr Val Ala Arg Leu Ser Ser Thr
    450                 455                 460
Ser Arg Asn Ile Asn His Gln His Gly Thr Met Gln Asp Leu His Asp
465                 470                 475                 480
Ser Cys Ser Arg Asn Leu Tyr Val Ser Leu Leu Leu Tyr Lys Thr
            485                 490                 495
Phe Gly Arg Lys Leu His Leu Tyr Ser His Pro Ile Ile Leu Gly Phe
            500                 505                 510
Arg Lys Ile Pro Met Gly Gly Gly Leu Ser Pro Phe Leu Leu Ala Gln
            515                 520                 525
Phe Thr Ser Ala Ile Cys Ser Val Val Arg Arg Ala Phe Pro His Cys
            530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
            565                 570                 575
Leu Gly Ile His Leu Asn Pro Asn Lys Thr Lys Arg Trp Gly Tyr Ser
            580                 585                 590
Leu Asn Phe Met Gly Tyr Val Ile Gly Ser Trp Gly Thr Leu Pro Gln
            595                 600                 605
Glu His Ile Val Leu Lys Ile Lys Gln Cys Phe Arg Lys Leu Pro Val
            610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
            645                 650                 655
Leu Tyr Ala Cys Ile Gln Ser Lys Gln Ala Phe Thr Phe Ser Pro Thr
            660                 665                 670
Tyr Lys Ala Phe Leu Cys Lys Gln Tyr Leu His Leu Tyr Pro Val Ala
            675                 680                 685
Arg Arg Thr Ala Leu Cys Gln Val Phe Ala Asp Ala Thr Pro Thr Gly
    690                 695                 700
Trp Gly Leu Ala Ile Gly His Arg Arg Met Arg Gly Thr Phe Val Ala
705                 710                 715                 720
Pro Leu Pro Ile His Thr Ala Glu Leu Leu Ala Ala Cys Phe Ala Arg
            725                 730                 735
```

```
Ser Arg Ser Gly Ala Lys Leu Ile Gly Thr Asp Asn Ser Val Val Leu
        740                 745                 750

Ser Arg Lys Tyr Thr Ser Phe Pro Trp Leu Leu Gly Cys Ala Ala Asn
        755                 760                 765

Trp Ile Leu Arg Gly Thr Tyr Phe Val Tyr Val Pro Ser Ala Leu Asn
        770                 775                 780

Pro Ala Asp Asp Pro Ser Arg Gly Arg Leu Gly Leu Ile Arg Pro Leu
785                 790                 795                 800

Leu His Leu Arg Phe Arg Pro Thr Thr Gly Arg Thr Ser Leu Tyr Ala
                805                 810                 815

Val Ser Pro Ser Val Pro Ser His Leu Pro Asp Arg Val His Phe Ala
                820                 825                 830

Ser Pro Leu His Val Ala Trp Arg Pro Pro
        835                 840
```

(2) INFORMATION FOR SEQ ID NO: 52:

(i) SEQUENCE CHARACTERISTICS:
        (A) LENGTH: 481 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 52:

```
Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
                20                  25                  30

Ala Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Thr His Thr Lys Tyr Leu Pro Leu Asp
            115                 120                 125

Lys Gly Ile Lys Pro Tyr Tyr Pro Asp Gln Val Val Asn His Tyr Phe
    130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Ser Gln Arg His Gly Asp Glu Ser Phe
            180                 185                 190

Cys Ser Gln Ser Ser Gly Ile Pro Ser Arg Ser Ser Val Gly Pro Cys
            195                 200                 205

Ile Arg Ser Gln Leu Asn Lys Ser Arg Leu Gly Leu Gln Pro His Gln
    210                 215                 220

Gly Pro Leu Ala Ser Ser Gln Pro Gly Arg Ser Gly Ser Ile Arg Ala
225                 230                 235                 240
```

```
Arg Ala His Pro Ser Thr Arg Arg Tyr Phe Gly Val Glu Pro Ser Gly
            245                 250                 255

Ser Gly His Ile Asp His Ser Val Asn Asn Ser Ser Cys Leu His
            260                 265                 270

Gln Ser Ala Val Arg Lys Ala Ala Tyr Ser His Leu Ser Thr Ser Lys
            275                 280                 285

Arg Gln Ser Ser Gly His Ala Val Glu Phe His Cys Leu Ala Pro
    290                 295                 300

Ser Ser Ala Gly Ser Gln Ser Gln Gly Ser Val Ser Ser Cys Trp Trp
305                 310                 315                 320

Leu Gln Phe Arg Asn Ser Lys Pro Cys Ser Glu Tyr Cys Leu Ser His
            325                 330                 335

Leu Val Asn Leu Arg Glu Asp Trp Gly Pro Cys Asp Asp His Gly Glu
            340                 345                 350

His His Ile Arg Ile Pro Arg Thr Pro Ala Arg Val Thr Gly Gly Val
            355                 360                 365

Phe Leu Val Asp Lys Asn Pro His Asn Thr Ala Glu Ser Arg Leu Val
370                 375                 380

Val Asp Phe Ser Gln Phe Ser Arg Gly Ile Thr Arg Val Ser Trp Pro
385                 390                 395                 400

Lys Phe Ala Val Pro Asn Leu Gln Ser Leu Thr Asn Leu Leu Ser Ser
            405                 410                 415

Asn Leu Ser Trp Leu Ser Leu Asp Val Ser Ala Ala Phe Tyr His Ile
            420                 425                 430

Pro Leu His Pro Ala Ala Met Pro His Leu Leu Ile Gly Ser Ser Gly
            435                 440                 445

Leu Ser Arg Tyr Val Ala Arg Leu Ser Ser Asn Ser Arg Ile Asn Asn
    450                 455                 460

Asn Gln Tyr Gly Thr Met Gln Asn Leu His Asp Ser Cys Ser Arg Gln
465                 470                 475                 480

Leu (2) INFORMATION FOR SEQ ID NO: 53:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 53:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn His Arg Val Ala Glu Asp Leu Asn Leu Gly Asn Pro Asn Val
            35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

Asp Ile His Leu Gln Glu Asp Ile Val Asp Arg Cys Lys Gln Phe Val
            85                  90                  95

Gly Pro Leu Thr Val Asn Glu Asn Arg Arg Leu Lys Leu Ile Met Pro
```

-continued

```
                100                 105                 110
Ala Arg Phe Tyr Pro Asn Val Thr Lys Tyr Leu Pro Leu Asp Lys Gly
            115                 120                 125
Ile Lys Pro Tyr Tyr Pro Glu His Val Val Asn His Tyr Phe Gln Thr
130                 135                 140
Arg His Tyr Leu His Thr Leu Trp Lys Ala Gly Ile Leu Tyr Lys Arg
145                 150                 155                 160
Glu Ser Thr Arg Ser Ala Ser Phe Cys Gly Ser Pro Tyr Ser Trp Glu
                165                 170                 175
Gln Asp Leu Gln His Gly Arg Leu Val Phe Gln Thr Ser Lys Arg His
            180                 185                 190
Gly Asp Lys Ser Phe Cys Pro Gln Ser Pro Gly Ile Leu Pro Arg Ser
            195                 200                 205
Ser Val Gly Pro Cys Ile Gln Ser Gln Leu Arg Lys Ser Arg Leu Gly
        210                 215                 220
Pro Gln Pro Thr Gln Gly Gln Leu Ala Gly Arg Pro Gln Gly Gly Ser
225                 230                 235                 240
Gly Ser Ile Arg Ala Arg Ile His Pro Ser Pro Trp Gly Thr Val Gly
                245                 250                 255
Val Glu Pro Ser Gly Ser Gly His Thr His Ile Cys Ala Ser Ser Ser
            260                 265                 270
Ser Ser Cys Leu His Gln Ser Ala Val Arg Thr Ala Ala Tyr Ser Pro
        275                 280                 285
Ile Ser Thr Ser Lys Gly His Ser Ser Gly His Ala Val Glu Leu
        290                 295                 300
His His Phe Pro Pro Asn Ser Ser Arg Ser Gln Ser Gln Gly Ser Val
305                 310                 315                 320
Leu Ser Cys Trp Trp Leu Gln Phe Arg Asn Ser Lys Pro Cys Ser Glu
                325                 330                 335
Tyr Cys Leu Ser His Ile Val Asn Leu Ile Glu Asp Trp Gly Pro Cys
                340                 345                 350
Ala Glu His Gly Glu His Arg Ile Arg Thr Pro Arg Thr Pro Ala Arg
            355                 360                 365
Val Thr Gly Gly Val Phe Leu Val Asp Lys Asn Pro His Asn Thr Thr
        370                 375                 380
Glu Ser Arg Leu Val Val Asp Phe Ser Gln Phe Ser Arg Gly Asn Thr
385                 390                 395                 400
Arg Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
                420                 425                 430
Ala Phe Tyr His Leu Pro Leu His Pro Ala Ala Met Pro His Leu Leu
            435                 440                 445
Val Gly Ser Ser Gly Leu Ser Arg Tyr Val Ala Arg Leu Ser Ser Asn
        450                 455                 460
Ser Arg Ile Ile Asn His Gln His Gly Thr Met Gln Asp Leu His Asp
465                 470                 475                 480
Ser Cys Ser Arg Asn Leu Tyr Val Ser Leu Met Leu Leu Tyr Lys Thr
                485                 490                 495
Tyr Gly Trp Lys Leu His Leu Tyr Ser His Pro Ile Ile Leu Gly Phe
                500                 505                 510
Arg Lys Ile Pro Met Gly Val Gly Leu Ser Pro Phe Leu Leu Ala Gln
            515                 520                 525
```

```
Phe Thr Ser Ala Ile Cys Ser Val Val Arg Arg Ala Phe Pro His Cys
    530                 535                 540
Leu Ala Phe Ser Tyr Met Asp Asp Val Val Leu Gly Ala Lys Ser Val
545                 550                 555                 560
Gln His Leu Glu Ser Leu Tyr Ala Ala Val Thr Asn Phe Leu Leu Ser
                565                 570                 575
Leu Gly Ile His Leu Asn Pro Asn Lys Thr Lys Arg Trp Gly Tyr Ser
                580                 585                 590
Leu Asn Phe Met Gly Tyr Val Ile Gly Ser Trp Gly Thr Trp Pro Gln
        595                 600                 605
Asp His Ile Val Gln Asn Phe Lys Leu Cys Phe Arg Lys Leu Pro Val
        610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ala Lys Gln Ala Phe Thr Phe Ser Pro Thr
                660                 665                 670
Tyr Lys Ala Phe Leu Ser Lys Gln Tyr Met Thr Leu Tyr Pro Val Ala
                675                 680                 685
Arg Gln Arg Pro Gly Leu Cys Gln Val Phe Ala Asp Ala Thr Pro Thr
690                 695                 700
Gly Trp Gly Leu Ala Ile Gly His Gln Arg Met Arg Gly Thr Phe Val
705                 710                 715                 720
Ser Pro Leu Pro Ile His Thr Ala Glu Leu Leu Ala Ala Cys Phe Ala
                725                 730                 735
Arg Ser Arg Ser Gly Ala Asn Leu Ile Gly Thr Asp Asn Ser Val Val
                740                 745                 750
Leu Ser Arg Lys Tyr Thr Ser Phe Pro Trp Leu Leu Gly Cys Ala Ala
                755                 760                 765
Asn Trp Ile Leu Arg Gly Thr Ser Phe Val Tyr Val Pro Ser Ala Leu
        770                 775                 780
Asn Pro Ala Asp Asp Pro Ser Arg Gly Arg Leu Gly Leu Tyr Arg Pro
785                 790                 795                 800
Leu Leu Arg Leu Pro Tyr Arg Pro Thr Thr Gly Arg Thr Ser Leu Tyr
                805                 810                 815
Ala Asp Ser Pro Ser Val Pro Ser His Leu Pro Asp Arg Val His Phe
                820                 825                 830
Ala Ser Pro Leu His Val Ala Trp Arg Pro Pro
                835                 840
```

(2) INFORMATION FOR SEQ ID NO: 54:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 54:

```
Met Pro Leu Ser Tyr Gln His Phe Arg Lys Leu Leu Leu Leu Asp Glu
1               5                   10                  15
Glu Ala Gly Pro Leu Glu Glu Glu Leu Pro Arg Leu Ala Asp Glu Gly
                20                  25                  30
```

-continued

```
Leu Asn Arg Arg Val Ala Glu Asp Leu Asn Leu Gly Asn Leu Asn Val
         35                  40                  45

Ser Ile Pro Trp Thr His Lys Val Gly Asn Phe Thr Gly Leu Tyr Ser
 50                  55                  60

Ser Thr Val Pro Cys Phe Asn Pro Lys Trp Gln Thr Pro Ser Phe Pro
 65                  70                  75                  80

Asp Ile His Leu Gln Glu Asp Ile Val Asp Arg Cys Lys Gln Phe Val
                     85                  90                  95

Gly Pro Leu Thr Val Asn Glu Asn Arg Arg Leu Lys Leu Ile Met Pro
                    100                 105                 110

Ala Arg Phe Tyr Pro Asn Val Thr Lys Tyr Leu Pro Leu Asp Lys Gly
             115                 120                 125

Ile Lys Pro Tyr Tyr Pro Glu His Val Val Asn His Tyr Phe Gln Thr
         130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                    165                 170                 175

Gln Asp Leu Gln His Gly Arg Leu Val Phe Gln Thr Ser Lys Arg His
             180                 185                 190

Gly Asp Lys Ser Phe Cys Pro Gln Ser Ser Gly Ile Leu Pro Arg Ser
         195                 200                 205

Ser Val Gly Pro Cys Ile Gln Ser Gln Leu Arg Lys Ser Arg Leu Gly
210                 215                 220

Pro Gln Pro Glu Gln Gly Gln Leu Ala Gly Arg Gln Gln Gly Gly Ser
225                 230                 235                 240

Gly Ser Ile Arg Ala Arg Val His Pro Ser Pro Trp Gly Thr Val Gly
                    245                 250                 255

Val Glu Pro Ser Gly Ser Gly Pro Thr His Asn Cys Ala Ser Ser Ser
             260                 265                 270

Ser Ser Cys Leu His Gln Ser Ala Val Arg Lys Ala Ala Tyr Ser Leu
         275                 280                 285

Ile Pro Thr Ser Lys Gly His Ser Ser Ser Gly His Ala Val Glu Leu
290                 295                 300

His His Phe Pro Pro Asn Ser Ser Arg Ser Arg Ser Gln Gly Pro Val
305                 310                 315                 320

Leu Ser Cys Trp Trp Leu Gln Phe Arg Asn Ser Glu Pro Cys Ser Glu
                    325                 330                 335

Tyr Cys Leu Cys His Ile Val Asn Leu Ile Glu Asp Trp Gly Pro Cys
             340                 345                 350

Thr Glu His Gly Glu His Arg Ile Arg Thr Pro Arg Thr Pro Ala Arg
         355                 360                 365

Val Thr Gly Gly Val Phe Leu Val Asp Lys Asn Pro His Asn Thr Thr
370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                    405                 410                 415

Asn Leu Leu Ser Ser Asn Leu Ser Trp Leu Ser Leu Asp Val Ser Ala
             420                 425                 430

Ala Phe Tyr His Leu Pro Leu His Pro Ala Ala Met Pro His Leu Leu
         435                 440                 445
```

```
Val Gly Ser Ser Gly Leu Ser Arg Tyr Val Ala Arg Leu Ser Ser Asn
    450                 455                 460

Ser Arg Ile Ile Asn Asn Gln His Arg Thr Met Gln Asn Leu His Asp
465                 470                 475                 480

Ser Cys Ser Arg Asn Leu Tyr Val Ser Leu Met Leu Leu Tyr Lys Thr
                485                 490                 495

Tyr Gly Trp Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Met Val Leu Gly Ala Lys Ser Val
545                 550                 555                 560

Gln His Leu Glu Ser Leu Tyr Ala Ala Val Thr Asn Phe Leu Leu Ser
                565                 570                 575

Leu Gly Ile His Leu Asn Pro His Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Met Trp Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
            660                 665                 670

Tyr Lys Ala Phe Leu Thr Lys Gln Tyr Leu Asn Leu Tyr Pro Val Ala
        675                 680                 685

Arg Gln Arg Pro Gly Leu Cys Gln Val Phe Ala Asp Ala Thr Pro Thr
    690                 695                 700

Gly Trp Gly Leu Ala Ile Gly His Gln Arg Met Arg Gly Thr Phe Val
705                 710                 715                 720

Ser Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Arg Leu Leu Tyr Arg Pro Thr Thr Gly Arg Thr Ser Leu Tyr
                805                 810                 815

Ala Asp Ser Pro Ser Val Pro Ser His Leu Pro Asp Arg Val His Phe
            820                 825                 830

Ala Ser Pro Leu His Val Ala Trp Arg Pro Pro
        835                 840
```

(2) INFORMATION FOR SEQ ID NO: 55:

(i) SEQUENCE CHARACTERISTICS:

(A) LENGTH: 843 amino acids
(B) TYPE: amino acid
(C) STRANDEDNESS: <Unknown>
(D) TOPOLOGY: linear (ii) MOLECULE TYPE: protein (xi) SEQUENCE DESCRIPTION: SEQ ID NO: 55:

```
Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Ser Phe Asn Pro Gln Trp Gln Thr Pro Ser Phe Pro
65                  70                  75                  80

Asp Ile His Leu Gln Glu Asp Ile Ile Asn Lys Cys Lys Gln Phe Val
                85                  90                  95

Gly Pro Leu Thr Val Asn Glu Lys Arg Leu Lys Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Val Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Leu Gln Thr Ser Thr Arg His
            180                 185                 190

Gly Asp Lys Ser Phe Arg Pro Gln Ser Ser Gly Ile Leu Ser Arg Ser
            195                 200                 205

Pro Val Gly Pro Cys Ile Gln Ser Gln Leu Arg Gln Ser Arg Leu Gly
210                 215                 220

Pro Gln Pro Thr Gln Gly Gln Leu Ala Gly Leu Gln Gly Gly Ser
225                 230                 235                 240

Gly Ser Ile Arg Ala Gly Ile His Ser Thr Pro Trp Gly Thr Val Gly
                245                 250                 255

Val Glu Pro Ser Ser Ser Gly His Thr His Asn Cys Ala Asn Ser Ser
            260                 265                 270

Ser Ser Cys Leu His Gln Ser Ala Val Arg Lys Glu Ala Tyr Ser Pro
            275                 280                 285

Val Ser Thr Ser Lys Arg His Ser Ser Ser Gly Asn Ala Val Glu Leu
            290                 295                 300

His His Val Pro Pro Asn Ser Ser Arg Ser Gln Ser Gln Gly Ser Val
305                 310                 315                 320

Leu Ser Cys Trp Trp Leu Gln Phe Arg Asn Ser Lys Pro Cys Ser Glu
                325                 330                 335

His Cys Leu Phe His Ile Val Asn Leu Ile Asp Asp Trp Gly Pro Cys
            340                 345                 350

Ala Glu His Gly Glu His Arg Ile Arg Thr Pro Arg Thr Pro Ala Arg
            355                 360                 365

Val Thr Gly Gly Val Phe Leu Val Asp Lys Asn Pro His Asn Thr Ser
```

-continued

```
            370                 375                 380
Glu Ser Arg Leu Val Val Asp Phe Ser Gln Phe Ser Arg Gly Asn Thr
385                 390                 395                 400
Arg Val Ser Trp Pro Lys Phe Ala Val Pro Asn Leu Gln Ser Leu Thr
                    405                 410                 415
Asn Leu Leu Ser Ser Asp Leu Ser Trp Leu Ser Leu Asp Val Ser Ala
                420                 425                 430
Ala Phe Tyr His Leu Pro Leu His Pro Ala Ala Met Pro His Leu Leu
            435                 440                 445
Val Gly Ser Ser Gly Leu Ser Arg Tyr Val Ala Arg Leu Ser Ser Asn
        450                 455                 460
Ser Arg Ile Ile Asn His Gln His Arg Thr Met Gln Asn Leu His Asp
465                 470                 475                 480
Ser Cys Ser Arg Asn Leu Tyr Val Ser Leu Met Leu Leu Tyr Lys Thr
                    485                 490                 495
Tyr Gly Arg Lys Leu His Leu Tyr Ser His Pro Ile Ile Leu Gly Phe
                500                 505                 510
Arg Lys Ile Pro Met Gly Val Gly Leu Ser Pro Phe Leu Leu Ala Gln
            515                 520                 525
Phe Thr Ser Ala Ile Cys Ser Val Val Arg Arg Ala Phe Pro His Cys
        530                 535                 540
Leu Ala Phe Ser Tyr Met Asp Asp Val Val Leu Gly Ala Lys Ser Val
545                 550                 555                 560
Gln His Leu Glu Ser Leu Tyr Ala Ala Val Thr Asn Phe Leu Leu Ser
                    565                 570                 575
Leu Gly Ile His Leu Asn Pro Gln Lys Thr Lys Arg Trp Gly Tyr Ser
                580                 585                 590
Leu Asn Phe Met Gly Tyr Val Ile Gly Ser Trp Gly Thr Leu Pro Gln
            595                 600                 605
Glu His Ile Val Leu Lys Ile Lys Gln Cys Phe Arg Lys Leu Pro Val
        610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                    645                 650                 655
Leu Tyr Ala Cys Ile Gln Ala Lys Gln Ala Phe Thr Phe Ser Pro Thr
                660                 665                 670
Tyr Lys Ala Phe Leu Asn Lys Gln Tyr Leu Asn Leu Tyr Pro Val Ala
            675                 680                 685
Arg Gln Arg Pro Gly Leu Cys Gln Val Phe Ala Asp Ala Thr Pro Thr
        690                 695                 700
Gly Trp Gly Leu Ala Ile Gly His Gln Arg Met Arg Gly Thr Phe Val
705                 710                 715                 720
Ser Pro Leu Pro Ile His Thr Val Glu Leu Leu Ala Ala Cys Phe Ala
                    725                 730                 735
Arg Ser Arg Ser Gly Ala Lys Leu Ile Gly Thr Asp Asn Ser Val Val
                740                 745                 750
Leu Ser Arg Lys Tyr Thr Ser Phe Pro Trp Leu Leu Gly Cys Ala Ala
            755                 760                 765
Asn Trp Ile Leu Arg Gly Thr Ser Phe Val Tyr Val Pro Ser Ala Leu
        770                 775                 780
Asn Pro Ala Asp Asp Pro Ser Arg Gly Arg Leu Gly Leu Tyr Arg Pro
785                 790                 795                 800
```

```
Leu Leu Arg Leu Pro Tyr Arg Pro Thr Thr Gly Arg Thr Ser Leu Tyr
            805                 810                 815

Ala Asp Ser Pro Ser Val Pro Ser His Leu Pro Asp Arg Val His Phe
            820                 825                 830

Ala Ser Pro Leu His Val Ala Trp Arg Pro Pro
            835                 840
```

(2) INFORMATION FOR SEQ ID NO: 56:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 56:

```
Met Pro Leu Ser Tyr Gln His Phe Arg Lys Leu Leu Leu Leu Asp Asp
1               5                   10                  15

Glu Ala Gly Pro Leu Glu Glu Leu Pro His Leu Ala Asp Glu Gly
            20                  25                  30

Leu Asn Arg Pro Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Ser Phe Asn Pro Lys Trp Gln Thr Pro Ser Phe Pro
65                  70                  75                  80

Asp Ile His Leu Gln Glu Asp Ile Ile Asn Arg Cys Glu Gln Phe Val
            85                  90                  95

Gly Pro Leu Thr Val Asn Glu Asn Arg Arg Leu Lys Leu Ile Met Pro
            100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Val Val Asn His Tyr Phe Gln Thr
            130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
            165                 170                 175

Gln Asp Leu Gln His Gly Arg Leu Val Leu Gln Thr Ser Thr Arg His
            180                 185                 190

Gly Asp Lys Ser Phe Arg Pro Gln Ser Ser Gly Ile Leu Ser Arg Ser
            195                 200                 205

Pro Val Gly Pro Cys Ile Gln Ser Gln Leu Arg Gln Ser Arg Leu Gly
            210                 215                 220

Pro Gln Pro Thr Gln Gly Gln Leu Ala Gly Leu Gln Gln Gly Gly Ser
225                 230                 235                 240

Gly Ser Ile Arg Ala Gly Ile His Ser Thr Pro Trp Gly Thr Val Gly
            245                 250                 255

Val Glu Pro Ser Ser Ser Gly His Thr His Asn Cys Ala Asn Ser Ser
            260                 265                 270

Ser Ser Cys Leu His Gln Ser Ala Val Arg Lys Glu Ala Tyr Ser Pro
            275                 280                 285

Val Ser Thr Ser Lys Arg His Ser Ser Ser Gly His Ala Val Glu Leu
            290                 295                 300
```

-continued

```
His His Val Pro Pro Asn Ser Ser Arg Ser Gln Ser Gln Gly Ser Val
305                 310                 315                 320

Leu Ser Cys Trp Trp Leu Gln Phe Arg Asn Ser Lys Pro Cys Ser Glu
            325                 330                 335

His Cys Leu Phe His Ile Val Asn Leu Ile Glu Asp Trp Gly Pro Cys
            340                 345                 350

Ala Glu His Gly Glu His Arg Ile Arg Thr Pro Arg Thr Pro Ala Arg
            355                 360                 365

Val Thr Gly Gly Val Phe Leu Val Asp Lys Asn Pro His Asn Thr Thr
            370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
            405                 410                 415

Asn Leu Leu Ser Ser Asp Leu Ser Trp Leu Ser Leu Asp Val Ser Ala
            420                 425                 430

Ala Phe Tyr His Leu Pro Leu His Pro Ala Ala Met Pro His Leu Leu
            435                 440                 445

Val Gly Ser Ser Gly Leu Ser Arg Tyr Val Ala Arg Leu Ser Ser Asn
450                 455                 460

Ser Arg Ile Ile Asn His Gln His Arg Thr Met Gln Asn Leu His Asp
465                 470                 475                 480

Ser Cys Ser Arg Asn Leu Tyr Val Ser Leu Met Leu Leu Tyr Lys Thr
            485                 490                 495

Tyr Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
            530                 535                 540

Leu Ala Phe Ser Tyr Met Asp Asp Val Val Leu Gly Ala Lys Ser Val
545                 550                 555                 560

Gln His Leu Glu Ser Leu Tyr Ala Ala Val Thr Asn Phe Leu Leu Ser
            565                 570                 575

Leu Gly Ile His Leu Asn Pro Gln Lys Thr Lys Arg Trp Gly Tyr Ser
            580                 585                 590

Leu Asn Phe Met Gly Tyr Val Ile Gly Ser Trp Gly Thr Leu Pro Gln
            595                 600                 605

Glu His Ile Val Leu Lys Leu Lys Gln Cys Phe Arg Lys Leu Pro Val
            610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
            645                 650                 655

Leu Tyr Ala Cys Ile Gln Ala Lys Gln Ala Phe Thr Phe Ser Pro Thr
            660                 665                 670

Tyr Lys Ala Phe Leu Thr Lys Gln Tyr Leu Asn Leu Tyr Pro Val Ala
            675                 680                 685

Arg Gln Arg Pro Gly Leu Cys Gln Val Phe Ala Asp Ala Thr Pro Thr
            690                 695                 700

Gly Trp Gly Leu Ala Ile Gly His Gln Arg Met Arg Gly Thr Phe Val
705                 710                 715                 720
```

```
Ser Pro Leu Pro Ile His Thr Ala Glu Leu Leu Ala Ala Cys Phe Ala
            725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
            755                 760                 765

Asn Trp Ile Leu Arg Gly Thr Ser Phe Val Tyr Val Pro Ser Ala Leu
            770                 775                 780

Asn Pro Ala Asp Asp Pro Ser Arg Gly Arg Leu Gly Leu Tyr Arg Pro
785                 790                 795                 800

Leu Leu Arg Leu Pro Tyr Arg Pro Thr Thr Gly Arg Thr Ser Leu Tyr
            805                 810                 815

Ala Asp Ser Pro Ser Val Pro Ser Arg Leu Pro Asp Arg Val His Phe
            820                 825                 830

Ala Ser Pro Leu His Val Ala Trp Arg Pro Pro
            835                 840
```

(2) INFORMATION FOR SEQ ID NO: 57:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 57:

```
Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
                20                  25                  30

Ala Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                  55                  60

Tyr Ser Ser Thr Ala Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
            100                 105                 110

Met Pro Ala Arg Phe Tyr Pro Thr His Thr Lys Tyr Leu Pro Leu Asp
            115                 120                 125

Lys Gly Ile Lys Pro Tyr Tyr Pro Asp Gln Val Val Asn His Tyr Phe
130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
            180                 185                 190

Arg His Gly Asp Glu Ser Phe Cys Ser Gln Pro Ser Gly Ile Leu Ser
            195                 200                 205

Arg Ser Ser Val Gly Pro Cys Ile Arg Ser Gln Leu Lys Gln Ser Arg
            210                 215                 220
```

-continued

```
Leu Gly Leu Gln Pro His Gln Gly Pro Leu Ala Ser Ser Gln Pro Gly
225                 230                 235                 240

Arg Ser Gly Ser Ile Arg Ala Arg Val His Pro Ser Thr Arg Arg Cys
                245                 250                 255

Phe Gly Val Glu Pro Ser Gly Ser Gly His Val Asp Pro Ser Val Asn
            260                 265                 270

Asn Ser Ser Ser Cys Leu Arg Gln Ser Ala Val Arg Lys Ala Ala Tyr
            275                 280                 285

Ser His Leu Ser Thr Ser Lys Arg Gln Ser Ser Gly His Ala Val
        290                 295                 300

Glu Phe His Cys Leu Pro Pro Ser Ser Ala Arg Pro Gln Ser Gln Gly
305                 310                 315                 320

Ser Val Phe Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Arg Gly
            340                 345                 350

Pro Cys Asp Glu His Gly Glu His His Ile Arg Ile Pro Arg Thr Pro
        355                 360                 365

Ala Arg Val Thr Gly Gly Val Phe Leu Val Asp Lys Asn Pro His Asn
370                 375                 380

Thr Ala Glu Ser Arg Leu Val Val Asp Phe Ser Gln Phe Ser Arg Gly
385                 390                 395                 400

Ile Thr Arg Val Ser Trp Pro Lys Phe Ala Ile Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
        435                 440                 445

Leu Leu Ile Gly Ser Ser Gly Leu Ser Arg Tyr Val Ala Arg Leu Ser
    450                 455                 460

Ser Asn Ser Arg Ile Asn Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
            500                 505                 510

Gly Phe Arg Lys Ile Pro Met Gly Val Gly Leu Ser Pro Phe Leu Leu
        515                 520                 525

Ala Gln Phe Thr Ser Ala Ile Cys Ser Val Val Arg Arg Ala Phe Pro
530                 535                 540

His Cys Leu Ala Phe Ser Tyr Met Asp Asp Val Val Leu Gly Ala Lys
545                 550                 555                 560

Ser Val Gln His Arg Glu Phe Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Ser Trp Gly Thr Leu
        595                 600                 605

Pro Gln Asp His Ile Val Gln Lys Ile Lys His Cys Phe Arg Lys Leu
    610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
```

```
                      645                 650                 655
Met Pro Leu Tyr Ala Cys Ile Gln Ala Lys Gln Ala Phe Thr Phe Ser
                660                 665                 670

Pro Thr Tyr Lys Ala Phe Leu Ser Lys Gln Tyr Met Asn Leu Tyr Pro
                675                 680                 685

Val Ala Arg Gln Arg Pro Gly Leu Cys Gln Val Phe Ala Asp Ala Thr
                690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
                740                 745                 750

Val Val Leu Ser Arg Lys Tyr Thr Ser Phe Pro Trp Leu Leu Gly Cys
                755                 760                 765

Ala Ala Asn Trp Ile Leu Arg Gly Thr Ser Phe Val Tyr Val Pro Ser
                770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
                805                 810                 815

Leu Tyr Ala Val Ser Pro Ser Val Pro Ser His Leu Pro Val Arg Val
                820                 825                 830

His Phe Ala Ser Pro Leu His Val Ala Trp Arg Pro Pro
                835                 840                 845

(2) INFORMATION FOR SEQ ID NO: 58:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 58:

Met Pro Leu Ser Tyr Gln His Phe Arg Lys Leu Leu Leu Leu Asp Asp
1                   5                  10                  15

Gly Thr Glu Ala Gly Pro Leu Glu Glu Glu Leu Pro Arg Leu Ala Asp
                20                  25                  30

Ala Asp Leu His Arg Arg Val Ala Glu Asp Leu Asn Leu Gly Asn Leu
                35                  40                  45

Asn Val Ser Ile Pro Trp Thr His Lys Val Gly Asn Phe Thr Gly Leu
            50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Thr His Thr Lys Tyr Leu Pro Leu Asp
                115                 120                 125

Lys Gly Ile Lys Pro Tyr Tyr Pro Asp Gln Val Val Asn His Tyr Phe
                130                 135                 140

Gln Thr Arg His Tyr Leu His Thr Leu Trp Lys Ala Gly Ile Leu Tyr
```

```
                                 -continued
145                 150                 155                 160
Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
                180                 185                 190

Arg His Gly Asp Glu Ser Phe Cys Ser Gln Ser Ser Gly Ile Leu Ser
                195                 200                 205

Arg Ser Ser Val Gly Pro Cys Ile Arg Ser Gln Leu Lys Gln Ser Arg
                210                 215                 220

Leu Gly Leu Gln Pro Arg Gln Gly Arg Leu Ala Ser Ser Gln Pro Ser
225                 230                 235                 240

Arg Ser Gly Ser Ile Arg Ala Lys Ala His Pro Ser Thr Arg Arg Tyr
                245                 250                 255

Phe Gly Val Glu Pro Ser Gly Ser Gly His Ile Asp His Ser Val Asn
                260                 265                 270

Asn Ser Ser Ser Cys Leu His Gln Ser Ala Val Arg Lys Ala Ala Tyr
                275                 280                 285

Ser His Leu Ser Thr Ser Lys Arg Gln Ser Ser Gly His Ala Val
        290                 295                 300

Glu Phe His Cys Leu Pro Pro Asn Ser Ala Gly Ser Gln Ser Gln Gly
305                 310                 315                 320

Ser Val Ser Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Trp Gly
                340                 345                 350

Pro Cys Asp Glu His Gly Glu His His Ile Arg Ile Pro Arg Thr Pro
                355                 360                 365

Ala Arg Val Thr Gly Gly Val Phe Leu Val Asp Lys Asn Pro His Asn
                370                 375                 380

Thr Ala Glu Ser Arg Leu Val Val Asp Phe Ser Gln Phe Ser Arg Gly
385                 390                 395                 400

Ile Ser Arg Val Ser Trp Pro Lys Phe Ala Val Pro Asn Leu Gln Ser
                405                 410                 415

Leu Thr Asn Leu Leu Ser Ser Asn Leu Ser Trp Leu Ser Leu Asp Val
                420                 425                 430

Ser Ala Ala Phe Tyr His Ile Pro Leu His Pro Ala Ala Met Pro His
                435                 440                 445

Leu Leu Ile Gly Ser Ser Gly Leu Ser Arg Tyr Val Ala Arg Leu Ser
450                 455                 460

Ser Asn Ser Arg Ile Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
                500                 505                 510

Gly Phe Arg Lys Ile Pro Met Gly Val Gly Leu Ser Pro Phe Leu Leu
                515                 520                 525

Ala Gln Phe Thr Ser Ala Ile Cys Ser Val Val Arg Arg Ala Phe Pro
                530                 535                 540

His Cys Leu Ala Phe Ser Tyr Met Asp Asp Val Val Leu Gly Ala Lys
545                 550                 555                 560

Ser Val Gln His Arg Glu Ser Leu Tyr Thr Ala Val Thr Asn Phe Leu
                565                 570                 575
```

-continued

```
Leu Ser Leu Gly Ile His Leu Asn Pro Asn Lys Thr Lys Arg Trp Gly
                580                 585                 590

Tyr Ser Leu Asn Phe Met Gly Tyr Ile Ile Gly Ser Trp Gly Thr Leu
            595                 600                 605

Pro Gln Asp His Ile Val Gln Lys Ile Lys His Cys Phe Arg Lys Leu
        610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
        675                 680                 685

Val Ala Arg Gln Arg Pro Gly Leu Cys Gln Val Phe Ala Asp Ala Thr
        690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
                740                 745                 750

Val Val Leu Ser Arg Lys Tyr Thr Ser Phe Pro Trp Leu Leu Gly Cys
            755                 760                 765

Thr Ala Asn Trp Ile Leu Arg Gly Thr Ser Phe Val Tyr Val Pro Ser
770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
                805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
            835                 840                 845

(2) INFORMATION FOR SEQ ID NO: 59:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 59:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro Asp Trp Lys Thr Pro Ser Phe Pro
65                  70                  75                  80
```

```
His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu Tyr Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Trp Ser Arg Val His Pro Thr Thr Arg Pro Phe Gly
                245                 250                 255

Val Glu Pro Ser Gly Ser Gly His Ile Asp Asn Thr Ala Ser Ser Thr
                260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Ser Gly His Ala Val Glu Leu
    290                 295                 300

His Asn Ile Pro Pro Ser Ser Ala Arg Ser Gln Ser Glu Gly Pro Ile
305                 310                 315                 320

Phe Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
        435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asn Leu His Asp
465                 470                 475                 480

Ser Cys Ser Arg Asn Leu Tyr Val Ser Leu Leu Leu Leu Tyr Lys Thr
                485                 490                 495
```

```
Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Leu Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Lys Gln Tyr Leu Asn Leu Tyr Pro Val Ala
        675                 680                 685

Arg Gln Arg Ser Gly Leu Cys Gln Val Phe Ala Asp Ala Thr Pro Thr
    690                 695                 700

Gly Trp Gly Leu Ala Ile Gly His Arg Arg Met Arg Gly Thr Phe Val
705                 710                 715                 720

Ala Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu His Leu Pro Phe Arg Pro Thr Thr Gly Arg Thr Ser Leu Tyr
                805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
        835                 840
```

(2) INFORMATION FOR SEQ ID NO: 60:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 60:

-continued

```
Met Pro Leu Ser Tyr Gln His Phe Arg Leu Leu Leu Asp Asp
1               5                   10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                      55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Lys Val Thr Lys Tyr Leu Pro Leu Asp Lys Gly
            115                 120                 125

Ile Lys Pro Tyr Tyr Pro Glu His Leu Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Ser Ser Gly
                180                 185                 190

Ile Leu Ser Arg Pro Pro Val Gly Ser Ser Leu Gln Ser Lys His Arg
            195                 200                 205

Lys Ser Arg Leu Gly Leu Gln Ser Gln Gln Gly His Leu Ala Arg Arg
        210                 215                 220

Gln Gln Gly Arg Ser Trp Ser Ile Arg Ala Gly Phe His Pro Thr Ala
225                 230                 235                 240

Arg Arg Pro Phe Gly Val Glu Pro Ser Gly Ser Gly His Thr Thr Asn
                245                 250                 255

Phe Ala Ser Lys Ser Ala Ser Cys Leu His Gln Ser Pro Val Arg Lys
                260                 265                 270

Ala Ala Tyr Pro Ala Val Ser Thr Phe Glu Lys His Ser Ser Ser Gly
            275                 280                 285

His Ala Val Glu Phe His Asn Leu Pro Pro Asn Ser Ala Arg Ser Gln
        290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ser Arg Val Thr Gly Gly Val Phe Leu Val Asp Lys Asn
        355                 360                 365

Pro His Asn Thr Ala Glu Ser Arg Leu Val Val Asp Phe Ser Gln Phe
370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
```

-continued

```
                420                 425                 430
Met Pro His Leu Leu Val Gly Ser Ser Gly Leu Ser Arg Tyr Val Ala
            435                 440                 445
Arg Leu Ser Ser Asn Ser Arg Ile Leu Asn Asn Gln His Gly Thr Met
450                 455                 460
Pro Asp Leu His Asp Tyr Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                485                 490                 495
Ile Ile Leu Gly Phe Arg Lys Ile Pro Met Gly Val Gly Leu Ser Pro
                500                 505                 510
Phe Leu Leu Ala Gln Phe Thr Ser Ala Ile Cys Ser Val Val Arg Arg
            515                 520                 525
Ala Phe Pro His Cys Leu Ala Phe Ser Tyr Met Asp Asp Val Val Leu
530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu Asn Phe Met Gly Tyr Val Ile Gly Cys Tyr
            580                 585                 590
Gly Ser Leu Pro Gln Glu His Ile Ile Gln Lys Ile Lys Glu Cys Phe
            595                 600                 605
Arg Lys Leu Pro Ile Asn Arg Pro Ile Asp Trp Lys Val Cys Gln Arg
            610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ser Lys Gln Ala Phe
                645                 650                 655
Thr Phe Ser Pro Thr Tyr Lys Ala Phe Leu Cys Lys Gln Tyr Leu Asn
                660                 665                 670
Leu Tyr Pro Val Ala Arg Gln Arg Pro Gly Leu Cys Gln Val Phe Ala
            675                 680                 685
Asp Ala Thr Pro Thr Gly Trp Gly Leu Val Met Gly His Gln Arg Met
690                 695                 700
Arg Gly Thr Phe Ser Ala Pro Leu Pro Ile His Thr Ala Glu Leu Leu
705                 710                 715                 720
Ala Ala Cys Phe Ala Arg Ser Arg Ser Gly Ala Asn Ile Ile Gly Thr
                725                 730                 735
Asp Asn Ser Val Val Leu Ser Arg Lys Tyr Thr Ser Phe Pro Trp Leu
            740                 745                 750
Leu Gly Cys Ala Ala Asn Trp Ile Leu Arg Gly Thr Ser Phe Val Tyr
            755                 760                 765
Val Pro Ser Ala Leu Asn Pro Ala Asp Asp Pro Ser Arg Gly Arg Leu
770                 775                 780
Gly Leu Ser Arg Pro Leu Leu Arg Leu Pro Phe Arg Pro Thr Thr Gly
785                 790                 795                 800
Arg Thr Ser Leu Tyr Ala Asp Ser Pro Ser Val Pro Ser His Leu Pro
                805                 810                 815
Asp Arg Val His Phe Ala Ser Pro Leu His Val Ala Trp Arg Pro Pro
            820                 825                 830
```

(2) INFORMATION FOR SEQ ID NO: 61:

(i) SEQUENCE CHARACTERISTICS:
    (A) LENGTH: 832 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 61:

```
Met Pro Leu Ser Tyr Gln His Phe Arg Arg Leu Leu Leu Asp Asp
1               5                  10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
            85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu Tyr Leu Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gly His Leu Ala Arg Arg
    210                 215                 220

Gln Gln Gly Arg Ser Trp Ser Ile Arg Ala Gly Ile His Pro Thr Thr
225                 230                 235                 240

Arg Arg Pro Phe Gly Val Glu Pro Ser Gly Ser Gly His Thr Arg Asn
                245                 250                 255

Val Ala Ser Lys Ser Ala Ser Cys Leu Tyr Gln Ser Pro Val Arg Lys
            260                 265                 270

Ala Ala Tyr Pro Ala Val Ser Thr Phe Glu Lys His Ser Ser Ser Gly
        275                 280                 285

His Ala Val Glu Leu His Asn Leu Pro Pro Asn Ser Ala Arg Ser Gln
290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
            325                 330                 335

Asp Trp Gly Pro Cys Ala Glu His Gly Glu His His Ile Arg Ile Pro
        340                 345                 350

Arg Thr Pro Ala Arg Val Thr Gly Gly Val Phe Leu Val Asp Lys Asn
    355                 360                 365
```

-continued

```
Pro His Asn Thr Ala Glu Ser Arg Leu Val Val Asp Phe Ser Gln Phe
    370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Val Ser Ala Ala Phe Tyr His Leu Pro Leu His Pro Ala Ala
                420                 425                 430
Met Pro His Leu Leu Val Gly Ser Ser Gly Leu Ser Arg Tyr Val Ala
            435                 440                 445
Arg Leu Ser Ser Asn Ser Arg Ile Phe Asn Tyr Gln His Gly Thr Met
    450                 455                 460
Gln Asn Leu His Asp Ser Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                485                 490                 495
Ile Ile Leu Gly Phe Arg Lys Ile Pro Met Gly Val Gly Leu Ser Pro
                500                 505                 510
Phe Leu Leu Ala Gln Phe Thr Ser Ala Ile Cys Ser Val Val Arg Arg
            515                 520                 525
Ala Phe Pro His Cys Leu Ala Phe Ser Tyr Met Asp Asp Val Val Leu
    530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu His Phe Met Gly Tyr Val Ile Gly Cys Tyr
                580                 585                 590
Gly Ser Leu Pro Gln Asp His Ile Ile Gln Lys Ile Lys Glu Cys Phe
            595                 600                 605
Arg Lys Leu Pro Val Asn Arg Pro Ile Asp Trp Lys Val Cys Gln Arg
    610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ser Lys Gln Ala Phe
                645                 650                 655
Thr Phe Ser Pro Thr Tyr Lys Ala Phe Leu Cys Lys Gln Tyr Leu Asp
                660                 665                 670
Leu Tyr Pro Val Ala Arg Gln Arg Pro Gly Leu Cys Gln Val Phe Ala
            675                 680                 685
Asp Ala Thr Pro Thr Gly Trp Gly Leu Val Met Gly His Gln Arg Met
    690                 695                 700
Arg Gly Thr Phe Leu Ala Arg Leu Pro Ile His Thr Ala Glu Leu Leu
705                 710                 715                 720
Ala Ala Cys Phe Ala Arg Ser Arg Ser Gly Ala Asn Ile Leu Gly Thr
                725                 730                 735
Asp Asn Ser Val Val Leu Ser Arg Lys Tyr Thr Ser Tyr Pro Trp Leu
                740                 745                 750
Leu Gly Cys Ala Ala Asn Trp Ile Leu Arg Gly Thr Ser Phe Val Tyr
            755                 760                 765
Val Pro Ser Ala Leu Asn Pro Ala Asp Asp Pro Ser Arg Gly Arg Leu
    770                 775                 780
```

```
Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
                820                 825                 830
```

(2) INFORMATION FOR SEQ ID NO: 62:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 62:

```
Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
                35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Lys Val Thr Lys Tyr Leu Pro Leu Asp Lys Gly
                115                 120                 125

Ile Lys Pro Tyr Tyr Pro Glu His Leu Val Asn His Tyr Phe Gln Thr
                130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Ser Ser Gly
                180                 185                 190

Ile Leu Ser Arg Pro Pro Val Gly Ser Ser Leu Gln Ser Lys His Arg
                195                 200                 205

Lys Ser Arg Leu Gly Leu Gln Ser Gln Gln Gly His Leu Ala Arg Arg
210                 215                 220

Gln Gln Gly Arg Ser Trp Ser Ile Arg Ala Gly Phe His Pro Thr Ala
225                 230                 235                 240

Arg Arg Pro Phe Gly Val Glu Pro Ser Gly Ser Gly His Thr Thr Asn
                245                 250                 255

Phe Ala Ser Lys Ser Ala Ser Cys Leu His Gln Ser Pro Val Arg Lys
                260                 265                 270

Ala Ala Tyr Pro Ser Val Ser Thr Phe Glu Lys His Ser Ser Ser Gly
                275                 280                 285

His Ala Val Glu Leu His Asn Leu Pro Pro Asn Ser Ala Arg Ser Gln
                290                 295                 300
```

-continued

```
Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
            325                 330                 335

Asp Trp Gly Pro Cys Ala Glu His Gly His His Ile Arg Ile Pro
                340                 345                 350

Arg Thr Pro Ser Arg Val Thr Gly Gly Val Phe Leu Val Asp Lys Asn
        355                 360                 365

Pro His Asn Thr Ala Glu Ser Arg Leu Val Val Asp Phe Ser Gln Phe
    370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Leu Asn His Gln His Gly Thr Met
    450                 455                 460

Pro Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Tyr Met Asp Asp Val Val Leu
    530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu Asn Phe Met Gly Tyr Val Ile Gly Cys Tyr
            580                 585                 590

Gly Ser Leu Pro Gln Glu His Ile Ile Gln Lys Ile Lys Glu Cys Phe
        595                 600                 605

Arg Lys Leu Pro Val Asn Arg Pro Ile Asp Trp Lys Val Cys Gln Arg
    610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Gly Gln Arg Pro Gly Leu Cys Gln Val Phe Ala
        675                 680                 685

Asp Ala Thr Pro Thr Gly Trp Gly Leu Ala Met Gly His Gln Arg Met
    690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Ile Gly Thr
```

-continued

```
                725                 730                 735
Asp Asn Ser Val Val Leu Ser Arg Lys Tyr Thr Ser Phe Pro Trp Leu
            740                 745                 750
Leu Gly Cys Ala Ala Asn Trp Ile Leu Arg Gly Thr Ser Phe Val Tyr
            755                 760                 765
Val Pro Ser Ala Leu Asn Pro Ala Asp Asp Pro Ser Arg Gly Arg Leu
            770                 775                 780
Gly Leu Ser Arg Pro Leu Leu Arg Leu Pro Phe Arg Pro Thr Thr Gly
785                 790                 795                 800
Arg Thr Ser Leu Tyr Ala Asp Ser Pro Ser Val Pro Ser His Leu Pro
                805                 810                 815
Asp Leu Val His Phe Ala Ser Pro Leu His Val Ala Trp Arg Pro Pro
            820                 825                 830
```

(2) INFORMATION FOR SEQ ID NO: 63:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 63:

```
Met Pro Leu Ser Tyr Gln His Phe Arg Arg Leu Leu Leu Leu Asp Asp
1               5                   10                  15
Glu Ala Gly Pro Leu Glu Glu Leu Pro Arg Leu Ala Asp Glu Gly
            20                  25                  30
Leu Asn Arg Arg Val Ala Glu Asp Leu Asn Leu Gly Asn Leu Asn Val
            35                  40                  45
Ser Ile Pro Trp Thr His Lys Val Gly Asn Phe Thr Gly Phe Tyr Ser
        50                  55                  60
Ser Thr Val Pro Val Phe Asn Pro His Trp Glu Thr Pro Ser Phe Pro
65                  70                  75                  80
Asn Ile His Leu His Gln Asp Ile Ile Lys Lys Cys Glu Gln Phe Val
                85                  90                  95
Gly Pro Leu Thr Val Asn Glu Lys Arg Arg Leu Gln Leu Ile Met Pro
            100                 105                 110
Ala Arg Phe Tyr Pro Lys Val Thr Lys Tyr Leu Pro Leu Asp Lys Gly
            115                 120                 125
Ile Lys Pro Tyr Tyr Pro Glu His Leu Val Asn His Tyr Phe Gln Thr
            130                 135                 140
Arg His Tyr Leu His Thr Leu Trp Lys Ala Gly Ile Leu Tyr Lys Arg
145                 150                 155                 160
Glu Thr Thr His Ser Ala Ser Phe Cys Gly Ser Pro Tyr Ser Trp Glu
                165                 170                 175
Gln Asp Leu Gln His Gly Ala Glu Ser Ile His Gln Ser Ser Gly
            180                 185                 190
Ile Leu Ser Arg Pro Pro Val Gly Ser Ser Leu Gln Ser Lys His Arg
            195                 200                 205
Lys Ser Arg Leu Gly Leu Gln Ser Gln Gln Gly His Leu Ala Arg Arg
        210                 215                 220
Gln Gln Gly Trp Ser Trp Ser Ile Arg Ala Gly Thr His Pro Thr Ala
225                 230                 235                 240
Arg Arg Pro Phe Gly Val Glu Pro Ser Gly Ser Gly His Thr Thr His
```

```
                       245                 250                     255
Arg Ala Ser Lys Ser Ala Ser Cys Leu Tyr Gln Ser Pro Asp Arg Lys
                260             265                 270
Ala Thr Tyr Pro Ser Val Ser Thr Phe Glu Arg His Ser Ser Gly
            275                 280                 285
Arg Ala Val Glu Leu His Asn Phe Pro Pro Asn Ser Ala Arg Ser Gln
            290                 295                 300
Ser Glu Arg Pro Ile Phe Pro Cys Trp Trp Leu Gln Phe Arg Asn Ser
305                 310                 315                 320
Lys Pro Cys Ser Asp Tyr Cys Leu Ser Leu Ile Val Asn Leu Leu Glu
                325                 330                 335
Asp Trp Gly Pro Cys Asp Glu Tyr Gly Glu His His Ile Arg Ile Pro
                340                 345                 350
Arg Thr Pro Ala Arg Val Thr Gly Gly Val Phe Leu Val Asp Lys Asn
                355                 360                 365
Pro His Asn Thr Ala Glu Ser Arg Leu Val Val Asp Phe Ser Gln Phe
            370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Val Ser Ala Gly Phe Tyr His Leu Pro Leu His Pro Ala Ala
                420                 425                 430
Met Pro His Leu Leu Val Gly Ser Ser Gly Val Ser Arg Tyr Val Ala
                435                 440                 445
Arg Leu Ser Ser Asn Ser Arg Asn Asn Asn Gln Tyr Gly Thr Met
450                 455                 460
Gln Asn Leu His Asp Ser Cys Ser Arg Gln Leu Tyr Val Ser Leu Met
465                 470                 475                 480
Leu Leu Tyr Gln Asn Phe Gly Trp Lys Leu His Leu Tyr Ser His Pro
                485                 490                 495
Ile Val Leu Gly Phe Arg Lys Ile Pro Met Gly Val Gly Leu Ser Pro
                500                 505                 510
Phe Leu Leu Ala Gln Phe Thr Ser Ala Ile Cys Ser Val Val Arg Arg
                515                 520                 525
Ala Phe Pro His Cys Leu Ala Phe Ser Tyr Met Asp Asp Val Val Leu
                530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu His Phe Met Gly Tyr Val Ile Gly Cys Tyr
            580                 585                 590
Gly Ser Leu Pro Gln Glu His Ile Ile Gln Lys Ile Lys Glu Cys Phe
            595                 600                 605
Arg Lys Val Pro Val Asn Arg Pro Ile Asp Trp Lys Val Cys Gln Arg
            610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Phe Lys Gln Ala Phe
                645                 650                 655
Thr Phe Ser Pro Thr Tyr Lys Ala Phe Leu Cys Lys Gln Tyr Leu Asn
                660                 665                 670
```

```
Leu Tyr Pro Val Ala Arg Gln Arg Pro Gly Leu Cys Gln Val Phe Ala
            675                 680                 685

Asp Ala Thr Pro Thr Gly Trp Gly Leu Gly Met Gly His Gln Arg Met
        690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Leu Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
            755                 760                 765

Val Pro Ser Ala Leu Asn Pro Ala Asp Asp Pro Ser Arg Gly Arg Leu
            770                 775                 780

Gly Leu Ser Arg Pro Leu Leu Cys Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830

(2) INFORMATION FOR SEQ ID NO: 64:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 64:

Met Pro Leu Ser Tyr Gln His Phe Arg Arg Leu Leu Leu Leu His Asp
1               5                   10                  15

Glu Ala Gly Pro Leu Glu Glu Glu Leu Pro Arg Leu Pro Asp Gln Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Ala Glu Ser Phe His Gln Gln Ser Ser Gly
            180                 185                 190
```

-continued

```
Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
        210                 215                 220

Gln Gln Gly Arg Ser Trp Ser Ile Arg Ala Gly Phe His Pro Thr Ala
225                 230                 235                 240

Arg Arg Ser Phe Gly Val Glu Pro Ser Gly Ser Gly His Thr Thr Tyr
                245                 250                 255

Arg Ala Ser Lys Ser Ala Ser Cys Leu Tyr Gln Ser Pro Val Arg Lys
            260                 265                 270

Ala Ala Tyr Pro Ser Val Ser Thr Phe Glu Lys His Ser Ser Ser Gly
            275                 280                 285

His Ala Val Glu Leu His Asn Leu Pro Pro Asn Ser Ala Arg Ser Gln
        290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Arg Glu
                325                 330                 335

Asp Trp Gly Pro Cys Thr Glu His Gly Glu His His Ile Arg Ile Pro
                340                 345                 350

Arg Thr Pro Ala Arg Val Thr Gly Gly Val Phe Leu Val Asp Lys Asn
            355                 360                 365

Pro His Asn Thr Ala Glu Ser Arg Leu Val Val Asp Phe Ser Gln Phe
        370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Phe Asn Asn Gln His Gly Thr Met
    450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
                500                 505                 510

Phe Leu Leu Ala Gln Phe Thr Ser Ala Ile Cys Ser Val Val Arg Arg
            515                 520                 525

Ala Phe Pro His Cys Leu Ala Phe Ser Tyr Met Asp Asp Val Val Leu
        530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu Asn Phe Met Gly Tyr Ile Ile Gly Ser Trp
            580                 585                 590

Gly Thr Leu Pro Gln Asp His Ile Val Gln Lys Ile Lys Glu Cys Phe
        595                 600                 605
```

-continued

```
Arg Lys Leu Pro Val Asn Arg Pro Ile Asp Trp Lys Val Trp Gln Arg
        610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ala Lys Gln Ala Phe
                645                 650                 655
Thr Phe Ser Pro Thr Tyr Lys Ala Phe Leu Ser Lys Gln Tyr Met Asn
                660                 665                 670
Leu Tyr Pro Val Ala Arg Gln Arg Pro Gly Leu Cys Gln Val Phe Ala
                675                 680                 685
Asp Ala Thr Pro Thr Gly Trp Gly Leu Ala Ile Gly Asn Gln Arg Met
        690                 695                 700
Arg Gly Thr Ile Val Ala Pro Leu Pro Ile His Thr Ala Glu Leu Leu
705                 710                 715                 720
Ala Ala Cys Phe Ala Arg Ser Arg Ser Gly Ala Lys Leu Ile Gly Thr
                725                 730                 735
Asp Asn Ser Val Val Leu Ser Arg Lys Tyr Thr Ser Phe Pro Trp Leu
                740                 745                 750
Leu Gly Cys Thr Ala Asn Trp Ile Leu Arg Gly Thr Ser Phe Val Tyr
                755                 760                 765
Val Pro Ser Ala Leu Asn Pro Ala Asp Asp Pro Ser Arg Gly Arg Leu
770                 775                 780
Gly Leu Ser Arg Pro Leu Leu Arg Leu Pro Phe Gln Pro Thr Thr Gly
785                 790                 795                 800
Arg Thr Ser Leu Tyr Ala Val Ser Pro Ser Val Pro Ser His Leu Pro
                805                 810                 815
Val Arg Val His Phe Ala Ser Pro Leu His Ile Ala Trp Arg Pro Pro
                820                 825                 830

(2) INFORMATION FOR SEQ ID NO: 65:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 65:

Leu Ser Arg Tyr Val Ala Arg Leu
1               5

(2) INFORMATION FOR SEQ ID NO: 66:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 66:

Gly Leu Ser Arg Tyr Val Ala Arg
1               5

(2) INFORMATION FOR SEQ ID NO: 67:

(i) SEQUENCE CHARACTERISTICS:
        (A) LENGTH: 17 amino acids
```

(B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 67:

Ala Thr Val Glu Leu Leu Ser Phe Leu Pro Ser Asp Phe Phe Pro Ser
1               5                   10                  15

Val (2) INFORMATION FOR SEQ ID NO: 68:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 68:

Leu Pro Ser Asp Phe Phe Pro Ser Val
1               5

(2) INFORMATION FOR SEQ ID NO: 69:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 69:

Phe Leu Pro Ser Asp Phe Phe Pro Ser Val
1               5                   10

(2) INFORMATION FOR SEQ ID NO: 70:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 70:

Gly Arg Glu Thr Val Ile Glu Tyr Leu Val Ser Phe Gly Val Trp
1               5                   10                  15

(2) INFORMATION FOR SEQ ID NO: 71:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 71:

Leu Ser Thr Leu Pro Glu Thr Thr Val Val Arg Arg Arg Gly Arg
1               5                   10                  15

(2) INFORMATION FOR SEQ ID NO: 72:

```
    (i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 72:

Arg Asp Leu Leu Asp Thr Ala Ser Ala Leu Tyr Arg Glu Ala Leu Glu
1               5                   10                  15
Ser Pro Glu His
            20

(2) INFORMATION FOR SEQ ID NO: 73:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 73:

Glu Ile Arg Leu Lys Val Phe Val Leu
1               5

(2) INFORMATION FOR SEQ ID NO: 74:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 74:

Gly Leu Ser Pro Thr Val Trp Leu Ser Val
1               5                   10

(2) INFORMATION FOR SEQ ID NO: 75:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 75:

Ala Thr Val Glu Leu Leu Ser Phe Leu Pro Ser Asp Phe Phe Pro Ser
1               5                   10                  15
Val (2) INFORMATION FOR SEQ ID NO: 76:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 76:
```

Leu Ser Thr Leu Pro Glu Thr Thr Val Val Arg Arg Arg Gly Arg Ser
1               5                   10                  15

(2) INFORMATION FOR SEQ ID NO: 77:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 77:

Leu Ser Thr Leu Pro Glu Thr Thr Val Val Arg Arg Arg Gly
1               5                   10

(2) INFORMATION FOR SEQ ID NO: 78:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 78:

Leu Ser Thr Leu Pro Glu Thr Thr Val Val Arg Arg Arg
1               5                   10

(2) INFORMATION FOR SEQ ID NO: 79:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 79:

Leu Ser Thr Leu Pro Glu Thr Thr Val Val Arg Arg
1               5                   10

(2) INFORMATION FOR SEQ ID NO: 80:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 80:

Leu Ser Thr Leu Pro Glu Thr Thr Val Val Arg
1               5                   10

(2) INFORMATION FOR SEQ ID NO: 81:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 81:

Ser Thr Leu Pro Glu Thr Thr Val Val Arg Arg Gly Arg Ser
1               5                   10                  15

(2) INFORMATION FOR SEQ ID NO: 82:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 82:

Ser Thr Leu Pro Glu Thr Thr Val Val Arg Arg Arg Gly Arg
1               5                   10

(2) INFORMATION FOR SEQ ID NO: 83:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 83:

Ser Thr Leu Pro Glu Thr Thr Val Val Arg Arg Arg Gly
1               5                   10

(2) INFORMATION FOR SEQ ID NO: 84:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 84:

Ser Thr Leu Pro Glu Thr Thr Val Val Arg Arg Arg
1               5                   10

(2) INFORMATION FOR SEQ ID NO: 85:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 85:

Ser Thr Leu Pro Glu Thr Thr Val Val Arg Arg
1               5                   10

(2) INFORMATION FOR SEQ ID NO: 86:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 86:

Ser Thr Leu Pro Glu Thr Thr Val Val Arg
1               5                   10

(2) INFORMATION FOR SEQ ID NO: 87:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 87:

Ser Thr Leu Pro Glu Thr Thr Val Val
1               5

(2) INFORMATION FOR SEQ ID NO: 88:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 88:

Thr Leu Pro Glu Thr Thr Val Val Arg Arg Arg Gly Arg Ser
1               5                   10

(2) INFORMATION FOR SEQ ID NO: 89:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 89:

Thr Leu Pro Glu Thr Thr Val Val Arg Arg Arg Gly Arg
1               5                   10

(2) INFORMATION FOR SEQ ID NO: 90:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 90:

Thr Leu Pro Glu Thr Thr Val Val Arg Arg Arg Gly
1               5                   10

(2) INFORMATION FOR SEQ ID NO: 91:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 91:

Thr Leu Pro Glu Thr Thr Val Val Arg Arg Arg
1               5                   10

(2) INFORMATION FOR SEQ ID NO: 92:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 92:

Thr Leu Pro Glu Thr Thr Val Val Arg Arg
1               5                   10

(2) INFORMATION FOR SEQ ID NO: 93:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 93:

Thr Leu Pro Glu Thr Thr Val Val Arg
1               5

(2) INFORMATION FOR SEQ ID NO: 94:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 94:

Leu Pro Glu Thr Thr Val Val Arg Arg Arg Gly Arg Ser
1               5                   10

(2) INFORMATION FOR SEQ ID NO: 95:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 95:

Leu Pro Glu Thr Thr Val Val Arg Arg Arg Gly Arg
1               5                   10

(2) INFORMATION FOR SEQ ID NO: 96:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear -continued

```
        (ii) MOLECULE TYPE: peptide (xi) SEQUENCE DESCRIPTION: SEQ ID NO: 96:

Leu Pro Glu Thr Thr Val Val Arg Arg Arg Gly
1               5                   10

(2) INFORMATION FOR SEQ ID NO: 97:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 97:

Leu Pro Glu Thr Thr Val Val Arg Arg Arg
1               5                   10

(2) INFORMATION FOR SEQ ID NO: 98:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 98:

Leu Pro Glu Thr Thr Val Val Arg Arg
1               5

(2) INFORMATION FOR SEQ ID NO: 99:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 99:

Ala Ile Arg Leu Lys Val Phe Val Leu
1               5
```